United States Patent
Rich et al.

(10) Patent No.: US 6,316,405 B1
(45) Date of Patent: Nov. 13, 2001

(54) CYCLOSPORIN A CONJUGATES AND USES THEREFOR

(75) Inventors: Daniel H. Rich, Madison, WI (US); Michael E. Solomon, Arlington, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/242,724

(22) PCT Filed: Aug. 25, 1998

(86) PCT No.: PCT/US98/17544

§ 371 Date: Feb. 22, 1999

§ 102(e) Date: Feb. 22, 1999

Related U.S. Application Data

(60) Provisional application No. 60/057,751, filed on Aug. 26, 1997.

(51) Int. Cl.[7] .......................... A61K 38/00; A61K 38/12; C07K 16/00; C07K 17/00
(52) U.S. Cl. ...................... 514/9; 514/2; 514/14; 514/12; 435/7.1; 530/317; 530/326; 530/327
(58) Field of Search ............... 514/2, 9, 14, 12; 435/7.1; 530/317, 326, 327

(56) References Cited

FOREIGN PATENT DOCUMENTS

| WO 86 02080 A | 4/1986 | (WO) . |
| WO 96 06857 A | 3/1996 | (WO) . |
| WO 97 18828 A | 5/1997 | (WO) . |

OTHER PUBLICATIONS

Steiner et al., Neurorophic actions of nonimmunosuppressive analogues of immunosuppressive drugs FK506, rapamycin and clycosporin A, Nature Med. (1997) 3(4):421–428.*

Tjernberg et al., Controlling amyloid b–peptide fibril formation with protease–stable ligands, J. Biol. Chem. (1997) 272(19):12601–12605.*

Amara et al., A versatile synthetic dimerizer for the regulation of protein–protein interactions, Proceedings of the National Academy of Sciences, USA (1997) 94:10618–10623.*

Solomon, Michael Edward: "The Design and Synthesis of Novel Dual Inhibitor Cyclosporin A Conjugates" (1997) 397 pp. Avail.: UMI, Order No. DA9800016 From: Diss. Abstr. Int., B 1998, 59)2), 671, XP002086806.

Solomon, M.E., et al.: "Multi–site Inhibitors of HIV Replication Derived From Non–Immunosuppressive Analogs of Cyclosporine." 212th American Chemical Society National Meeting, Orlando, Florida, Aug. 25–29, 1996. Abstracts of Papers American Chemical Society 212 (1–2). 1996. Medi 208. ISSN: 0065–7727, XP0020868–7.

* cited by examiner

*Primary Examiner*—Karen Cochrane Carlson
*Assistant Examiner*—Stephen Tu
(74) *Attorney, Agent, or Firm*—Joseph T. Leone, Esq.; Dewitt Ross & Stevens S.C.

(57) ABSTRACT

Disclosed are conjugates of Aβ-binding peptides and CsA analogs and conjugates of Aβ-binding peptides and FK506 Binding Peptide inhibitors. These conjugates chemically induce dimerization of either cyclophilin or FK506 Binding Peptide with Aβ peptide, a major component of amyloid plaques found in neurological disorders such as Alzheimer's disease, multiple sclerosis, and amyotrophic lateral sclerosis. The conjugates are useful in the treatment of neurological diseases involving the formation of amyloid plaques because they inhibit and/or prevent the aggregation and deposition of Aβ peptide into plaques.

13 Claims, No Drawings

SEQUENCE LISTING

<160> NUMBER OF SEQ ID NOS: 33

<210> SEQ ID NO 1
<211> LENGTH: 11
<212> TYPE: PRT
<213> ORGANISM: Artificial Sequence
<220> FEATURE:

```
<221> NAME/KEY: MOD_RES
<222> LOCATION: (1)
<223> OTHER INFORMATION: MeBmt = (4R)
      -4-[(E)-2-butenyl]-4-N-methyl-(L)-threonine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeLeu = N-methyl-leucine
<221> NAME/KEY: MOD_RES
<222> LOCATION: (6)
<223> OTHER INFORMATION: MeLeu = N-methyl-leucine
<221> NAME/KEY: MOD_RES
<222> LOCATION: (8)
<223> OTHER INFORMATION: D-Ala = (D)-alanine
<221> NAME/KEY: MOD_RES
<222> LOCATION: (9)
<223> OTHER INFORMATION: MeLeu  = N-methyl-leucine
<221> NAME/KEY: MOD_RES
<222> LOCATION: (10)
<223> OTHER INFORMATION: MeLeu = N-methyl-leucine
<221> NAME/KEY: MOD_RES
<222> LOCATION: (11)
<223> OTHER INFORMATION: MeVal
<223> OTHER INFORMATION: Description of Artificial Sequence: synthetic
      polypeptide

<400> SEQUENCE: 1

Xaa Xaa Xaa Xaa Val Xaa Ala Ala Xaa Xaa Xaa
 1               5                  10

<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu; BLOCKED
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: 4Lys(2Cl-Cbz) =
      2-chlorobenxyloxycarbonyl-protected lysine;
      BLOCKED
<223> OTHER INFORMATION: Description of Artificial Sequence: synthesized
      polypeptide

<400> SEQUENCE: 2

Xaa Val Xaa Lys
 1

<210> SEQ ID NO 3
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: MeSer(Obn) = benzyloxy-protected N-methyl-
      serine; BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
<221> NAME/KEY: MOD_RES
<222> LOCATION: (5    5)
```

```
<223> OTHER INFORMATION: Lys(2Cl-Cbz) = 2-chlorobenzyloxycarbonyl-
      protected lysine; BLOCKED
<223> OTHER INFORMATION: Description of Artificial Sequence: synthesized
      polypeptide

<400> SEQUENCE: 3

Xaa Xaa Val Xaa Lys
  1           5

<210> SEQ ID NO 4
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: BLOCKED, Abu
<221> NAME/KEY: MOD_RES
<222> LOCATION: (2)
<223> OTHER INFORMATION: (D)MeSer(OBn) = (D)-N-methyl-serine,
      benzyloxy-protected
<221> NAME/KEY: MOD_RES
<222> LOCATION: (3)
<223> OTHER INFORMATION: MeLeu
<221> NAME/KEY: MOD_RES
<222> LOCATION: (5)
<223> OTHER INFORMATION: MeLeu
<221> NAME/KEY: MOD_RES
<222> LOCATION: (6)
<223> OTHER INFORMATION: Lys(2Cl-Cbz) = 2-chlorobenzyloxycarbonyl-
      protected lysine;  BLOCKED
<223> OTHER INFORMATION: Description of Artificial Sequence: synthesized
      polypeptide

<400> SEQUENCE: 4

Xaa Xaa Xaa Val Xaa Lys
  1               5

<210> SEQ ID NO 5
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbonyl-
      protected lysine;  BLOCKED
<223> OTHER INFORMATION: Description of Artificial Sequence: synthesized
      polypeptide

<400> SEQUENCE: 5

Xaa Xaa Xaa Xaa Val Xaa Lys
  1               5

<210> SEQ ID NO 6
<211> LENGTH: 7
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbony-
      protected lysine; BLOCKED
<223> OTHER INFORMATION: Description of Artificial Sequence: synthesized
      polypeptide

<400> SEQUENCE: 6

Xaa Xaa Xaa Xaa Val Xaa Lys
  1               5

<210> SEQ ID NO 7
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: (D) Ala;   BLOCKED
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)MeSer(OBn) = (D)-N-methyl-serine,
      benzyloxy-protected
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 7

Xaa Xaa Xaa Xaa Xaa Xaa Xaa Xaa Val Xaa Lys
  1               5                  10
```

```
<210> SEQ ID NO 8
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: MeAla = N-methyl-alanine;   BLOCKED
<221> NAME/KEY: MOD_RES
<222> LOCATION: (3)
<223> OTHER INFORMATION: MeAla
<221> NAME/KEY: MOD_RES
<222> LOCATION: (4)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence:
      synthesized polypeptide

<400> SEQUENCE: 8

Xaa Val Xaa Lys
  1

<210> SEQ ID NO 9
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeuLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) =
      2-chloro-benzyloxycarbonyl-protected lysine
<221> NAME/KEY: MOD_RES
<222> LOCATION: (8)
<223> OTHER INFORMATION: (D)-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal
<223> OTHER INFORMATION: Description of Artificial Sequence: synthesized
      polypeptide

<400> SEQUENCE: 9

Xaa Xaa Xaa Xaa Val Xaa Lys Ala Xaa Xaa Xaa
  1               5                  10

<210> SEQ ID NO 10
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)MeSer(OTBS) = (D)-N-methyl-serine,
```

```
        tert-butyldimethylsilyloxy-protected; BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
<221> NAME/KEY: MOD_RES
<222> LOCATION: (5)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 10

Xaa Xaa Val Xaa Lys
 1               5

<210> SEQ ID NO 11
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)MeSer = (D)-N-methyl-serine;   BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
<221> NAME/KEY: MOD_RES
<222> LOCATION: (5)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 11

Xaa Xaa Val Xaa Lys
 1               5

<210> SEQ ID NO 12
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Abu; BLOCKED
<221> NAME/KEY: MOD_RES
<222> LOCATION: (2)
<223> OTHER INFORMATION: (D)-MeSer = (D)-N-methyl-serine
<221> NAME/KEY: MOD_RES
<222> LOCATION: (3)
<223> OTHER INFORMATION: MeLeu
<221> NAME/KEY: MOD_RES
<222> LOCATION: (5)
<223> OTHER INFORMATION: MeLeu
<221> NAME/KEY: MOD_RES
<222> LOCATION: (6)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 12

Xaa Xaa Xaa Val Xaa Lys
 1               5
```

```
<210> SEQ ID NO 13
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)-MeSer
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chloro-benzyloxycarbony-
      protected lysine; BLOCKED
<223> OTHER INFORMATION: Description of Artificial Sequence: synthesized
      polypeptide

<400> SEQUENCE: 13

Xaa Xaa Xaa Xaa Val Xaa Lys
 1               5

<210> SEQ ID NO 14
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D) MeSer = (D)-N-methyl-serine
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 14

Xaa Xaa Xaa Xaa Val Xaa Lys
 1               5

<210> SEQ ID NO 15
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)-Ala;  BLOCKED
<221> NAME/KEY: MOD_RES
<222> LOCATION: (2)
```

```
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)MeSer = (D)-N-methyl-serine
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 15

Ala Xaa Xaa Xaa Xaa Xaa Xaa Xaa Val Xaa Lys
 1               5                  10

<210> SEQ ID NO 16
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbonyl-
      protected lysine
<221> NAME/KEY: MOD_RES
<222> LOCATION: (8)
<223> OTHER INFORMATION: (D-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal
<223> OTHER INFORMATION: Description of Artificial Sequence: synthesized
      polypeptide

<400> SEQUENCE: 16

Xaa Xaa Xaa Xaa Val Xaa Lys Ala Xaa Xaa Xaa
```

```
                1               5                    10
```

<210> SEQ ID NO 17
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: BLOCKED, Abu
<221> NAME/KEY: MOD_RES
<222> LOCATION: (2)
<223> OTHER INFORMATION: MeGly
<221> NAME/KEY: MOD_RES
<222> LOCATION: (3)
<223> OTHER INFORMATION: MeAla = N-methyl-alanine
<221> NAME/KEY: MOD_RES
<222> LOCATION: (5)
<223> OTHER INFORMATION: MeAla
<221> NAME/KEY: MOD_RES
<222> LOCATION: (6)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 17

Xaa Xaa Xaa Val Xaa Lys
 1               5

<210> SEQ ID NO 18
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeAla
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 18

Xaa Xaa Xaa Xaa Val Xaa Lys
 1               5

<210> SEQ ID NO 19
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)

```
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeAla
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 19

Xaa Xaa Xaa Xaa Val Xaa Lys
 1               5

<210> SEQ ID NO 20
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)-Ala: BLOCKED
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)MeSer(OBn) = (D)-N-methyl-serine,
      benzyloxy-protected
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 20

Ala Xaa Xaa Xaa Xaa Xaa Xaa Xaa Val Xaa Lys
 1               5                  10

<210> SEQ ID NO 21
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
```

```
            BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeAla
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine
<221> NAME/KEY: MOD_RES
<222> LOCATION: (8)
<223> OTHER INFORMATION: (D)-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal
<223> OTHER INFORMATION: Description of Artificial Sequence: synthesized
      polypeptide

<400> SEQUENCE: 21

Xaa Xaa Xaa Xaa Val Xaa Lys Ala Xaa Xaa Xaa
 1               5                  10

<210> SEQ ID NO 22
<211> LENGTH: 40
<212> TYPE: PRT
<213> ORGANISM: Homo sapiens

<400> SEQUENCE: 22

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 23
<211> LENGTH: 42
<212> TYPE: PRT
<213> ORGANISM: Homo sapiens

<400> SEQUENCE: 23

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 24
<211> LENGTH: 6
<212> TYPE: PRT
<213> ORGANISM: Artificial Sequence
<220> FEATURE:
<223> OTHER INFORMATION: :
```

```
<400> SEQUENCE: 24

Gln Lys Leu Val Phe Phe
 1               5

<210> SEQ ID NO 25
<211> LENGTH: 5
<212> TYPE: PRT
<213> ORGANISM: Artificial Sequence
<220> FEATURE:
<223> OTHER INFORMATION: :

<400> SEQUENCE: 25

Lys Leu Val Phe Phe
 1               5

<210> SEQ ID NO 26
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION; K(2Cl-Cbz) =
      2-chlorobenzyloxycarbonyl-protected lysine

<400> SEQUENCE: 26

Lys Leu Val Phe Phe
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: synthetic
      polypeptide
<221> NAME/KEY: MOD_RES
<222> LOCATION: (1)
<223> OTHER INFORMATION: ACETYLATION
<221> NAME/KEY: MOD_RES
<222> LOCATION: (2)
<223> OTHER INFORMATION: K(2Cl-Cbz) = 2-chlorobenzyloxycarbonyl-
      protected lysine

<400> SEQUENCE: 27

Glu Lys Leu Val Phe Phe
 1               5

<210> SEQ ID NO 28
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)Ala
<221> NAME/KEY: MOD_RES
<222> LOCATION: (2)
<223> OTHER INFORMATION: N-methyl-leucine
<221> NAME/KEY: MOD_RES
<222> LOCATION: (3)
<223> OTHER INFORMATION: N-methyl-leucine
<221> NAME/KEY: MOD_RES
<222> LOCATION: (4)
<223> OTHER INFORMATION: MeVal
<223> OTHER INFORMATION: Description of Artificial Sequence: synthetic
      polypeptide

<400> SEQUENCE: 28

Xaa Xaa Xaa Xaa
```

```
                                    1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 29

Leu Val Phe Phe
  1

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 30

Glu Lys Leu Val Phe Phe
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 31

Lys Leu Val Phe Phe Lys
  1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: synthetic
      polypeptide
<221> NAME/KEY: MOD_RES
<222> LOCATION: (1)
<223> OTHER INFORMATION: (D)-Ala
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH)
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: Sar
<221> NAME/KEY: MOD_RES
<222> LOCATION: (8)
<223> OTHER INFORMATION: MeAla
<221> NAME/KEY: MOD_RES
<222> LOCATION: (10)
<223> OTHER INFORMATION: MeAla
```

```
<400> SEQUENCE: 32

Xaa Xaa Xaa Xaa Xaa Xaa Xaa Xaa Val Xaa Lys
 1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 33

Lys Lys Leu Val Phe Phe
 1               5
```

CYCLOSPORIN A CONJUGATES AND USES THEREFOR

Priority is claimed to provisional application Serial No. 60/057,751, filed Aug. 26, 1997.

GOVERNMENT RIGHTS

This invention was made with United States government support awarded by the following agencies: NIH Grant Nos: AR32007 and GM50113. The United States has certain rights in this invention.

FIELD OF THE INVENTION

The invention is directed to conjugates of Aβ-binding peptides and cyclosporin analogs and conjugates of Aβ-binding peptides and FK506 Binding Protein inhibitors. The conjugates inhibit the aggregation and deposition of Aβ peptide into amyloid plaques and therefore find use in the prevention and treatment of disorders characterized by the formation of amyloid plaques.

DESCRIPTION OF THE PRIOR ART

Cyclosporin A (CsA) 1.1, marketed by Sandoz under the trademark "SANDIMMUNE," currently is the drug of choice for preventing rejection of transplanted human organs. CsA is a highly lipophilic, cyclic undecapeptide, cyclo (-MeBmt$^1$-Abu$^2$Sar$^3$-MeLeu$^4$-Val$^5$-MeLeu$^6$-Ala$^7$-(D)-Ala$^8$-MeLeu$^9$-MeLeu$^{10}$—MeVal$^{11}$-) (SEQ. ID. NO: 1), that contains 7 N-methyl amino acid residues and the novel amino acid (4R)-4-{(E)-2-butenyl}-N-methyl-(L)-threonine (abbreviated as MeBmt) in the 1-position. A number of synthetic routes are known in the art for solution-phase or solid-phase synthesis of CsA. See, for example, Rich et al. (1995), "Solid Phase Synthesis of Cyclosporin Peptides." *J. Am. Chem. Soc.* 117:7279–7280; Wenger, R. M. (1984), *Helv. chim. Acta* 67:502; and Wenger, R. M. (1985), *Angew. Chem. Int. Ed. Engl.* 24:77. CsA is depicted in structure 1.1:

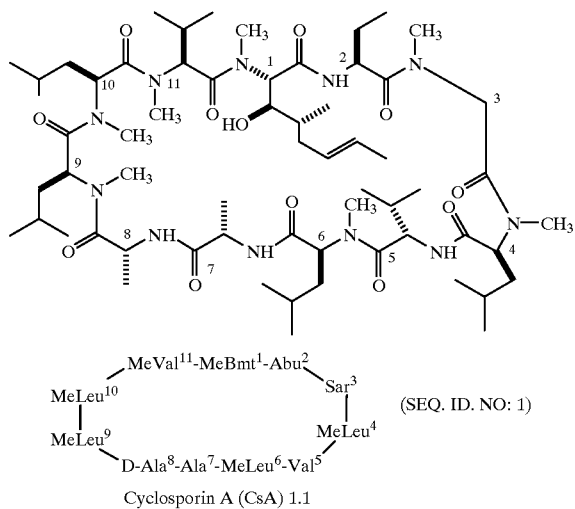

Cyclosporin A (CsA) 1.1

CzA is produced by the fungus *Tolypocladium niveum* and was first isolated in 1976 by workers at Sandoz. In 1983, CsA was approved by the U.S. Food and Drug Administration for use as an immunosuppressant in the United States.

The structure of CsA has been confirmed by total synthesis, Wenger (1984), *Helv. Chim. Acta*, 67:502, and the conformations of CsA free in solution and bound to the protein cyclophilin have been solved by NMR and X-ray crystlography. Looslie et al. (1985), *Helv. Chim. Acta*, 68:682 and Mikol (1993), *J. Mol. Biol.*, 234:1119, respectively.

Several modified cyclosporin derivatives are described in the prior art. A shorthand notation for designating cyclosporin analogs has developed in which any modified amino acids and their positions relative to unmodified CsA are listed. This makes for a very simple and unambiquous designation of cyclosporin analogs based upon their differences from natural CsA. For example, an analog of CsA possessing a serine residue in place of the normal valine as the fifth amino acid residue is designated (Ser$^5$)-CsA. This conventional shall be consistently employed herein.

CsA analogs containing modified amino acids in the 1-position are reported by Rich et al. (1986), *J. Med. Chem.*, 29:978. Strongly immunosuppressive, anti-inflammatory, and anti-parasitic CsA analogs are described in U.S. Pat. Nos. 4,384,996; 4,771,122; and 5,284,826, all assigned to Sandoz. Among the CsA analogs described in these patents are (AllylGly$^2$)-CsA, ((D)-Ser$^8$)-CsA, and (O-(2-hydroxyethyl)(D)Ser$^8$) CsA.

In 1984, Handschumacher et al. reported the discovery of a CsA binding protein, named cyclophilin (Cyp), that binds CsA with a dissociation constant of approximately 20 nM. Handschumacher et al. (1984) *Sience* 226:544. It was later shown that Cyp is homologous with peptidyl prolylisomerase (PPIase) a ubiquitous family of proteins found in a variety of cell types. See Takahashi (1989), *Nature* 337:473 and Fischer et al. (1989) *Nature* 337:476. Cyclophilins catalyze the cis-trans isomerization of Xaa-Pro bonds and are hypothesized to play a role in protein folding, although this functionality remains uncertain. See, for instance, Fischer (1994), *Angew. Chem. Int. Ed. Engl.* 33:1415 and Schmid (1993), *Ann. Rev. Biophys. Biomol. Struct.* 22:123.

The identification of Cyp as a PPIase suggested that CsA exerts its immunosuppressive effect by inhibiting the PPIase activity of Cyp, thereby causing improper folding of proteins which are crucial to the immune response Sigal et al. (1991), *J. Exp. Med.* 173:619. This hypothesis was originally strengthened by the discovery that the macrolide FK506, 1.2, has potent immunosuppressive activity and inhibits the PPIase activity of FK506 binding protein (FKBP). Siekerka et al. (1989), *Nature* 341:755.

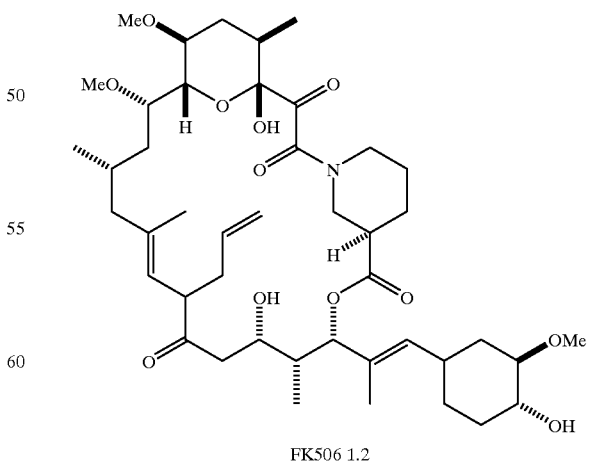

FK506 1.2

Further investigations, however, revealed several discrepancies regarding the inhibition of PPIase as a mechanism leading to immunosuppression. Foremost, the concentrations of CsA and FK506 required to ellicit immunosuppression are far lower than the concentrations of Cyp within a cell. Additionally, mutants of yeast and neurospora which lack the Cyp gene are resistant to cyclosporin but are still viable. See Agarwal et al. (1987), *Transplantation* 42:627; Tropschung et al. (1989), *Nature* 342:953; and Hayano et al. (1991), *Biochem.* 30:3041. Another observation at odds with the original hypothesis was that although CsA and FK506 exhibit very similar in vivo and in vitro effects, CsA does not bind to FKBP and FK506 does not bind to Cyp. Schreiber and Crabtree (1992), *Immunology Today* 13:136. The PPIase inhibition hypothesis was further weakened with the discovery that several potent PPIase inhibitors do not cause immunosuppression. See, for example, Somers et al. (1991), *J. Am. Chem. Soc.* 113:8045.

In 1991, Liu et al. reported that the CsA-Cyp complex binds with high affinity to calcineurin, a calcium dependent serine/threonine phosphatase, Liu et al. (1991), *Cell* 66:807; and Liu et al. (1992), *Biochem.* 31:3896. Calcineurin is thought to cleave a phosphate group from the nuclear factor of activated T-cells (NF-AT), allowing its translocation into the nucleus where it activates the gene for interleukin-2. See Schreiber and Crabtree (1992), supra. Inhibition of calcineurin is now generally accepted as the mechanism of immunosuppression by both CsA and FK506. See, for example, Ho et al. (1996), *Clin. Immun. and Immunopathology*, 80:S40. CsA binds to Cyp by an interaction between residues 9-10-11-1-2 of the CsA and an active site on Cyp residues. 9-10-11-1-2 of CsA are therefore referred to as the "binding domain." Calcineurin is bound to CsA by an analogous interaction including residues 4-5-6-7-8 of CsA. These residues are therefore referred to as the "effector domain":

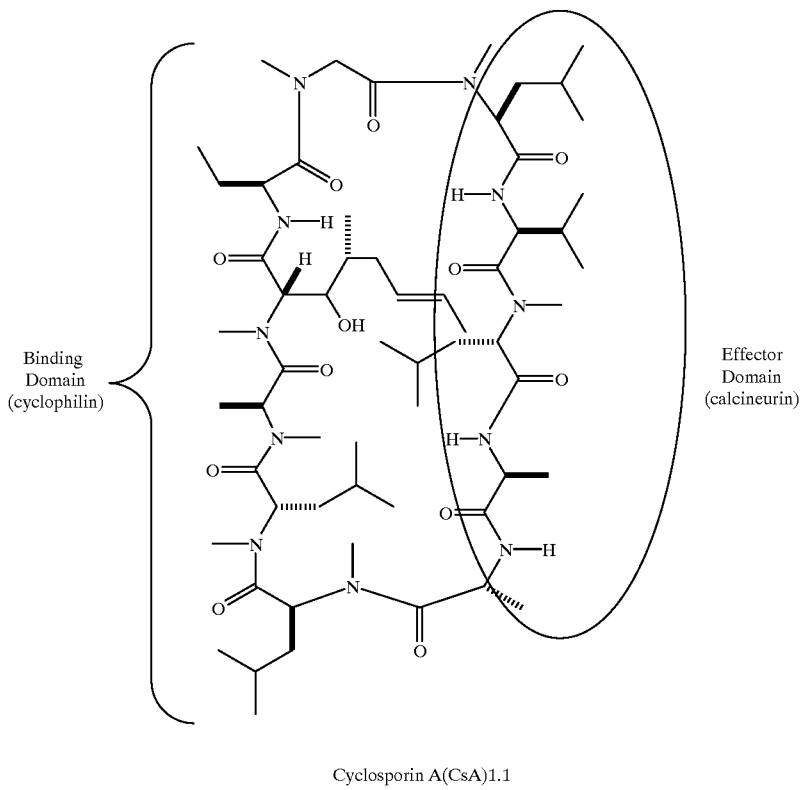

Cyclosporin A(CsA)1.1

Interestingly, both CsA and FK506 exhibit potent neurotrophic (nerve regeneration) effects, with FK506 showing significant neurotrophic activity at concentrations as low as 1 pM. Lyons et al. (1994), *Proc. Natl. Acad. Sci. U.S.A.* 91:3191; Steine et al. (1997), *Nature Medicine* 3:421. The mechanism by which these compounds exert their neurotrophic activity is unclear, although Nerve Growth Factor (NGF) must be present for the activity to be present.

Chemical Induced Dimerization (CID) involves the dimerization of two biomolecules by a cell-permeable organic compound which "turns on" a specific biological event. (See, for example, Crabtree and Schreiber (1996) *Trends in Biochemical Sciences* 21:418.) The technique relies on the principle of induced proximity, where the process of bringing two parts of an activation system into close contact is sufficient to activate the biological process.

Transcription factors, for example, are highly modular and the activation domain can be separated from the DNA binding domain. Attachment of each domain to a drug-binding protein allows the drug-dimer to bring the DNA binding and activation domains into close proximity by binding the fusion proteins, thereby turning on the gene expression. There are two important aspects CID that are attractive: the drug-dimer controlled gene expression can be "shut off" by addition of drug monomer, and the modular nature of the designed transcription factors means that each fusion protein/CID complex can be optimized for any given system, and that two or more biological events could be simultaneously controlled by using different fusion protein/CID complexes.

A significant advance in the CID technology was the use of orally-active rapamycin as the drug dimerizer. Rivera et al. (1990) *Nature Medicine* 2:1028. Rapamycin can bind both FKBP and FRAP, a lipid kinase. FRAP could be further truncated to an 89-amino acid peptide, termed FRB, that retains binding to rapamycin. Addition of rapamycin to a cell line expressing a DNA binding domain with three FKBP modules and an activation domain containing one FRB caused the rapid induction of the reporter gene. Furthermore, an hGH gene with the appropriate fusion proteins was injected into nude mice. Intravenous addition of rapamycin to the mice produced dosedent and sustainable levels of hGH in the serum with negligible background.

The prominent limitation of the rapamycin system is that the compound in immunosuppressive and thus could not be used in a human gene therapy platform. This problem was overcome in part by modification of rapamycin such that it could bind a mutant FRAP or FRB protein, but can no longer bind endogenous FRAP. Clackson (1997) *Curr. Opin. Chem. Biol.* 1:210. This type of protein engineering has also produced mutant cyclophilins that bind to non-immunosuppressive CsA analogs, as well as FKBP ligands that tightly bind an FKBP mutant, but are poor binders of natural human FKBP. Belshaw et al. (1995) *Angew Chem. Int. Ed. Engl.* 34:2129; Belshaw and Schreiber (1997) *J. Am. Chem. Soc.* 119:1805.

In 1907, Alois Alzheimer described a novel brain disease that is characterized by insoluble plaques in the brain, and loss of memory and mental capacity. The core of the insoluble plaques contains two peptides, mainly Aβ 1-40 and a lesser amount of Aβ 1-42. (These two peptides, which are identical except for the two C-terminal residues in Aβ 1-42, are referred to collectively herein as Aβ or Aβ peptide.) Both peptides are derived from β-amyloid precursor protein (APP), a trans-membrane glycoprotein encoded on chromosome 21:

Aβ 1-40 (SEQ. ID. NO: 22): H₂N-DAERHDSGYEVHHQKLVFFAEDVGSNKGAII GLMVGGVV-CO₂H

Aβ 1-42 (SEQ. ID. NO: 23): H₂N-DAEFRHDSGYEVHHQKLVFFAEDVGSNKGAII GLMVGGVVIA-CO₂H

Production of the Aβ peptide requires cleavage of APP at an extracellular position to leave a 100 amino acid peptide that is then cleaved in the transmembrane domain to form the 39-43 amino acid Aβ peptide. Selkoe (1997) *Science* 275:630. Initial nucleation of the Aβ peptide may take place in a cellular compartment, where after attainment of a critical concentration of Aβ, the nucleation product is expelled and extracellular amyloid formation occurs. Lansbury (1997) *Curr. Opin. Chem. Bio* 1:260.

Strong evidence indicates that aggregation of the Aβ peptide and subsequent plaque formation is the main cause of the neuronal damage and dementia observed in Alzheimer's disease and other neurological disorders such as multiple sclerosis and amyotrophic lateral sclerosis.

Additionally, all genetic mutants for Alzheimer's disease reported to date increase secretion of the Aβ 1-42 peptide, which has a higher propensity to form fibrils than Aβ 1-40. See Selkoe (1997), supra. Point mutations near the excision ends of the Aβ peptide sequence in APP are associated with a rare early-onset Alzheimer condition, termed familial Aβ (FAD), which increases the ratio of Aβ 1-42 to Aβ 1-40 produced. These data are consistent with Lansbury's report that Aβ 1-42 nucleates more rapidly into fibrils than Aβ 1-40.

Mutations in the presenilin (PS) 1 and 2 genes also have been reported to affect the processing of APP. A significant increase in Aβ 1-42 occurs in the plasma of patients with the PS mutations prior to the onset of symptoms and inspection of cadaver's brains with PS mutations also show higher density plaques. Scheuner et al. (1996) *Nature Medicine* 2:864; Lemere et al. (1996) *Nature Medicine* 2:1146. The transfection of mutant PS cDNA's into cell cultures causes the increased formation of Aβ 1-42 which indicates that no other neural process is required to produce the Aβ peptide. Citron et al. (1997) *Nature Medicine* 3:67. Furthermore, transgenic mice expressing mutant PS1 exhibit higher levels of Aβ 1-42 in the brain. An interaction between PS and APP has been observed in the endoplasmic reticulum indicating formation or disruption of the complex may be responsible for the increased Aβ 1-42 production. Weidemann et al. (1997) *Nature Medicine* 3:328.

Further evidence implicating Aβ fibrils and plaques in seen in Down's syndrome patients. People with Down's syndrome have an extra copy of the gene that encodes APP (chromosome 21) which causes them to express abnormally high levels of APP and usually develop early-onset Alzheimer's disease. Additionally, Down's infants show evidence of plaque formation prior to the onset of symptoms, which supports the hypothesis that plaque plays a causative role, rather than an incidental role. Since Aβ fibril formation is a pathological process, inhibition of fibrillation is an attractive and potentially effective therapy to treat Alzheimer's disease, as well as other neurological conditions characterized by the formations of plaques.

SUMMARY OF THE INVENTION

The invention is drawn to compounds of formula A-Z, characterized in that A is selected from the group consisting of

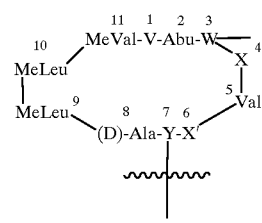

-continued

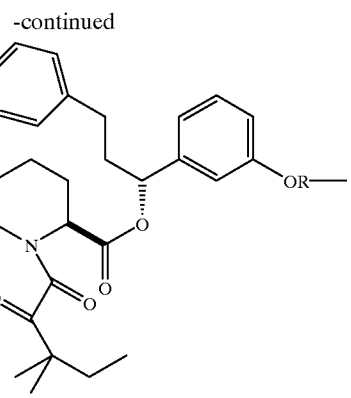

wherein R is a $C_2$ to $C_6$ alkylcartoxy group (—$(CH_2)_{1-5}C(=O)O$—);

V is a MeLeu(3-OH), MeLeu, MeSer, MeSer-PG, MeThr, or MeThr-PG residue;

W is a (D))-N-methyl-amino acid or an N-methylglycyl residue;

X and X' are independently an N-methyl-leucinyl or an N-methylalanyl residue;

Y is a lysyl, homo-lysyl, ornithinyl, lysyl-PG, homo-lysyl-PG, or ornithinyl-PG residue;

wherein each PG is, independently, a side-chain protecting group; and

Z is a polypeptide comprising 5 or more contiguous residues of Aβ peptide; and salts thereof.

The invention is further drawn a composition for the treatment of neurological disorders in humans involving the formation of amyloid plaques, including Alzheimer's disease, multiple sclas, and amyotrophic lateral sclerosis. The composition is characterized by an amount of one or more compounds described immediately above, or a pharmaceutically-acceptable salt thereof, in combination with a pharmaceutically-acceptable carrier, wherein the amount is effective to inhibit formation of amyloid plaques in a mammal, including humans.

The invention is likewise drawn to use of one or more compounds described immediately above, or a pharmaceutically-acceptable salt, in the manufacture of a medicament for the treatment of neurological disorders in humans involving the formation of amyloid plaques.

A distinct advantage of the present invention is that it provides novel chemical inducers of dimerization which are non-immunosuppresive and which are inhibitors of Aβ peptide aggregation and deposition. These compounds are therefore highly effective to treat or prevent neurological disorders caused, in whole or in part, by the formation of amyloid plaques, including Alzheimer's disease, multiple sclerosis, and amyotrophic lateral sclerosis. While not being bound to a particular mechanism, it is believed that by inhibiting the aggregation of Aβ peptide into fibrils, the subject compounds inhibit the onset and progression of Alzheimer's disease. Further still, the compounds including a CsA moiety may act synergistically by inhibiting Aβ peptide plaque formation while stimulating neurotrophic activity.

Another advantage of the invention is that it provides a generalized approach to chemically inducing dimerization between Aβ peptide and more ubiquitous proteins such as cyclophilin and FKBP. By linking these two systems, the adverse consequences of amyloid plaque formation can be prevented or ameliorated by in effect sequestering the Aβ peptide in monomeric form with a conjugate which links the Aβ to cyclophilin or FKBP. This provides a mechanism by which the amount of free Aβ available for fibril formation and deposition can be minimized.

DETAILED DESCRIPTION OF THE INVENTION

Abbreviations and Definitions:

To aid in a consistent understanding of the invention, the following abbreviations and definitions shall be used herein:

Aβ Peptide: A 39 to 43 residue peptide which is the main constituent of amyloid plaque. Aggregation and deposition of Aβ peptide into plaques is thought to be the cause of Alzheimer's disease.

Binding Domain of CsA: The sub-domain of cyclosporin and cyclosporin analogs which binds to cyclophilin. The binding domain generally includes residues 9-10-11-1-2 of cyclosporin.

Cyclophilin (Cyp): A ubiquitous cytosolic protein having PPIase activity. Cyclosporins bind to and inhibit the action of cyclophilin.

Cyclosporin A (CsA): As used herein, the terms "cyclosporin," "cyclosporin derivative," and "cyclosporin analog" denote any compound having the fundamental structure of cyclosporin A, namely a cyclic undecapeptide having a number of N-methyl-substituted amino acid residues, with amino acid substitutions at defined positions within the molecule.

Cyclosporin Conjugates: A CsA analog or derivative conjugated to an exocyclic moiety, especially but not exclusively at position-7 of the CsA skeleton. Cyclosporin conjugates are molecules which retain the ability to bind to cyclophilin.

Effector Domain of CsA: In unmodified CsA, the sub-domain which binds to calcineurin. Generally includes residues 4-5-6-7-8 of the CsA molecule. In CsA analogs and conjugates, the effector domain is the region of the CsA skeleton where various anti-HIV substituents are attached to the CsA molecule to alter the specificity of the CsA analog or conjugate. FK506-Binding Protein (FKBP): A cytosolic protein having PPIase activity which is bound to and inhibited by FK506.

Modified Residues, Reagents, Protecting Groups, and Solvents: Abu=α-aminobutyric acid, Bn=benzyl, Boc=t-butoxycarbonyl, BOP=benzotriazolyl-N-oxy-tris(dimethylamino)phosphonium hexaflurophosphate BOP-Cl=bis(2-oxo-3-oxamolidinyl phosphonic chloride, Cbn=benzylcarbonyl, Cbz=benzyloxycarbonyl, 2Cl-Cbz=2-chlorobenzcarbonyl, DCC=dicyclohexyl carbodiimide, DCU=dicyclohexylurea, DIBAL=diisobutylaluminum hydride, DIEA=diisopropylethylamine, DIPCDI=diisopropylcarbodiimide, DMAP=4-dimethylaminopyridine, DMP=dimethylformamide, EthOAc=ethylacetate, FABMS=Fast Atom Bombardment Mass Spectrometry, Fmoc=9-fluorenylmethoxycarbonyl, HATU=O-(7-azabenzotriazol-1-yl)-1,1,2,2-tetramethyluronium hexafluorophosphate, HEA=hydroxyethyl amine, HOBt=1-hydroxybenzotriazole, LAH=lithium alumunium hydroxide, MeLeu(3-OH)=3-hydroxy-N-methyl-leucine, MTBE=methyl-t-butyl ether, NMM: N-methylmorpholine, NMP=N-methyl pyrrolidinone, OBn=benzyloxy, OTBS=t-butyldimethylsilyloxy, PyAOP=7-azabenzotriazole-1-yl oxytris (pyrodidino) phosphonium hexafluorophosphate, Sar=sarcosine, TBAF=tetrabutylammonium fluoride, TBS=t-butyldimethylsilyl, TBS-Cl=t-butyldimethylsilyl chloride, TEA=triethyl amine, TFA=trifluoroacetic acid, THF=tetrahydrofuran, TMS=tetramethylsilyl, TLC=thin layer chromatography, Trt=trityl (i.e., triphenylmethyl).

Peptidyl prolylisomerase (PPIase): The functional class of enzymes to which cyclophilin belongs. PPIase catalyzes the cis-trans conversion of Xaa-Pro bonds.

Overview:

The invention is drawn to conjugates which simultaneously bind to cyclophilin (Cyp) or FKBP and a protein other than calcineurin in a biological system. In particular, the invention encompasses a class of compounds in which a fragment of Aβ peptide is conjugated to a CsA analog or an FKBP inhibitor. The resulting conjugate functions as a dimerizing agent which simultaneously binds to Cyp or FKBP and Aβ peptide, thereby preventing the aggregation and/or deposition of the Aβ peptide into plaques. By judiciously altering the structure of natural CsA, the CsA conjugates described herein are non-immunosuppresive and strongly inhibitory of Aβ peptide fibril formation.

Moreover, as noted above, the CsA-containing conjugates may act synergistically by inhibiting plaque formation while stimulating neurotrophic activity.

The Aβ-binding peptide fragment is preferably taken from residues corresponding to the 17-21 position of the Aβ peptide itself. In particular, one embodiment utilizes the sequence QKLVFF (SEQ. ID. NO: 24) (compound 11.23), which is coupled via its carboxy terminus to the other half of the conjugate. The sequence LVFF (SEQ. ID. NO: 29) (11.31) was similarly coupled to CsA analogs of FKBP inhibitors to yield useful conjugates. A conjugate using EKLVFF (SEQ. ID. NO: 30), bound to the remainder of the molecule via the glutamic acid side chain instead of through the C-terminus was also constructed (11.33). This arrangement places the Aβ binding peptide moiety of the conjugate perpendicular to the CsA ring.

What follows is a description of the chemical reactions by which the subject conjugates are made, followed by a description of incorporating the analogs and conjugates into pharmaceutical compositions for the treatment of disorders mediated by the formation of amyloid plaques. The "Examples" section includes illustrative synthetic protocols for making the subject compounds.

Chemistry:

Synthesis of (2S,3R)-MeLeu(3-OH):

Route 1: The first route to (2S,3R)-MeLeu(3-OH), is based on a (2R,3R)-Leu(3-OH) synthesis reported by Evans et al (1987), *Tetrahedron Lett.*, 28:39 uses a boron enolate mediated Evans aldol reaction and an efficient epimerization of a cis- to trans-oxazolidonone as the key steps (Scheme 3.3). Boron triflate-mediated condensation of the bromoacetyl chiral auxiliary 3.7, obtained from the chiral auxiliary in 82% yield, with isobutrylaldehyde yielded the aldol product 3.8 in 50% yield.

Scheme 3.3
Synthesis of intermediate carbamate 3.9 using an Evans aldol Reaction.

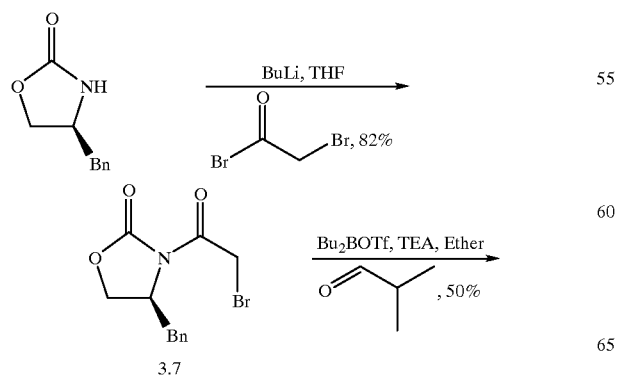

Reaction of the methylisocyanate with 3.8 catalyzed by BF$_3$OEt$_2$, produces the carbamate 3.9 in 80% yield. Removal of the chiral auxiliary with LiOH and cyclization of the carbamate with tert-butoxide gives the cis-onxazolidinone 3.10 in 74% yield (Scheme 3.4). Reaction of acid 3.10 with TMS-diazomethane gives the cis-oxazolidinone methyl ester 3.11, which is efficiently epimerized to the desired trans-oxazorlidinone acid 3.12 with KOH/ethanol and then hydrolysed to (2S,3R)-MeLeu(3-OH) 3.6 with KOH(aq) in 73% overall yield. Although this chiral synthesis of (2S,3R)-MeLeu(3-OH) requires fewer purification steps and affords easy isolation of intermediates, the mass of the chiral auxiliary made scaling up impractical on >0.5 g reactions.

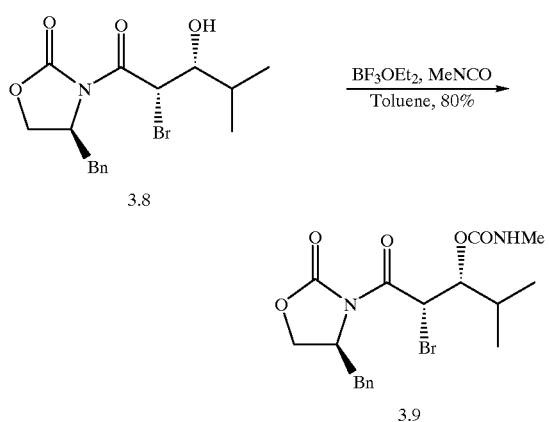

Scheme 3.4
Synthesis of 2S, 3R MeLeu (3-OH) 3.6 using an Evans Aldol Reaction.

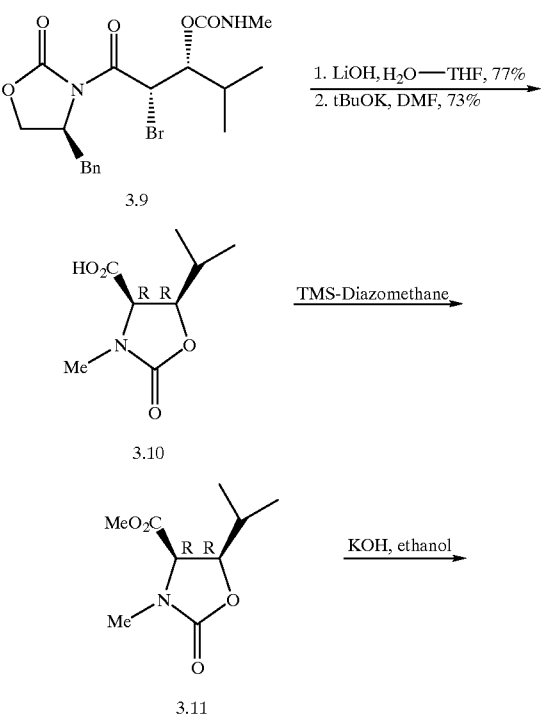

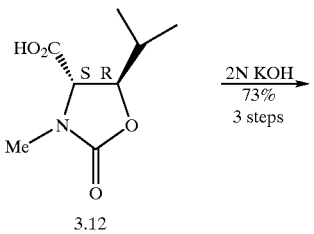

Route 2. Synthesis of (2S,3R)-Meleu(3-OH)

A second synthesis of (2S,3R)-Meleu(3-OH) was developed based on a Leu(3-OH) synthesis (all 4 isomers) reported by Omura et al. (1993), *Tetrahedron Lett.* 34:4447; and (1996), *J. Am. Chem. Soc.* 118:3584. The Sharpless asymmetric epoxidation reaction is used to set the stereocenters and the cis to trans-oxazolidinone epimerization described in Route 1 is used to produce the correct stereochemistry of the final product (Scheme 3.5). The αβ-unsaturated ester 3.13 is reduced with DIBAL to the allylic alcohol 3.14, which is epoxidized using D-diethyl tartarate to yield the epoxy alcohol 3.15 in good yield. Treatment of 3.15 with NaH and MeNCO at reflux produces a mixture of oxazolidinone isomers, some decomposition products, and only a low yield of the desired oxazolidinone 3.16. Oxidation of the alcohol 3.16 with a Jones reagent gives acid 3.10, which is treated with TMS-diazomethane to give the methyl ester 3.11 in 70% overall yield (Scheme 3.6). Epimerization and hydrolysis of the (2R,3R) methyl ester 3.11 with KOH/ethanol gives (2S,3R) oxazolidinone acid 3.12, which is not isolated, but hydrolysed directly with KOH(aq) to the desired (2S,3R)-MeLeu(3-OH) 3.6.

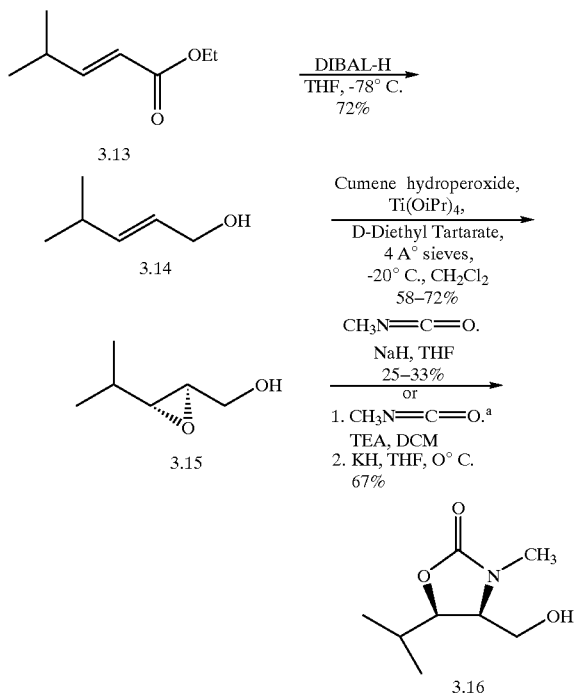

Scheme 3.5
Synthesis of 2R, 3R oxazolidinone 3.16 using the Sharpless asymmetric expoxidation reaction.

<sup>a</sup>see Scheme 3.7 for conditions

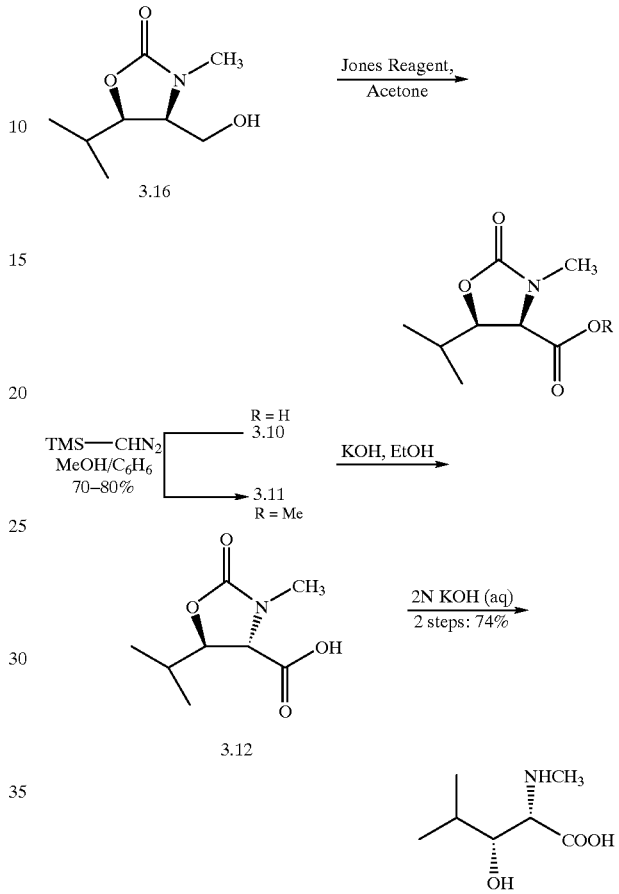

Scheme 3.6
Synthesis of 2S, 3R MeLeu (3-OH) 3.6 using the Sharpless asymmetric epoxidation reaction.

Optimized Route to Oxazolidinone 3.16.

The synthesis of (2S,3R)-MeLeu(3-OH) in Scheme 3.5 is not optimal in that the conversion of the epoxy alcohol 3.15 to the desired oxazolidinone isomer 3.16 proceeds in consistently low yields. This is overcome by pre-forming the carbamate before oxazolidinone formation, by using a stronger base in the oxazolidinone isomerization step, and by varying the reaction temperature (Scheme 3.7). Treatment of the epoxy alcohol 3.15 with Et$_3$N and MeNCO produces the epoxy carbamate 3.17 in excellent yield. Reaction of the carbamate 3.17 with NaH/THF at reflux yields the desired oxazolidinone 3.16, in the same yield as the one-pot reaction. KH, a stronger base than NaH, causes significantly larger amounts of decomposition at reflux temperatures. It was found that treatment of the epoxycarbamate 3.17 with 1.5 equivalents of KH at 0° C. for 1 hour, followed by warming to room temperature for 2 hours gives an 85% yield of the products with a 4:1 ratio of the desired oxazolidinone 3.16 isomer to the undesired oxazolidinone 3.18. Thus, a novel synthesis of (2S,3R)-MeLeu(3-OH) has been achieved by use of the Sharpless assymmetric epoxidation, followed by oxazolidinone isomerization with KH, and oxazolidinone epimerization to the desired trans-oxzlidinone. This synthesis is rapid, requires few purification steps, and facilitates the large scale synthesis of (2S,3R)-MeLeu(3-OH) for incorporation into CsA analogs.

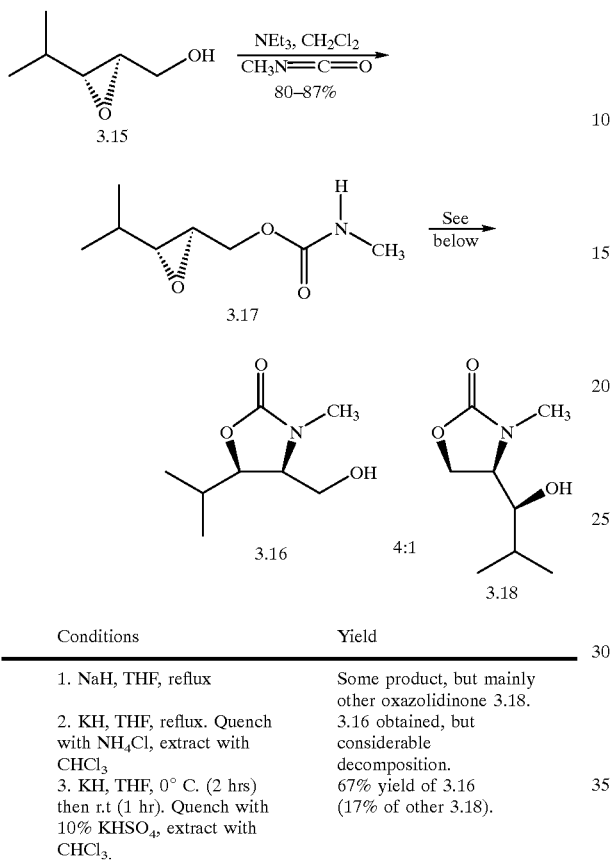

Scheme 3.7.
Optimization of oxazolidinone isomerization reaction to form 3.16.

| Conditions | Yield |
|---|---|
| 1. NaH, THF, reflux | Some product, but mainly other oxazolidinone 3.18. |
| 2. KH, THF, reflux. Quench with NH$_4$Cl, extract with CHCl$_3$ | 3.16 obtained, but considerable decomposition. |
| 3. KH, THF, 0° C. (2 hrs) then r.t (1 hr). Quench with 10% KHSO$_4$, extract with CHCl$_3$. | 67% yield of 3.16 (17% of other 3.18). |

Synthesis of CsA Analogs:

The synthesis of the CsA analogs follows the modified Wenger procedure reported by Colucci et al. (1990), *J. Org. Chem.* 55:2895 (Scheme 4.1). Notable parts of the synthesis include the undecapeptide cyclization between the Ala$^7$-DAla$^8$ residues, the "7+4" (1–7 residues+8–11 residues) segment coupling to produce the undecapeptide, and use of BOP-Cl reagent for peptide couplings. (See "Wenger's CsA Strategy.")

Cycliiaton between the alanines encounters the least steric bulk, no N-methylated residues, and an intramolecular hydrogen bonding pattern that may facilitate cyclization. The improved cyclization procedure involves simultaneous double deprotection of the Fmoc-protected N-terminus and the benzyl ester-protected C-terminus of the undecapeptide with NaOH(aq)/ethanol. The undecapeptide is formed via a "7+4" segment coupling so that the valuable β-OH amino acid (MeBmt$^1$-(2S,3R) or MeLeu(3-OH)$^1$) can be incorporated late in the synthesis. Undecapeptide formation also employs the BOP reagent which results in little epimerization of MeVal$^{11}$.

Wenger's synthesis of the "4" (8–11 position residues) segment tetrapeptide is based on an unconventional synthetic strategy in that the synthesis proceeds from the left to the right in order to avoid rapid diketopiperazine formation of the H-MeLeu-MeVal-OBn dipeptide Scheme 4.2. Tung et al. (1986), *J. Org. Chem.* 51:3350 found that by using Fmoc/tBu protection, diketopiperazine formation is inhibited so that conventional right to left synthesis proceeds without epimerization of each stereogenic center (see scheme "Strategies for synthesis of 8–11 CsA tetrapeptide"). Another major improvement over the Wenger procedure is the use of BOP-Cl for coupling of N-methyl amino acids. In his original synthesis of the 8–11 and 2–7 segments, Wenger used the mixed anhydride method, which requires low temperatures and long reaction times. The use of BOP-Cl as a N-alkyl peptide coupling reagent significantly improves the ease of CsA synthesis due to its manageable temperatures (0° C. to RT) and shorter reaction times. Thus, the combination of Wenger's overall strategy with the improved synthetic procedures described herein produces a very powerful method for generating diverse CsA analogs.

Strategies for the synthesis of 8–11 CsA tetrapeptide.

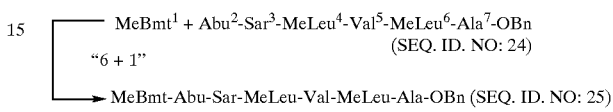

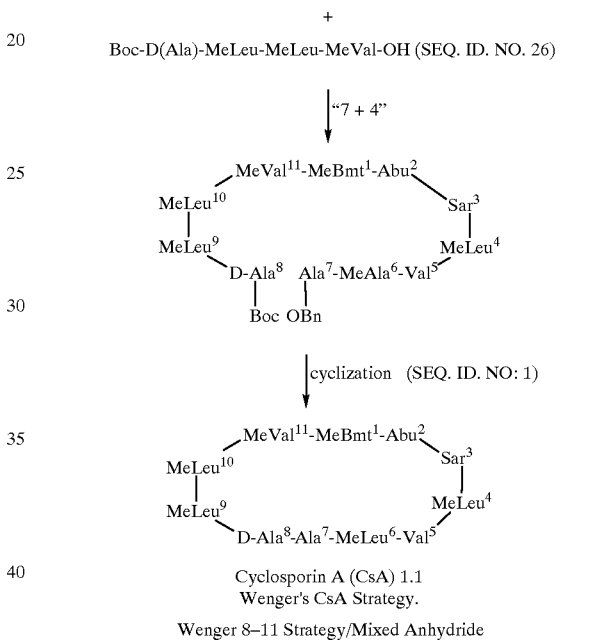

Wenger 8–11 Strategy/Mixed Anhydride

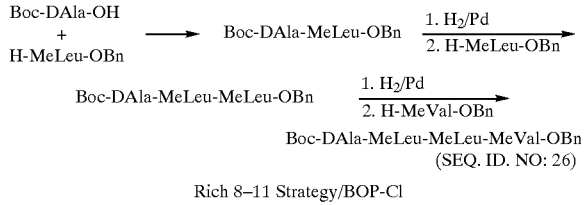

Rich 8–11 Strategy/BOP-Cl

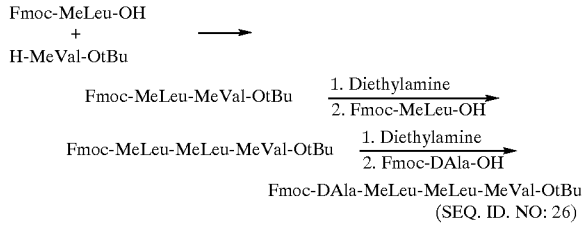

Synthesis of ([MeLeu(3-OH)$^1$, D-MeSer (OBn)$^3$, Lys(2Cl-Cbz)$^7$])CsA:

The synthesis of 1, 3, and 7-position substituted CsA analogs follows the procedure reported by Colucci et al (Scheme 4.1), modified so that the 2–7 segment is synthesized linearly (Scheme 4.1) and not in a "4+2" fashion due to problems with epimerization. When the 2–3 dipeptide with D-MeSer(OBn) in the 3-position is coupled to the CsA 4–7 tetrapeptide, significant epimerization if the D-MeSer)OBn) residue was observed (Scheme 4.2). Wenger attempted to synthesize the 2–7 CsA sequence linearly, but was unsuccessful due to rapid dikepiperazine formation of the Sar[3]-MeLeu[4] fragment. However, we were able to synthesize the D-MeSer(OBn)[3] 2–7 CsA peptide linearly without any observed diketopiperazine formation. Furthermore, Seebach et al. (1993), *Helv. Chim. Acta.* 76:1564, has also reported a successful linear synthesis of a 2–7 CsA analog with MeAla in the 3-position.

Lys(εN-2Cl-Cbz)[7] and D-MeSer(OBn)[3] side-chain protection was chosen because both protecting groups survive the acidic conditions required for the CsA analog synthesis, and because hydrogenation cleaves both groups without decomposing the CsA analog. Furthermore, hydrogenation of the Lys(εN-2Cl-Cbz)[7] produces a free amine which is used as a "handle" to attach other compounds to the CsA analog.

Boc-MeLeu-OH was coupled with H-Lys(2Cl-Z)-OBn to yield dipeptide 4.1 on good yield (Scheme 4.1). Cleavage of the Boc group from 4.1 with HCl/dioxane followed by reaction with Boc-Val-OH gives the tripeptide 4.2 in fair yield consistent with yields reported by Colucci et al for coupling to Boc-Val-OH. Deprotection of 4.2 and coupling with Boc-MeLeu-OH produces the 4–7 tetrapeptide 4.3 in 69% yield. Treatment of tetrapeptide 4.3 with TFA to cleave the Boc group, neutralization of the salt with NaHCO$_3$, followed by coupling to Boc-D-MeSer(OBn)-OH produces 4.4 in 71% yield. Cleavage of the Boc group from 4.4, neutralization and coupling to Boc-Abu-OH with BOP-Cl produces the hexapeptide 4.5 in 69% yield. No detectable epimerization of diketopiperazine formation is observed for this step. When a "4+2" coupling between Boc-Abu-D-MeSer(OBn)-OH+H-MeLeu-Val-MeLeu-Lys(2Cl-Z)-OBn SEQ. ID. NO: 2 is attempted, significant epimerization of the D-MeSer(OBn) residue occurrs as expected for an acyl-peptide coupling (Scheme 4.2).

Scheme 4.1

Snythesis of (2–7) hexapeptide 4.5 precursor of [MeLeu (3-OH)[1], DMeSer (OBn)[3], Lys (2Cl-Cbz)[7]] CsA.

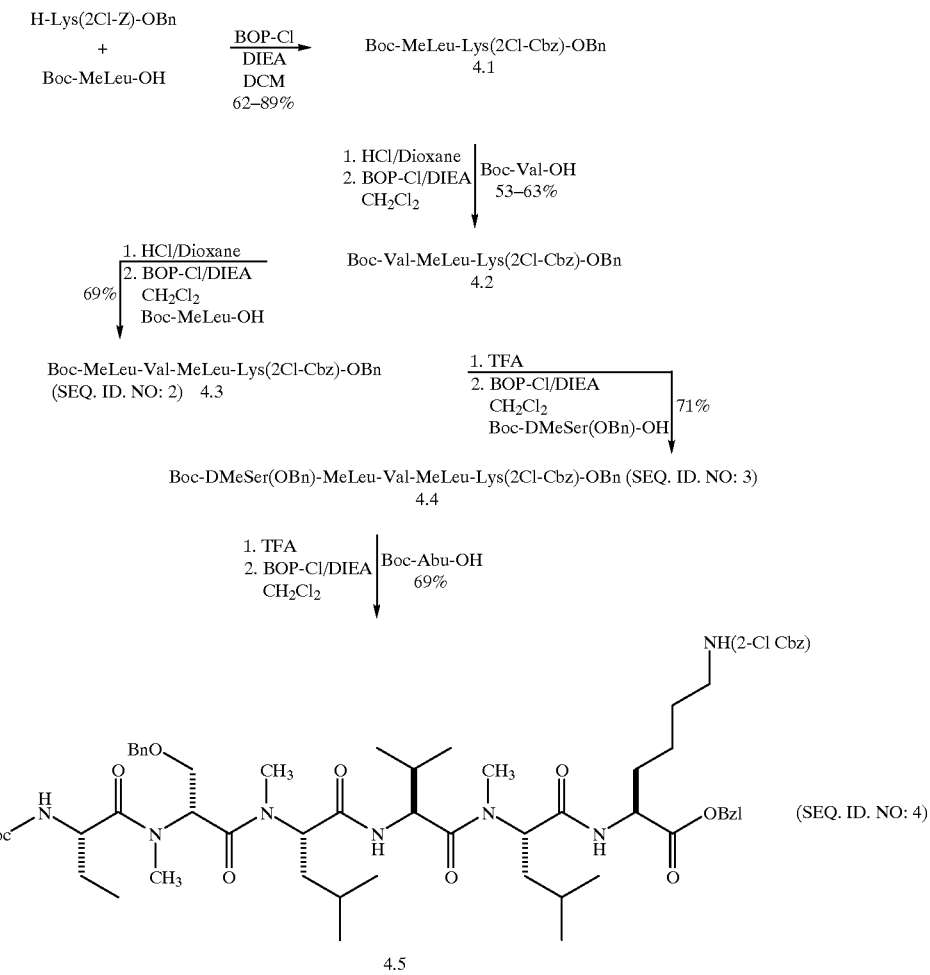

4.5

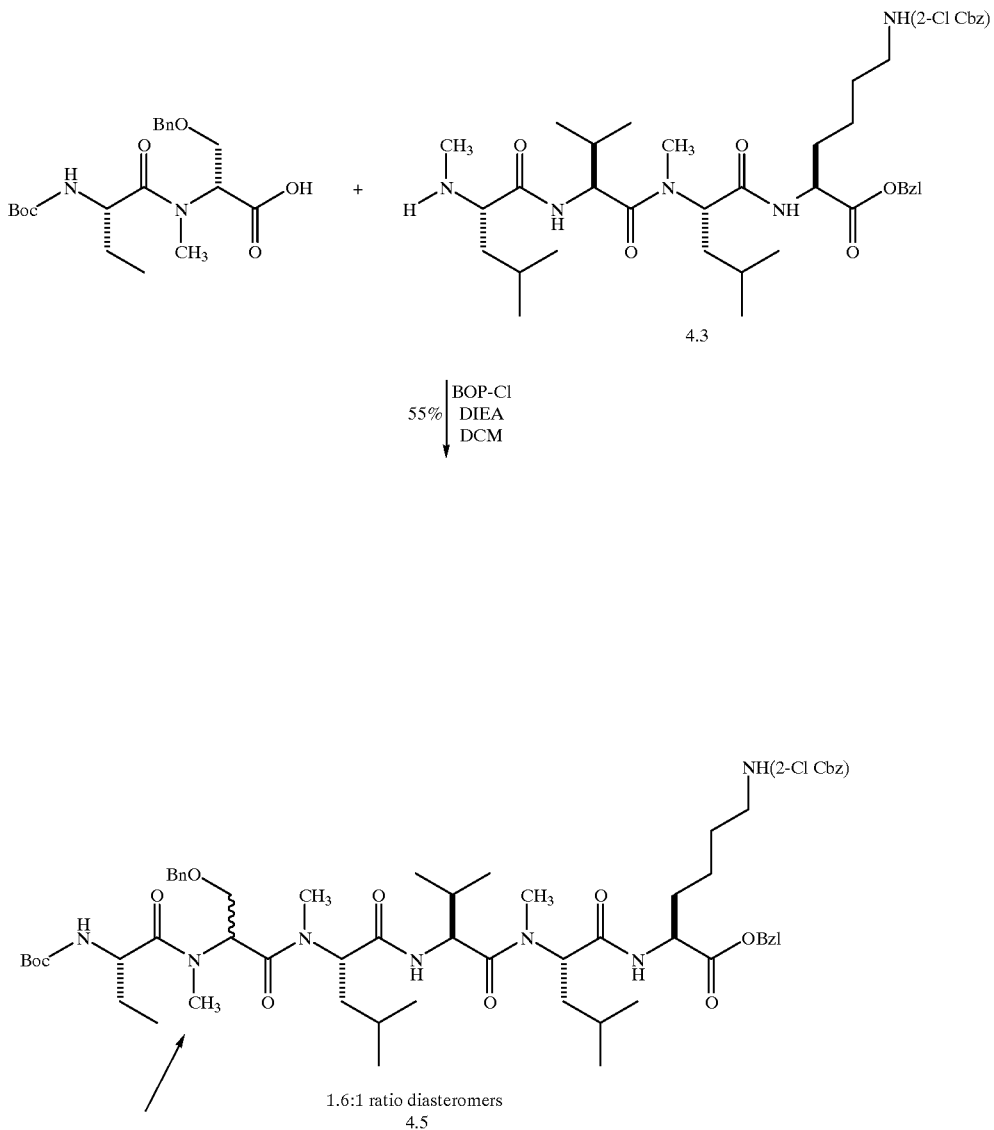
Scheme 4.2
Epimerization of DMeSer (OBn)₃ in "4 + 2" coupling.

Scheme 4.3
Synthesis of undecapeptide 4.9 precursor of [MeLeu(3-OH)¹, DMeSer(OBn)³, Lys(2Cl-Cbz)⁷] CsA.

Completion of CsA Analog:

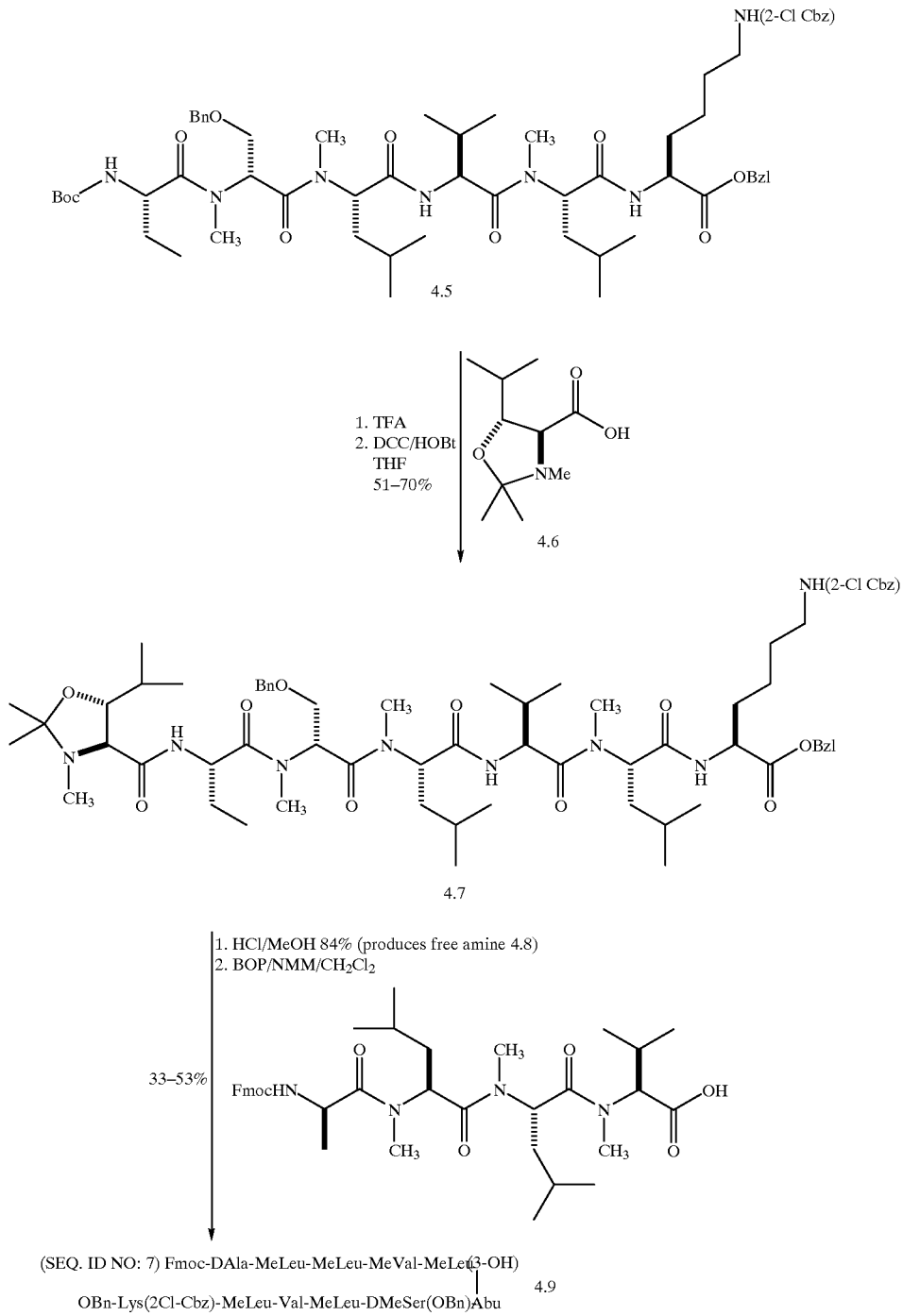

The final Stages of the CsA analog synthesis follows the procedure first developed by Wenger, supra. The 2–7 hexapeptide 4.5 is coupled to the acetonide- protected MeLeu(3-OH) 4.6 with EDCI/HOBt to yield the 1–7 heptapeptide 4.7 in yields of 51–70% (Scheme 4.3). Cleavage of the acetonide with standard HCl(aq) conditions and neutralization of the HCl salt with NaHCO₃ gives 4.8, which is coupled to the 8–11 tetrapeptide with the BOP reagent to produce the undecapeptide 4.9 in 33–53% yield. Simultaneous cleavage of the Fmoc and benzyl ester groups with NaOH(aq)/ethanol followed by cyclization of the linear undecapeptide with DMAP/Propyl phosphonic anydride in CH$_2$Cl$_2$ gives (MeLeu(3-OH)$^1$, D-MeSer(OBn)$^3$, Lys(2Cl-Cbz))CsA 4.10 in fair to good yields of 30–60% (Scheme 4.4).

Scheme 4.4
Undecaptide cyclization to form [MeLeu(3-OH)$^1$, (D)MeSer(OBn)$^3$, Lys(2Cl-Cbz)$^7$] CsA 4.10.

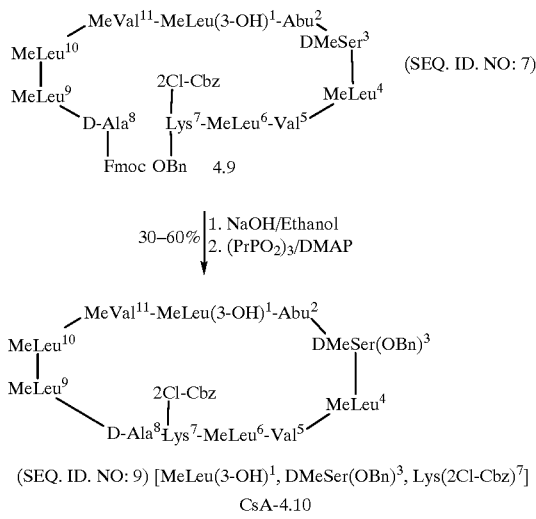

(SEQ. ID. NO: 9) [MeLeu(3-OH)$^1$, DMeSer(OBn)$^3$, Lys(2Cl-Cbz)$^7$] CsA-4.10

Scheme 4.6.
Synthesis of 3-7 pentapeptide 4.14 precursor of [MeLeu(3-OH)$^1$, DMeSer(OH)$^3$, Lys(2Cl-Cbz)$^7$]CsA.
Synthesis of (MeLeu(3-OH)$^1$, D-MeSer(OH)$^3$, Lys(2Cl-Cbz)$^7$)CsA:

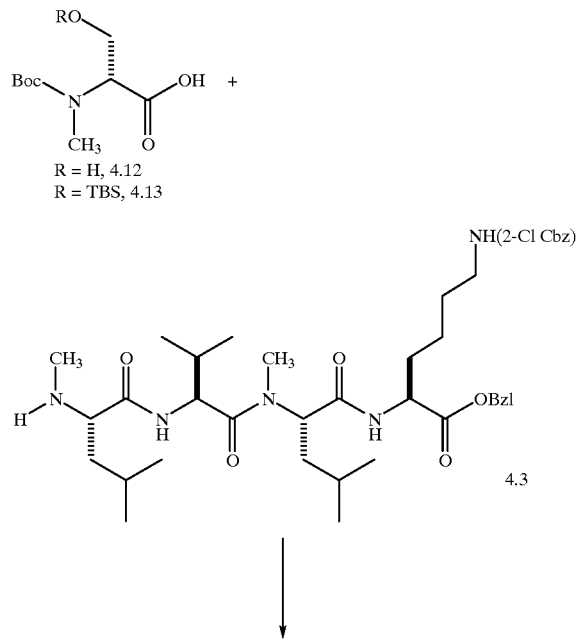

-continued

Scheme 4.6.
Synthesis of 3-7 pentapeptide 4.14 precursor of [MeLeu(3-OH)$^1$, DMeSer(OH)$^3$, Lys(2Cl-Cbz)$^7$]CsA.
Synthesis of (MeLeu(3-OH)$^1$, D-MeSer(OH)$^3$, Lys(2Cl-Cbz)$^7$)CsA:

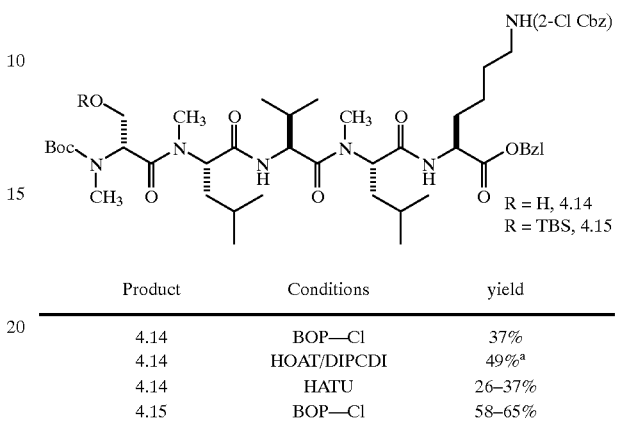

R = H, 4.14
R = TBS, 4.15

| Product | Conditions | yield |
|---------|------------|-------|
| 4.14 | BOP—Cl | 37% |
| 4.14 | HOAT/DIPCDI | 49%$^a$ |
| 4.14 | HATU | 26–37% |
| 4.15 | BOP—Cl | 58–65% |

$^a$product contaminated with urea formed during the reaction

The Boc group is cleaved from tetrapeptide 4.3, and the resulting free amine HCl salt is coupled to Boc-D-MeSer-OH 4.12 with BOP-Cl, to give the desired pentapeptide 4.14 (Scheme 4.6). Other coupling reagents, such as HATU or DIPCDI/HOAT can also be used (Scheme 4.6). Temporary hydroxyl protection, which is cleaved after pentapeptide formation, improves the yield of product and the ease of purification. To this end, Boc-D-MeSer(OTBS-OH 4.13 is smoothly coupled to the tetrapeptide 4.3 with BOP-Cl to give pentapeptide 4.15 in 65% yield (Scheme 4.6). The TBS group was cleaved from pentapeptide 4.15 with TBAF/THF in 70% yield, or with mild HF/pyridine treatment in 90% yield to give 4.24 (Scheme 4.7). Removal of the Boc group from pentapeptide 4.14 with TFA, followed by neutrlization of the TFA salt with NaHCO$_3$, gives a free amine which is coupled with Boc-Abu-OH to give the desired hexapeptide 4.16 in 68% yield.

The Boc group is removed from hexapeptide 4.16, neutralized, and coupled with the acetonide-protected MeLeu(3-OH) 4.6 to give heptapeptide 4.17 in 58–80% yield. Acetonide-protected MeLeu(3OH) is formed by refluxing MeLeu(3-OH) in acetone overnight. Cleavage of the acetonide from heptapeptide 4.17 with HCl/MeOH, followed by neutralization with NaHCO$_3$, gives the heptapeptide amine 4.18 in 58–80% yield. The heptapeptide 4.17 is then coupled with 8-11 tetrapeptide under standard conditions to give undecapeptide 4.19 in 32–50% yield (Scheme 4.8). After cyclization of the undecapeptide 4.19 with (PrPO$_2$)$_3$/DMAP, the CsA analog [MeLeu(3-OH)$^1$.D-MeSer(OH)$^3$,Lys(2Cl-Cbz)$^7$CsA 4.20 is obtained in 41–53% yield. To allow coupling of the HIV protease inhibitor or another compound to the CsA analog, the Cbz group is cleaved with Pd(OH)$_2$/H$_2$ to yield the desired free amine CsA analog 4.11 in quantitative yield.

Scheme 4.7
Synthesis of 1–7 heptapeptide 4.18 precursor of [MeLeu(3-OH)$^1$, DMeSer(OH)$^3$, Lys(2Cl-Cbz)$^7$] CsA.
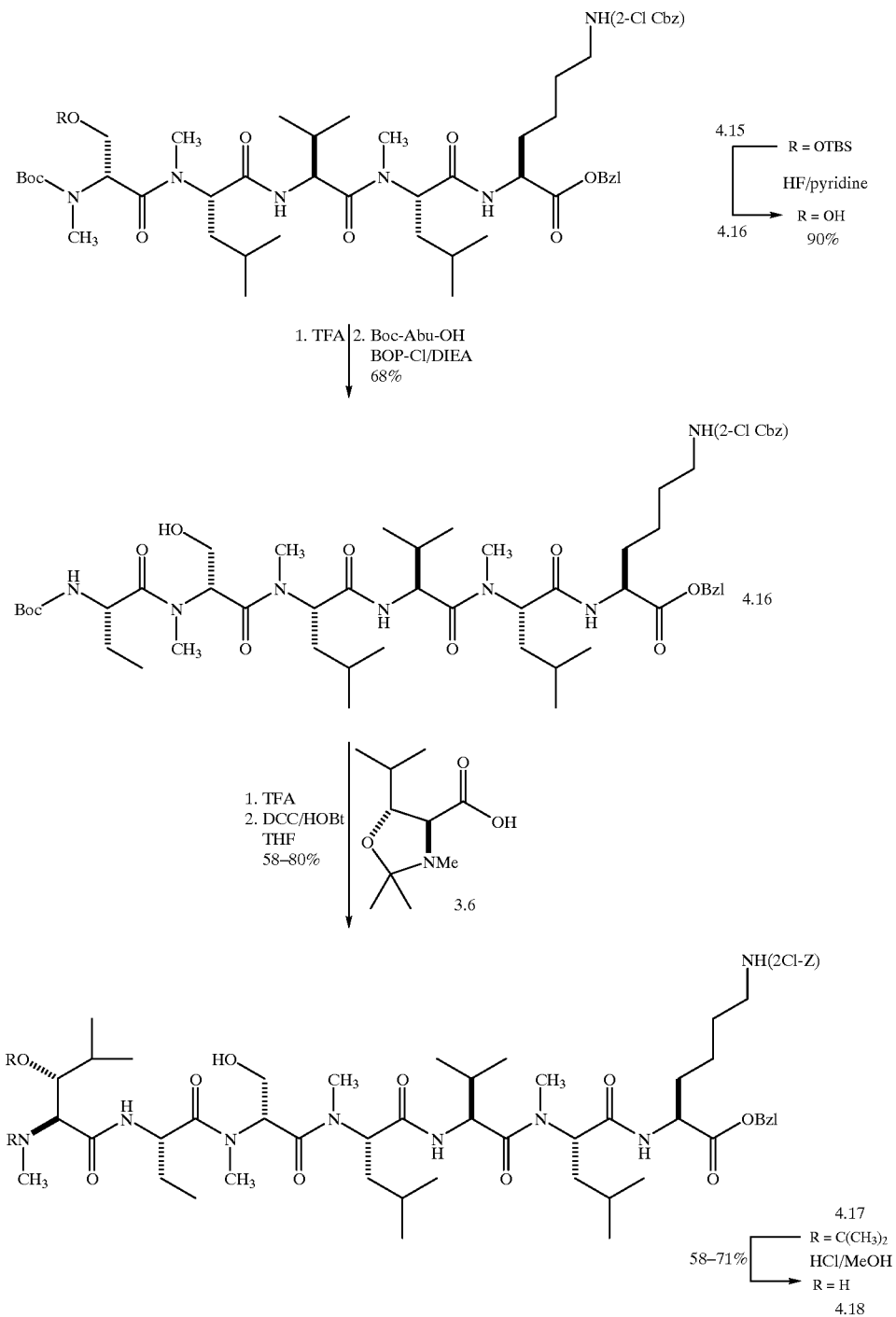

Scheme 4.8
Synthesis of [MeLeu(3-OH)¹, DMeSer(OH)³, Lys⁷] CsA 4.11.

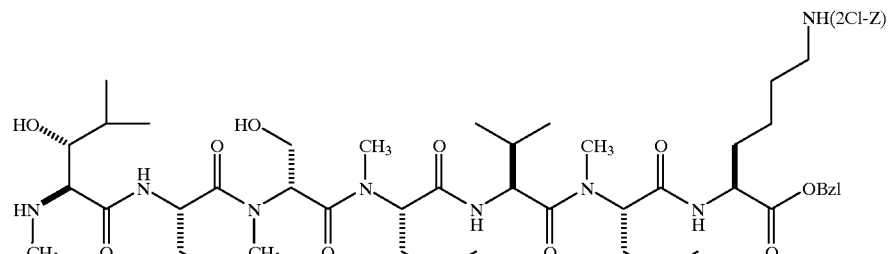

4.18

↓ 32–50% | BOP/NMM/CH₂Cl₂
Fmoc-DAla-MeLeu-MeLeu-MeVal-OH

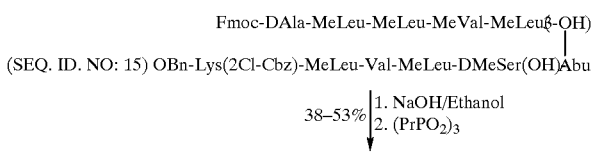

Fmoc-DAla-MeLeu-MeLeu-MeVal-MeLeu(β-OH)
(SEQ. ID. NO: 15) OBn-Lys(2Cl-Cbz)-MeLeu-Val-MeLeu-DMeSer(OH)Abu ↓ 38–53% | 1. NaOH/Ethanol
2. (PrPO₂)₃

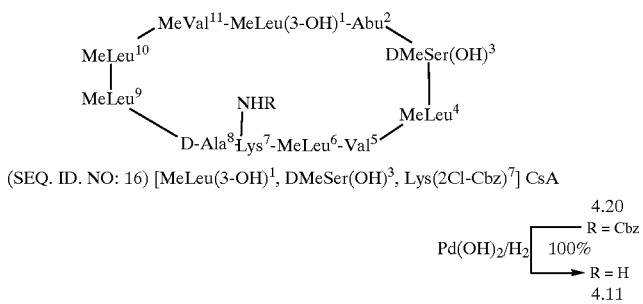

(SEQ. ID. NO: 16) [MeLeu(3-OH)¹, DMeSer(OH)³, Lys(2Cl-Cbz)⁷] CsA 4.20 R = Cbz
Pd(OH)₂/H₂ 100%
R = H
4.11

Synthesis of η-Hydroxycyclosporin A (OL-17) from CsA:

The semisynthetic cyclosporin A derivative, OL-17 is synthesized by the procedure of Eberle and Nuninger (1992), *J. Org. Chem.* 57:2689 (Schnem 4.9). Cyclosporin A is treated with acetylchloride and DMAP to yield acetylcyclosporin A 4.21 in 65% yield. Allylic bromination with 1.2 equivalent of NBS.AIBN(cat.) in CCl₄ at reflux gives allylic bromide 4.22 which is used crude in the next reaction. As noted by Eberle and Nuninger, the bromination reaction cannot be followed by TLC because the starting material and product have identical R$_f$ values. Thus, crude allylic bromide 4.22 is dissolved in 2-butanone, treated with NMe₄OAc/cat.NaI, and the reaction is heated to 60° C. to give η-acetoxyacetyl cyclosporin A 4.23 in 47% yield after purification by flash chromatography. The bisacetate 4.23 is treated with to NaOMe to give the final product, OL-17 2.11 in 50% yield.

Scheme 4.9
Synthesis of OL-17 2.11

[Structure: CsA with MeBmt¹ highlighted]

DMAP, Ac₂O, 65% →

[Structure 4.21]

NBS / AIBN →

[Structure 4.22 with Br]

NMe₄OAc, 2-Butanone, cat. NaI, 2 steps: 47% →

[Structure 4.23 with OAc groups]

NaOMe, 50% →

[Structure 2.11]

Design of Cyclophilin/FKBP-Amyloid Aggregation Inhibitors

The working hypothesis driving construction of the subject conjugates was that inhibition of fibril formation and/or prevention of plaque growth might be enhanced by recruiting an endogenous protein to bind to the Aβ peptide(s), thereby functioning similarly to ApoE, a protein which inhibits amyloid aggregation. See Evans et al. (1995) *J. Proc. Natl. Acad. Sci. U.S.A.* 92:763. Cyclophilin (CyP), a ubiquitous protein which is present at high concentrations and in many cell types, binds to Cyclosporin A (CsA) and the dimeric complex binds to calcineurin (as noted above). Modification of the calcineurin binding domain or "effector domain" leads to CsA analogs that retain binding to cyclophilin but no longer bind calcineurin. Consequently, it was reasoned, residues 16–20 of Aβ could be attached to a suitable CsA analog to produce a compound which binds both Aβ and Cyp simultaneously.

Analogously, examination of a small molecule FKBP inhibitor complexed with FKBP suggested that conjugation of a peptide which binds to Aβ to an appropriately functionalized small molecule FKBP inhibitor should also produce a simultaneous binder/inhibitor of FKBP and the Aβ peptide(s).

CsA Analog/Amyloid Aggregation Inhibitors:

[MeLeu(3-OH)¹, MeAla⁴,⁶, Lys⁷]-CsA 10.1 (Scheme 10.1) was selected as the cyclophilin binder. [MeLeu(3-OH)¹, MeAla⁴,⁶]-CsA is non-immunosuppressive and retains tight-binding to cyclophilin. While not being held to any particular biological mechanism, it is believed that cyclophilin readily binds to a CsA-KLVFF molecule to form a soluble complex which is then free to interact with the Aβ peptide (via the KLVFF (SEQ. ID. NO: 25) moity) thereby preventing and/or inhibiting Aβ nucleation and/or deposition. Furthermore, it is believed that the the 20 Kda cyclophilin/CsA-KLVFF (SEQ. ID. NO: 25) complex interacts with existing plaques, thereby altering the solubility characteristics of the plaques.

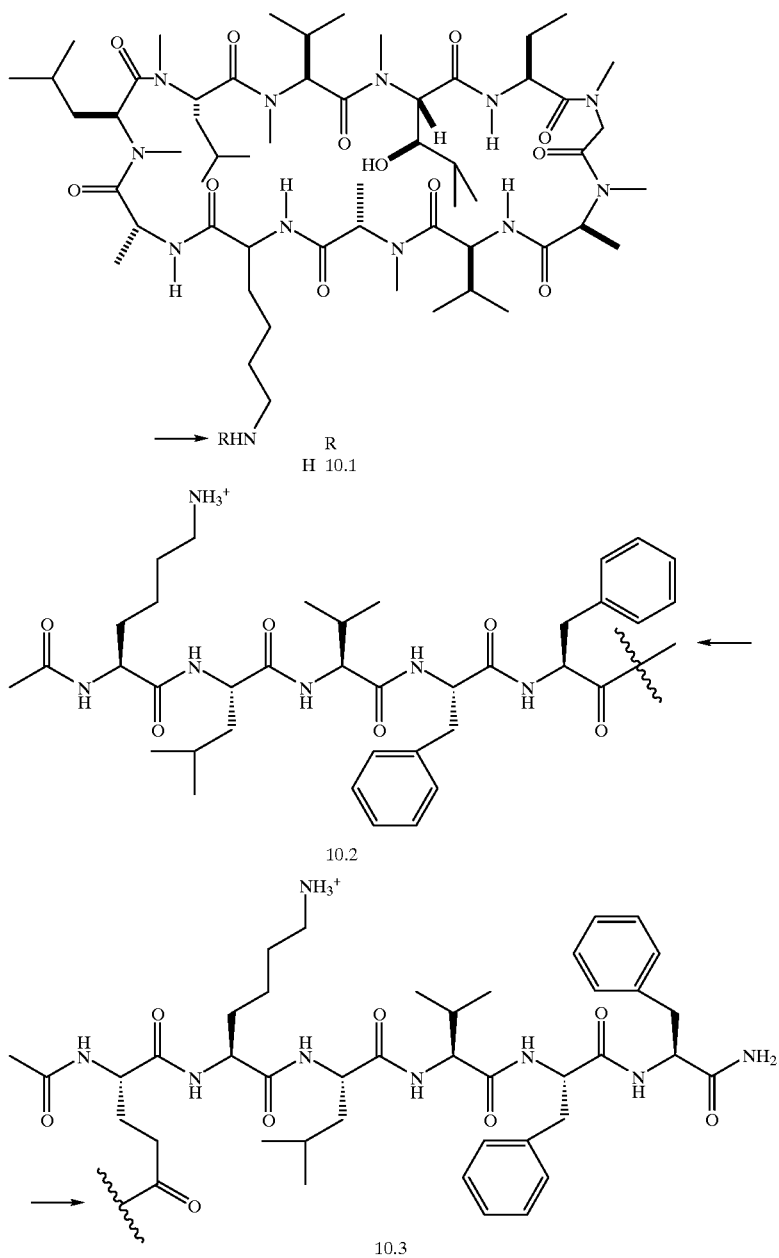

Figure 10.1. CsA Analog/Aβ-binding-peptide conjugates 10.2 & 10.3. The arrows indicate where the CsA analog and the peptide are attached.

The site the peptide is attached to the CsA analog may be varied. The first amyloid aggregation inhibitor 10.2 was designed to attach the C-terminal acid of the Aβ-binding-peptide (Aβ residues 16–20) to the Lys[7] side chain of the CsA analog (Fig. 10.1). Modeling of the CsA analog/Cyp complex with the Aβ-binding-peptide Ac-KLVFF assumed to adopt a β-sheet conformation, shows that the peptide extends from the CsA/Cyp complex and should have the ability to interact with the Aβ peptide or plaque. The second conjugate 10.3 was designed to incorporate Ac-EKLVFF-NH₂ (SEQ. ID. NO: 27) by attaching the glutamic acid side chain of the peptide to the Lys[7] side chain of the CsA analog 10.1. Since amide bond formation between the N-terminus glutamic acid side chain and the CsA lysine side chain produces a carboxamide, it mimics the glutamine residue present at the same position in the Aβ peptide. Additionally, the Aβ-binding-peptide in conjugate 10.3 is perpendicular to the CsA/Cyp complex, which may have an affect on its ability to inhibit aggregation or deposition of Aβ peptide.

FKBP Inhibitor/Amyloid Aggregation Inhibitors:

The design and synthesis of small molecule FKBP inhibitors 10.4 and 10.3 based on the ketoamide moiety in FK506 has been reported (Scheme 10.4). See Holt et al. (1993) *J. Am. Chem. Soc.* 115:9925.

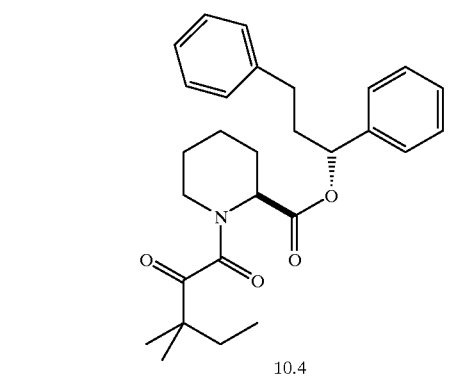

10.4

$K_i(FKBP) = 10nM$

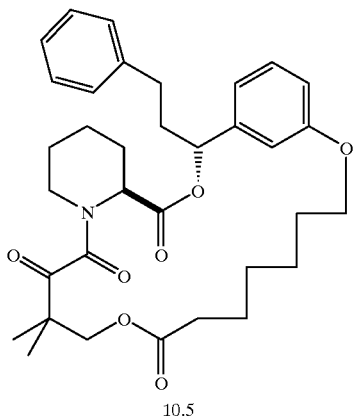

10.5

$K_i(FKBP) = 1nM$

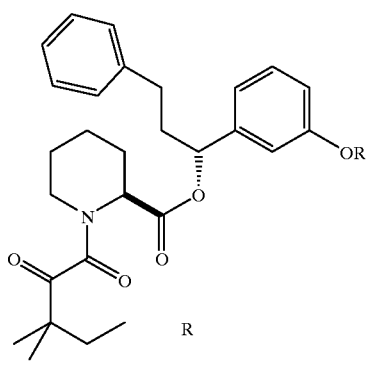

R

CH₂CO₂H 10.6
CH₂(CH₂)₄CO₂H 10.7

Figure 10.4. Reported FKBP inhibitors 10.4 and 10.5. FKBP inhibitors 10.6 & 10.7 were designed to contain a carboylic acid group for coupling to the Aβ-binding-peptides. FKBP is another ubiquitous PPIase enzyme that is also useful in the design of an amyloid aggregation "complexes " similar to the cyclopilin/CsA-Aβ binding peptide system. Inspection of the crystal structure of 10.4 complexed with FKBP indicated that an Aβ-binding peptide could be attached to the meta position of the phenyl group (points toward solvent) in 10.4 without creating unfavorable interactions with FKBP. Additionally, the reported constrained inhibitor 10.5 establishes that the meta position of the phenyl group can be modified without disturbing its binding to FKBP. Thus, the phenyl meta position was functionalized to give compounds 10.6 and 10.7 which contain carboxylic acid groups as attachment sites for the Aβ-binding peptides.

Conjugate 10.8 was designed to incorporate a meta substituted acetoxy acid linker attached to the lysine side chain of the peptide pyridyl acetyl-KLVFF-NH₂ (SEQ. ID. NO:) (Scheme 10.6). The N-terminus pyridyl acetyl had to be used in conjugate 10.8 because the N-acetyl peptides were insoluble. Molecular modeling of conjugate 10.8 with FKBP indicates that no unfavorable interactions between the Aβ-binding-peptide and FKBP should occur. A second FKBP inhibitor/Aβ-peptide-conjugate 10.9 was designed by attaching the C-terminus lysine side chain of pyridyl acetyl-K(alloc)LVFKK-NH₂ (SEQ. ID. NO: 31) to the carboxylic acid of FKBP inhibitor 10.10 which contains a 6 carbon linker (Scheme 10.9).

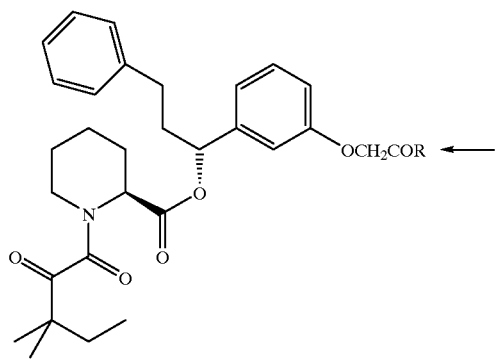

R

-continued
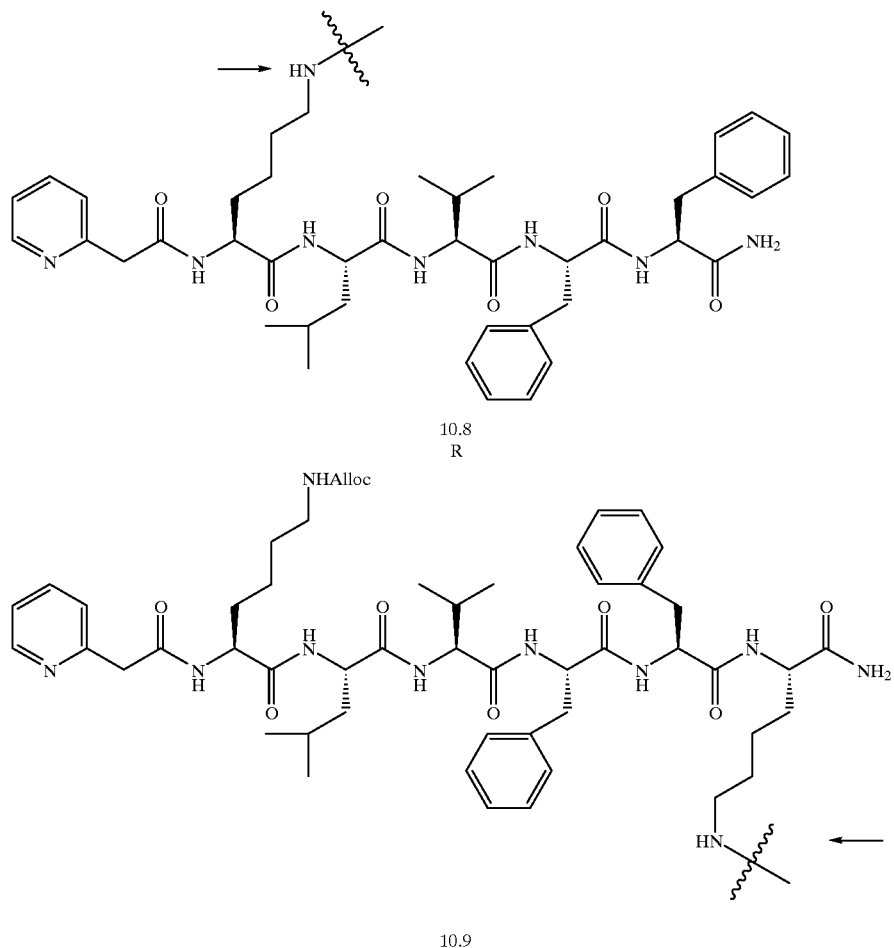
Figure 10.6. FKBP inhibitor (acetoxy)/Aβ-binding-peptide conjugates 10.8 & 10.9. The arrows indicate where the inhibitor and peptide are attached.
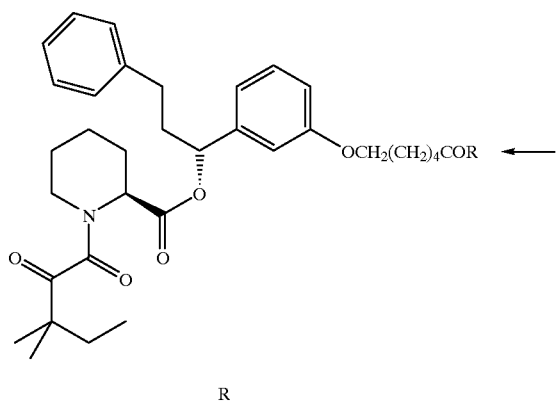

-continued

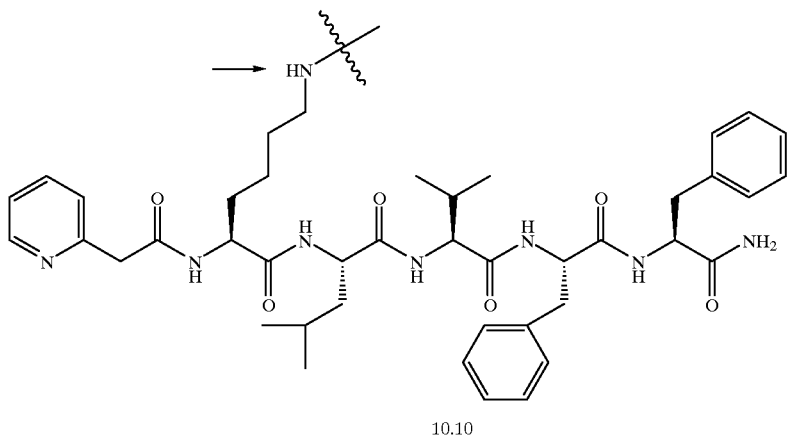

10.10

Figure 10.9. FKBP inhibitor (oxo-hexanoate)/Aβ-binding-peptide conjugate 10.10, which contain a 6 carbon linker. The arrows indicate where the inhibitor and peptide are attached.

Synthesis of [MeLeu(3-OH)[1], MeAla[4,6], Lys(2Cl-Cbz)[7]] CsA

The synthesis of the CsA analog 10.1 followed the modified Wenger procedure described above (see Scheme 4. 1). Coupling of Boc-MeAla-OH to H-Lys(2Cl-Cbz)-OBn with BOP-Cl proceeds smoothly to yield dipeptide 11.1 in 80–86% yield (Scheme 11.1). The Boc group in 11.1 was cleaved with HCl/Dioxane to give the free amine HCl salt, which was reacted with Boc-Val-OH to give the tripeptide 11.2 in 56–63%. Deprotection of 11.2 and coupling of the free amine HCl salt to Boc-MeAla-OH produced the 4–7 tetrapeptide 11.3 in 43–41% yield. Hexapeptide 11.4 was formed in 55–89% yield by reaction of tetrapeptide 11.3 with TFA to cleave the Boc group, neutralization with NaHCO$_3$ followed by coupling to Boc-Abu-Sar-OH under the conditions noted above.

Scheme 11.1
Synthesis of hexapeptide 2–7 11.4 precursor of [MeLeu(3-OH)[1], MeAla[4,6], Lys(2Cl-Cbz)[7]] CsA.

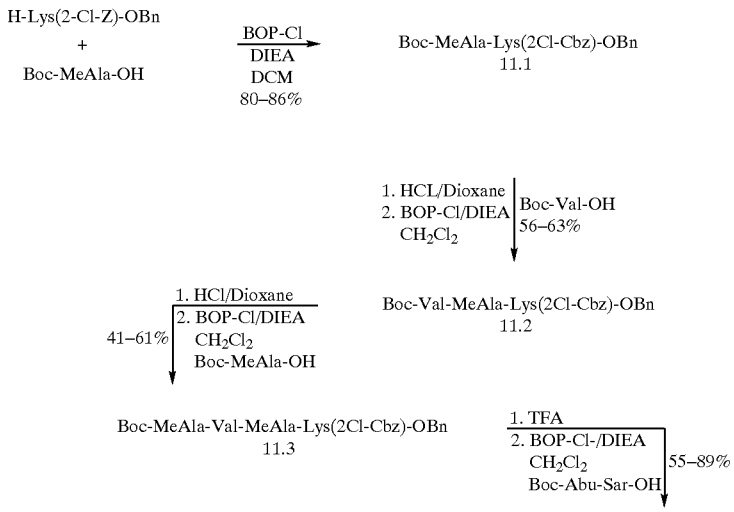

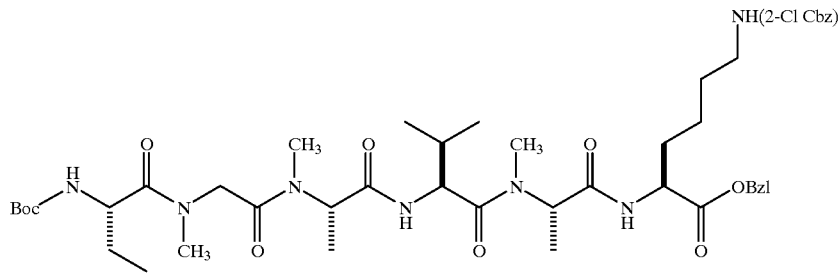

11.4

The final stages of the CsA analog synthesis followed the procedure reported by Wenger. The 2–7 hexapeptide 11.4 was treated with TFA to cleave the Boc group and neutralized with NaHCO$_3$ to give the free amine hexapeptide, which was coupled to acteonide-protected MeLeu(3-OH) 4.6 with DCC/HOBt to form the 1–7 heptapeptide 11.5 in 67% yield (Scheme 11.2). Cleavage of the acetonide in 11.5 under standard HCl(aq) conditions gives the free amine 11.6 which was coupled to the 8–11 tetrapeptide with the BOP reagent to produce the undecapeptide 11.7 in 32–59% yield. Simultaneous cleavage of the Fmoc and benzyl ester protecting groups with NaOH (aq)/ethanol, and subsequent cyclization of the fully deprotected undercapeptide with DMAP/Propyl phosphoric anhydride in DCM gives [MeLAu(3OH)[1], MeAla[4,6], Lys(2Cl-Cbz)[7]] CsA 11.8 in 63–75% yield (Scheme 11.3). Quantitative cleavage of the Cbz group was accomplished by hydrogenation over Pd(OH)$_2$ to yield 10.1.

Scheme 11.2
Synthesis of undecapeptide 11.7 precursor of [MeLeu(3-OH)[1], MeAla[4,6], Lys(2Cl-Cbz)[7]] CsA.

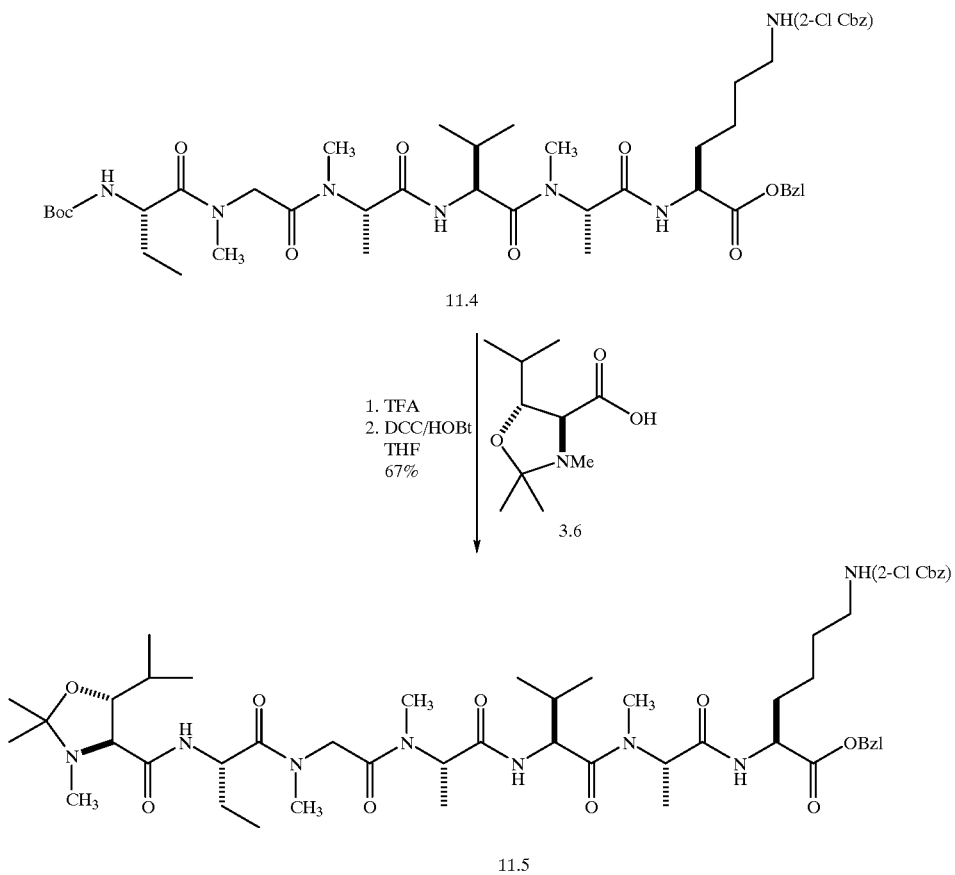

-continued

1. HCl/MeOH 63–84% (produces free amine 11.6)
2. BOP/NMM/CH$_2$Cl$_2$

32–59%

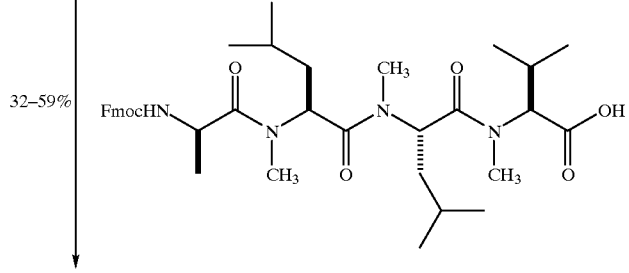

Fmoc-DAla-MeLeu-MeVal-MeLeu(3-OH)
|
OBn-Lys(2Cl-Cbz)-MeAla-Val-MeAla-Sar-Abu 11.7

Scheme 11.3
Cyclization of undecapeptide to form [MeLeu(3-OH)$^1$, MeAla$^{4,6}$, Lys(2Cl-Cbz)$^7$] CsA 11.8 and cleavage of 2Cl-Cbz group to form 10.1.

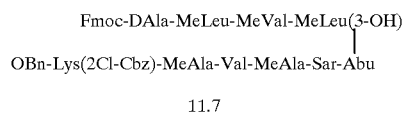

11.7(SEQ. ID. NO.: 32)

63–75% | 1. NaOH/Ethanol
2. (PrPO$_2$)$_3$/DMAP

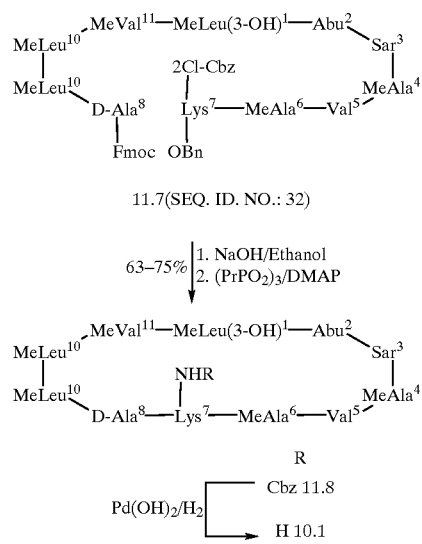

Synthesis of FKBP Inhibitors:

The synthesis of the FKBP inhibitors followed the procedure of Holt et al., supra (see Scheme 11.4). Reacting hydroxybenzaldehyde 11.9 with phenethylmagnesium chloride gives the secondary benzylic alcohol 11.10 in 72% yield. Alcohol 11.10 is oxidized with the Jones Reagent to give the ketone 11.11 in 56% yield which is then reacted with acetic anhydride to produce acetate 11.12 in 84% yield. Ketone 11.12 is enantioselectively reduced by using Brown's β-(+)-chlorodiisopinocampheylborane method to give the R-alcohol 11.13 in 88% yield which is hydrolyzed with Na$_2$CO$_3$ to give phenol 11.14 in 72% yield. The stereochemical assignment of alcohol 11.14 is based on well-established precedent. Selective alkylation of the phenol over the alcohol in 11.14 is accomplished by reaction of 11.14 with Cs$_2$CO$_3$ and the appropriate alkyl halide to produce esters 11.15 and 11.16 in excellent yields (Scheme 11.5). 1-Bromo allylhexanoate, the long-chain alkyl halide, is derived from treatment of bromohexanoic acid in allyl alcohol with TMS-Cl.

Scheme 11.4
Synthesis of R-Benzylic Alcohol 11.14.

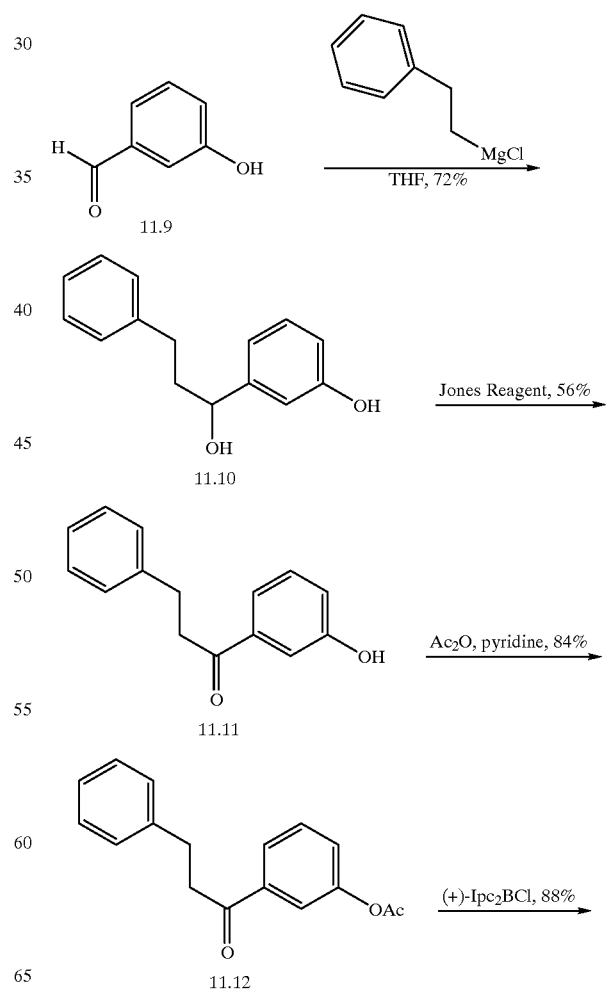

-continued

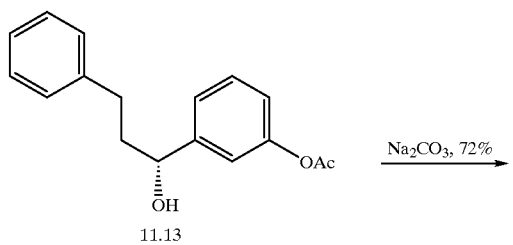

11.13

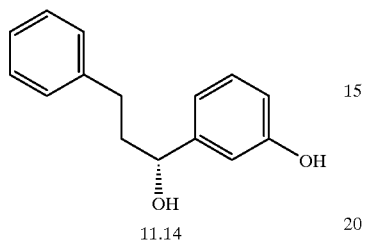

11.14

---

Scheme 11.5.
Attachment of linker functionality to benzylic alcohol 11.14.

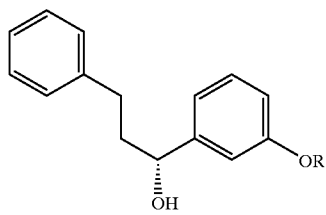

| "Reagent" | X |
|---|---|
| 1. ClCH$_2$CO$_2$tBu | CH$_2$CO$_2$tBu, 95% 11.15 |
| 2. BrCH$_2$(CH$_2$)$_4$CO$_2$Allyl | CH$_2$(CH$_2$)$_4$CO$_2$Allyl, 86% 11.16 |

---

Scheme 11.6
Synthesis of FKBP inhibitor pipecolic keto amide acid 11.20.

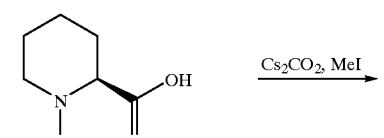

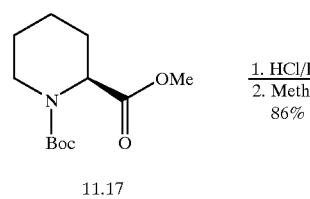

11.17

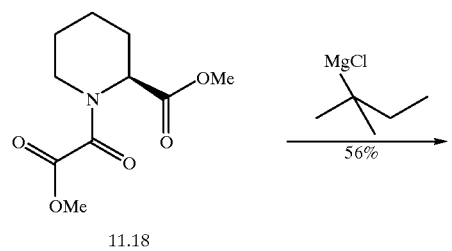

11.18

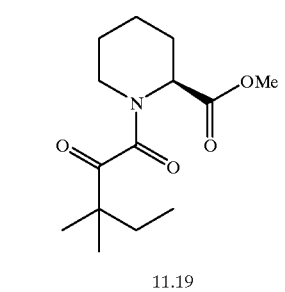

11.19

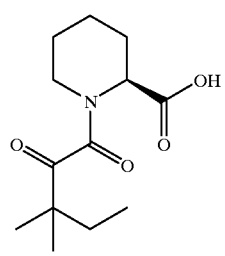

11.20

---

The pipecolic ketoamide derivative is synthesized in 5 steps from L-Boc-Pip-OH (see Scheme 11.6). Boc-Pip-OH is reacted with Cs$_2$CO$_3$ MeI to give the methyl ester 11.17 which is used crude in the next reaction. The Boc group is cleaved with HCl/dioxane to form the HCl-Pip-OMe salt, which is reacted with methyl oxalyl chloride to give methyl oxamate 11.18 in 86% overall yield. Selective addition to the ketoamide ester in 11.18 with 1,1-dimethylpentylmagnesium chloride produced the ketoamide 11.19 in 56% yield. Methyl ester 11.19 is hydrolyzed with LiOH to acid 11.20 which is coupled with alcohol 11.15 or 11.16 with DCC and DMAP to give the FKBP inhibitors 11.21 and 11.22 in good yields (Scheme 11.7). Ester deprotection (to give the carboxyl group for linking to the Aβ binding peptide) is accomplished by either reaction of 11.21 with TFA to yield the acid 11.6 or reaction of allyl ester 11.22 with Pd(0) and morpholine to produce acid 11.7. Both 11.6 and 11.7 are used crude in the coupling reactions with the Aβ-binding-peptides.

Scheme 11.7.
Synthesis of small molecule FKBP inhibitor acids 10.6 & 10.7.

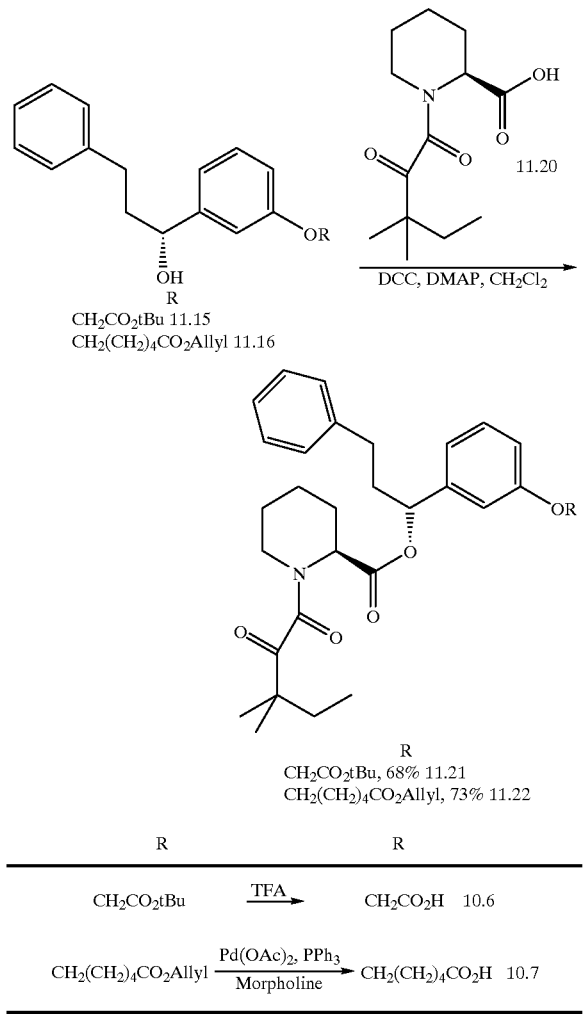

Synthesis of Aβ-Binding Peptide/CsA and Aβ-Binding Peptide/FKBP Inhibitor Conjugates:

The synthesis of Aβ-binding peptides is accomplished by conventional solid phase synthesis using N-Fmoc-protected amino acids. The HMPB linker is used for the synthesis of C-terminal acids and the PAL resin is used for the synthesis of C-terminal amides. 2Cl-Cbz is chosen for the nitrogen epsilon side chain protection since it can be cleaved after conjugate formation to produce the final product free amine. EDCI/HOBt is used as the coupling reagent and acetylimidazole is used as the capping reagent. After cleavage from the resin with TFA, the solubles of the crude peptides were determined (ca. 3–5 mg/0.5–1.0 ml) in various solvents (LiCl/DMF, DMF or NMP, and/or mixtures with DCM/MeOH/CH$_3$CN/dioxane). Without furiher purification (due to the insolubility of the peptides), the crude peptides are coupled with the CsA analog in the appropriate solvent system.

Solubility of the Aβ-binding peptides is problematic, as is expected for these types of structures. The first peptides synthesized were based upon QKLVFF-NH$_2$ (SEQ. ID. NO: 24) and were not soluble in 5–10 mM DMF/LiCl and could not be coupled to the CsA analog. To increase die Aβ-binding peptide's solubility, truncated peptides based on the sequence KLVFF (SEQ. ID. NO: 25) were prepared. Both Ac-K(2Cl-Cbz)LVFF-OH (SEQ. ID. NO: 26) and Ac-EK(2Cl-Cbz)LVFF-NH$_2$ (SEQ. ID. NO: 27) were found to contain increased solubility in DMF. N-Fmoc-protected peptides of the same KLVFF sequences were synthesized as test cases and were found to have greater solubility in DMF than their acetyl analogs. Although the acetyl analogs display less solubility than Fmoc analogs, Ac-K(2Cl-Cbz) LVFF (SEQ. ID. NO: 26) and Ac-EKLVFF-NH$_2$ (SEQ. ID. NO: 27) could be coupled to the CsA analogs to give the conjugates which could be hydrogenated to produce the free amine compounds for testing.

Synthesis of Aβ-Binding Peptides for CsA Analog/Aβ-Binding Peptide Conjugates

The first step towards synthesizing the desired conjugates is to find Aβ-binding peptides that are soluble enough in organic solvents to undergo coupling reactions with CsA analog (see Table. 11.1):

TABLE 11.1

| Peptide | | | Solubility[a,b,c] |
|---|---|---|---|
| Ac-QK(2Cl-Cbz)LVFF-OH | 11.23 | | medium in LiCl/DMF or LiCl/NMP |
| Ac-Q(Trt)K(2Cl-Cbz)LVFF-OH | 11.24 | SEQ ID NO:24 | medium in LiCl/DMF or LiCl/NMP |
| Fmoc-Q(Trt)K(2Cl-Cbz)LVFF-OH | 11.25 | SEQ ID NO:24 | Hot NMP |
| Fmoc-K(2Cl-Cbz)LVFF-OH | 11.26 | SEQ ID NO:25 | DMF |
| Ac-K(2Cl-Cbz)LVFF-OH | 11.27 | SEQ ID NO:26 | DMF |
| Fmoc-EK(2Cl-Cbz)LVFF-NH$_2$ | 11.28 | SEQ ID NO:27 | DMF |
| Ac-EK(2Cl-Cbz)LVFF-NH$_2$ | 11.29 | SEQ ID NO:27 | LiCl/DMF |

The first peptide synthesized, Ac-QK(2Cl-Cbz)LVFF-OH (SEQ. ID. NO: 24) 11.23 was chosen based on the work of Tjernberg et al. (1996) *J. Biol. Chem.* 271:8545, who reported that Ac-QKLVFF-NH$_2$ binds to and inhibits fibril formation. However, this peptide is poorly soluble in all solvents including LiCl/DMF (normally the best solubilizing solvent). Reaction of 11.23 with the CsA analog 10.1 in LiCl/DMF was attempted using BOP but no product could be isolated. See Table 11.2. A related peptide 11.24 which has the side chain of glutamine protected as the trityl derivative was synthesized in order to improve the solubility of the compound in DMF/LiCl. Peptides with glutamine residues often have insolubility problems which can be overcome by protecting the carboxamide side chain with a trityl group. However, no improvement in solubility is observed. Next, peptide 11.25, which contains N-Fmoc protection in addition to a trityl-protected glutamine side chain, was synthesized and found to be soluble in only hot NMP and remained cloudy in LiCl/DMF.

In order to overcome the solubility and coupling problems of the QKLVFF-type peptides, truncated peptides without the N-terminal glutamine were synthesized. A general solubility pattern in DMF or NMP is observed: peptides with Fmoc on the N-terminus are more soluble than those containing acetyl groups, and peptides derived from KLVFF-OH (SEQ. ID. NO: 24) are more soluble than those derived from EKLVFF-NH$_2$ (SEQ. ID. NO: 30). Fmoc-K(2Cl-Cbz)LVFF-OH 11.26 is completely soluble in DMF after a short period of vortexing. Peptide 11.27, which contains an N-terminal acetyl group, is also soluble in DMF but requires a longer vortexing period to complete subilization. Adding an Fmoc-Glu residue to the N-teminus of K(2Cl-Cbz)LVFF-NH$_2$ results in a hexpapeptide 11.28 which is also soluble in neat DMF without added LiCl. However, replacing the Fmoc with an acetyl group results in decreased solubility as the peptide 11.29 is completely soluble only in LiCl/DMF.

TABLE 11.2

| peptide | conditions | yield of conjugate |
|---|---|---|
| Ac-QK(2Cl-Cbz)LVFF-OH SEQ ID NO:24 11.23 | BOP/DMF/LiCl | no product isolated |
| Fmoc-K(2Cl-Cbz)LVFF-OH SEQ ID NO:25 11.26 | PyAOP/DMF | 65% 11.30 |
| Ac-K(2Cl-Cbz)LVFF-OH SEQ ID NO:26 11.27 | PyAOP/DMF | 75% 11.31 |
| Fmoc-EK(2Cl-Cbz)LVFF-NH$_2$ SEQ ID NO:27 11.28 | PyAOP/DMF | 37% 11.32 |
| Ac-EK(2Cl-Cbz)LVFF-NH$_2$ SEQ ID NO:27 11.29 | PyAOP/DMF/LiCl | 40% 11.33 |

Coupling of Aβ-Binding-Peptides to the CsA Analog:

The efficiency of coupling the Aβ-binding peptides to the CsA analog and the ease of isolation of the product can be roughly correlated to the solubility of the Aβ-binding peptide in DMF; the peptides which are more soluble in DMF generally give better yields of the CsA analog/Aβ-binding peptide conjugates that are easier to purify. Reaction of the CsA analog 10.1 with Ac-QK(2Cl-Cbz)LVFF-OH (11.23 (SEQ ID NO: 24), which is sparingly soluble in LiCl/DMF, results in no isolation of product. This likely reflects the insolubility of the conjugate in the column eluant, DCM/MeOH (Table 11.2). However, reaction of DMF-soluble Fmoc-K(2Cl-Cbz)LVFF-OH 11.26 (SEQ ID NO: 25) with the CsA analog produces a 65% yield of the conjugate 11.30 which is soluble in DCM/MeOH and can be isolated by silica gel chromatography. Coupling of the peptides Ac-K (2Cl-Cbz)LVFF-OH 11.27 and Fmoc-EK(2Cl-Cbz)LVFF-NH$_2$ 11.28 (SEQ ID NO: 27) with the CsA analog gives a 75% and 37% yield of the desired DCM/MEOH soluble conjugates 11.31 and 11.32.

Although Fmoc-EK(2Cl-Cbz)LVFF (SEQ ID NO: 27)-NH$_2$/CsA analog conjugate 11.32 showed some evidence of aggregation, $^1$H NMR's in CDCl$_3$ could be obtained for all three conjugates 11.30, 11.31 and 11.32. Conjugate 11.33, produced in 40% yield by coupling of Ac-Ek(2Cl-Cbz) LVFF-NH$_2$ 11.29 to the CsA analog 10.1 in DMF/LiCl, could be purified by flash chromatography with DCM/MeOH. However, conjugate 11.33 could not be completely dissolved in DCM/MeOH after isolation.

Removal of the Cbz group from peptides 11.31 and 11.33 is achieved by hydrogenation over Pd(OH)$_2$ (Scheme 11.8). Hydrogenation of Ac-KLVFF-NH$_2$/CsA analog conjugate 11.31 with H$_2$/Pd(OH)$_2$ in methanol gave conjugate 10.2. Although it is not completely soluble in methanol, conjugate 11.33 could by hydrogenated as a slurry in methanol to produce free amine 10.3 which is soluble in DCM/MeOH, as opposed to its 2Cl-Cbz derivative.

Scheme 11.8.
Cleavage of 2Cl-Cbz From CsA/Aβ-Binding-Peptide Conjugates 11.31 and 11.33.

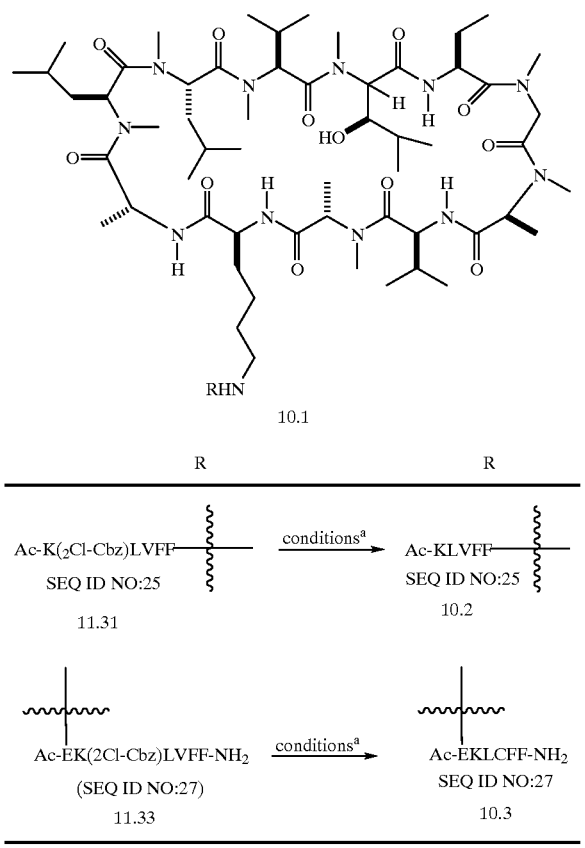

10.1

| R | | R |
|---|---|---|
| Ac-K(2Cl-Cbz)LVFF—<br>SEQ ID NO:25<br>11.31 | conditions[a] → | Ac-KLVFF—<br>SEQ ID NO:25<br>10.2 |
| ↓ | | ↓ |
| Ac-EK(2Cl-Cbz)LVFF-NH₂<br>(SEQ ID NO:27)<br>11.33 | conditions[a] → | Ac-EKLCFF-NH₂<br>SEQ ID NO:27<br>10.3 |

[a]Pd(OH)₂H₂, methanol.

Synthesis of Aβ-Binding Peptides for FKBP Inhibitor/ AβBinding Peptide Conjugates:

The strategy for the FKBP inhibitor/Aβ-binding peptide conjugates is to couple the Aβ-binding peptide lysine epsilon side chain to the carboxyl group of the FKBP inhibitor. Since the FKBP inhibitor portion of the final conjugates contains an ester and a benzyl group, alloc protection as chosen for the epsilon amine of lysine. Palladium-catalyzed cleavage of the alloc group from the final conjugates does not cause any side reactions. However, the insolubility of the conjugates precluded the allyl carbamate cleavage. Thus, the N-terminus of the peptides is capped with a pyridyl acetate group instead of an acetyl or Fmoc group, which allows for salt formation immediately after the conjugates are isolated. The TFA salt form of the conjugates is soluble in methanol.

The solubility characteristics of the peptides with all free amines as the TFA salts are shown in Table 11.3. The first peptide synthesized, Ac-KK(alloc)LVFF-OH SEQ ID NO: 33 11.34 is not completely soluble in any solvent including LiCl/DMF. Peptide 11.35, which contains an Fmoc group on the N-terminus instead of the acelyl group, is also insoluble in DMF/LiCl. However, moving the N-terminal lysine to the C-terminus has a significant affect on the peptide solubility since Fmoc-K(alloc)LVFFK-NH₂ SEQ ID NO: 31 11.36 is completely soluble in LiCl/DMF. Similar to peptide 11.24, which contains a C-terminus acid instead of a C-terminal amide, Fmoc-KLVFF-NH₂ 11.37 is completely soluble in DMF. Having an N- free amine also facilitates solubilization since H₂N-K(alloc)LVFF-NH₂ SEQ ID NO: 25 11.38 is the only peptide in the series which is soluble in DCM/MeOH as well as DMF. A pyridyl acetyl (PAc) group is used to cap the N-terminus to improve solubility. PAc-KLVFF-NH₂ 11.39 and PAc-K(alloc)LVFFK-NH₂ 11.40 are completely soluble in DMF as the double TFA salts.

TABLE 11.3

| Peptide | | Solubility[a,b,c,d] |
|---|---|---|
| Ac-KK(Alloc)LVFF-NH₂ | 11.34 SEQ ID. NO:33 | slight LiCl/DMF |
| Fmoc-KK(Alloc)LVFF-NH₂ | 11.35 SEQ ID NO:33 | medium in LiCl/DMF or LiCl/NMP |
| Fmoc-K(Alloc)LVFFK-NH₂ | 11.36 SEQ ID NO:31 | LiCl/DMF |
| Fmoc-KLVFF-NH₂ | 11.37 SEQ ID NO:25 | DMF |
| H₂N-K(2Cl-Cbz)LVFF-NH₂ | 11.38 SEQ ID NO:25 | DCM/MeOH, DMF |
| Pyridylacetate-KLVFF-NH₂ | 11.39 SEQ ID NO:25 | DMF |
| Pyiidylacetate-K(Alloc)LVFFK-NH₂ | 11.40 SEQ ID NO:31 | DMF |

FIG. 11.3. Solubility of Aβ-Binding-Peptides (FKBP Inhibitor).
[a]conditions: 3–5 mg peptide/0.5–1.0 mL.
[b]conditions tested; NMP, DMF, DMF/LiCl, THF, CH₃CN, DCM, MeOH, DCM/MeOH.
[c]Medium indicates the peptide did not deposit on vessel but remained cloudy in solution
[d]All free lysines are TFA salts.

Coupling of Aβ-Binding Peptides to the FKBP Inhibitor:

The FKBP inhibitor 10.6 which contains a 2-carbon linker is coupled first to the Aβ-binding peptides. Specifically, the free lysine epsilon nitrogen in the Aβ-binding peptide is coupled to the free acid on the FKBP inhibitor (see Scheme 11.4). Coupling of Fmoc-K(alloc)LVFFK-NH$_2$ SEQ ID NO: 31 11.36 with FKBP inhibitor 10.6 using PyAOP resulted in no isolation of product. However, synthesis of the FKBP inhibitor acid chloride and then addition of the peptide gave a 13% yield of the conjugate 11.41 which is not completely soluble in DCM, DCM/MeOH, or MeOH. The low yield most likely reflects the insolubility of the final product in the DCM/MeOH solvent used for the column eluant. Fmoc-KLVFF-NH$_2$ SEQ ID NO: 25 11.37 could be successfully coupled to FKBP inhibitor 10.6 with PyAOP/DMF but the product 11.42 could not be separated from the pyrolidine phosphoramide that is formed as the reaction proceeds. In an attempt to facilitate isolation of the product, propylphosphonic anhydride was attempted (unsuccessfully) as the coupling reagent. It should be noted that attempts to remove the phosphoramide via an aqueous wash of the product in DCM were hampered by intractable emulsions. Replacement of the Fmoc group with an acetyl group would likely only magnify the solubility problems and so peptides with a pyridylactetate group (PAc) on the N-terminus were synthesized to improve their solubility.

11.4. Coupling of Aβ-Binding-Peptides to FKBP inhibitor 10.6.

| peptide | conditions | yield of conjugate |
|---|---|---|
| Fmoc-K(alloc)LVFFK-NH$_2$ SEQ. ID. NO:31 11.36 | 1. LiCl/DMF/PyAOP 2. LiCl/DMF (COCl)$_2$ | No Prod. Isolated 13%  11.41 |
| Fmoc-KLVEF-NH$_2$ SEQ. ID. NO:25 11.37 | 1. DMF/PyAOP 2. (Pr$_2$PO)$_3$/DMAP | 58%[a]  11.42 No Prod. Isolated |
| Pyridylacetate-KLVFF-NH$_2$ SEQ. ID. NO:25 11.39 | EDCI/HOBt | 37%  10.8 |
| Pyridylacetate-K(Alloc)LVFFK-NH$_2$ SEQ. ID. NO:31 11.40 | EDCI/HOBt | 20%  10.9 |

[a]contaminated with Phosphoramide 11.5. Coupling of Aβ Binding Peptides to FKBP Inhibitor 10.7.

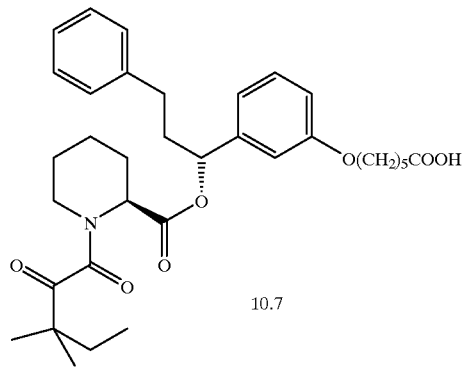

| peptide | conditions | yield |
|---|---|---|
| H$_2$N-K(alloc)LVFF-NH$_2$ SEQ. ID. NO:25 11.38 | DMF/PyAOP | No Prod. Isolated[a] |
| Pyridylacetate-KLVFF-NH$_2$ SEQ. ID. NO:25 11.39 | DMF/PyAOP | 43%  10.10 |

[a]Contaminated with Phosphoramide.

Treatment of Disorders Involving Amyloid Plaque Formation Using Pharmaceutical Compositions Containing the Subject Compounds:

Neuro-degenerative diseases are generally characterized by the formation of patches of sclerosis or plaques at the effected site. The various symptoms suffered by any given patient depends largely upon the location of the lesions. For instance, in the case of multiple sclerosis (MS) (disseminated, focal, or insular), plaques are found in the brain and spinal cord. Symptoms include paralysis, tremor, rhythmic oscillation of the eyeballs (nystagmus), and disturbances in speech. In the case of amyotrophic lateral sclerosis (ALS), plaques form upon the lateral columns and anterior horns of the spinal cord. Here, progressive muscular atrophy is the predominant symptom. In Alzheimer's disease, plaques appear in the brain. Progressive memory loss followed by severe impairment of cognitive abilities is the most predominant symptom.

The invention includes a method of inhibiting or treating neurologic disorders in mammals (especially humans) which involve the formation of such plaques. Principally, the method is drawn to treating or preventing the onset of Alzheimer's disease, multiple sclerosis, or ALS in humans. The method includes administering to a subject in need thereof an effective Aβ peptide aggregation-inhibiting amount of one or more of the subject compounds. The compounds may be administered neat or in the form of a pharmaceutical composition comprising one or more active ingredients in combination with a pharmaceutically-acceptable carrier.

In mammalian subjects, the compounds of Formula I can be administered orally, parenteally (including subcutaneous, intradermal, intramuscular and intravenous injection), rectally, and topically (including dermal, buccal, and sublingual administaion) in combination with an inert liquid or solid pharmaceutically-acceptable carrier which is suitable for the method of administration chosen. The carrier must be pharmaceutically acceptable in the sense of being compatible with the other ingredients of the formulation and not deleterious to the recipient thereof. Such pharmaceutical carriers are well known in the art. The preferred route of administration is orally.

In in vitro applications, such as in the study of mutant cell types, virus types, or other cellular investigations, the pharmaceutical compositions of the present invention are preferably administered to the cells by adding a pre-defined amount of a compound of Formula I, diluted in a suitable diluent, to the cell culture medium. As used herein, the terms "administering" or "administration" are synonymous with "treating" or "treatment." In essence, administering to cells in vitro one or more of the compounds of Formula I entails contacting the cells with the compounds or salts of the compounds.

The in vivo dosage in humans and other mammals depends largely upon the affliction being treated, the time since onset of the condition, the progression of the disease, and the age and general health of the patient being treated. Determining the optimum dosage for any given patient is essentially an empirical and ongoing process. Inhibition or prevention of neurologic disorders in infants and children who are diagnosed early in the progression of the condition may optimally require a more (or less) aggressive treatment than in older patients in more terminal stages of degeneration. Of primary importance in optimizing the most effective dosage is that each patient be carefully monitored throughout the course treatment to follow the progression, if any, of the condition.

A suitable effective dose for most conditions ranges from about 1 mg/kg body weight to about 2 g/kg body weight per day, and is preferably in the range of from about 5 to about 500 mg/kg body weight per day (calculated as the non-salt form of the Formula I compound). The total daily dose may be given as a single dose, multiple doses, e.g., two to six times per day, or by intravenous infusion for a selected duration. Dosages above or below the above-cited ranges are within the scope of the invention and such dosages may be administered to individual patients if the circumstances so dictate.

For example, in a 75 kg mammal, a typical daily dosage might fall within the range of from about 75 mg to about 7.5 g per day. If discrete multiple doses are indicated, treatment might typically comprise 4 equal fractional doses given at 8 hour intervals to supply the total daily dosage.

The active ingredients used in the above-described method and composition include all optical, geometric, and positional isomers of the compounds of Formula I, including racemic mixtures or pure or enriched enantiomeric forms, geometric isomers, and mixtures thereof.

By the term "pharmaceutically-acceptable salt" is meant any salt conventionally used in the formulation and administration of pharmaceutical preparations. This term encompasses inorganic salts such as nitrates, phosphates, sulfates, and chlorides, as well as mono and di-substituted basic salts of sodium, potassium, calcium, and the like. Organic salts such as malonates, fumarates, succinates, crotonates, and the like are also encompassed by the term "pharmaceutically-acceptable salt." The foregoing list is exemplary, not exclusive. A large number of salts acceptable for pharmaceutical administration are known to those of skill in the art.

The pharmaceutical composition may conveniently be presented in unit dosage form and may be prepared by any of the methods well known in the art of pharmacy. The term "unit dosage" or "unit dose" means a predetermined amount of the active ingredient sufficient to be effective for treating amyloid plaque disorders in man. All methods include the step of bringing the active compound(s) into association with a carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulation suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound(s) of Formula I which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the compounds of Formula I are preferable utilized at concentration of from about 0.1% to 5.0% by weight.

Compositions suitable for rectal administration comprise a suppository, preferably bullet-shaped, containing the active ingredient and pharmaceutically acceptable vehicles therefore, such as hard fat, hydrogenated cocoglyceride, polyethylene glycol, and the like. In suppository formulations, the compounds of Formula (1) are preferably utilized at concentrations of from about 0.1% to 10% by weight.

Compositions suitable for rectal administration further comprise a rectal enema unit containing the active ingredient and pharmaceutically acceptable vehicles therefore such as, for example, 50% aqueous ethanol or an aqueous salt solution which is physiologically compatible with the rectum or colon. The rectal enema unit comprises an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the compounds of Formula (1) are preferably utilized at concentrations of from about 5.0% to 10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers.

In pharmaceutical compositions suitable for administration by inhalation, the active ingredient(s) is combined with a carrier comprising a solid in a micronized powder having a particle size in the range of about 5 microns or less to about 500 microns, or a liquid carrier, for rapid inhalation through the oral passage from a conventional metered-dose inhaler or nebulizer. Suitable liquid nasal compositions include conventional nasal sprays, nasal drops and the like, of aqueous solutions of the active ingredient and optional adjuvants.

In addition to the aforementioned ingredients, the pharmaceutical formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

EXAMPLES

The following Examples are included solely to aid in a more complete understanding of the invention disclosed and claimed herein. The Examples do not limit the scope or utility of the invention in any fashion.

General Experimental Procedures:

General Procedure A. BOP-Cl Couplings:

A solution of the N-protected amino acid (1.1 eq) and amino acid ester or peptide amino acid ester (1.0 eq) was cooled to 0° C. in DCM (0.15 M). To the cooled solution was added TEA (2.1 eq) and then BOP-Cl (1.1 eq) in one portion. (An extra equivalent of TEA was added if the amino acid ester or peptide ester was in the form of an HCl salt). The cloudy solution was stirred overnight, warming to room temperature, at which point the solution became clear. The reaction was poured into ethyl acetate (3×reaction volume) and washed with $KHSO_4$, $H_2O$, $NaHCO_3$ and then brine. After drying over $Na_2SO_4$ and filtering, the filtrate was concentrated in vacuo to an oil and purified by flash chromatography.

General Procedure B. BOP-Cl Couplings via Pre-activation:

A solution of the N-protected amino acid (1.1 eq) was cooled to 0° C. in DCM (0.15 M). TEA (1.1 eq) and BOP-Cl (1.1 eq) were added and the reaction was stirred at 0° C. for one hour. A solution of the amino acid ester or peptide ester HCl salt and TEA (1.1 eq) in ca. 1 M DCM was then added to the reaction. After stirring overnight and allowing the reaction to warm to room temperature, the reaction was poured into ethyl acetate (3×reaction volume) and washed with $KHSO_4$, $H_2O$, $NaHCO_3$, and then brine. After drying over $Na_2SO_4$ and filtering, the filtrate was concentrated in vacuo to an oil and purified by flash silica gel chromatography.

General Procedure C. EDCI/HOBt Peptide Coupling:

A solution of the N-protected amino acid (1.1 eq) and amino acid ester HCl salt (or peptide amino acid ester HCl salt) (1.0 eq) in DCM or DMF (0.20 M) was cooled to 0° C. and treated with TEA (1.05 eq), HOBt (1.5 eq), and EDCI (1.1 eq) in one portion. The solution was stirred overnight while warming to room temperature, poured into ethyl acetate (3×reaction volume) and washed with $KHSO_3$, $H_2O$, $NaHCO_3$, and then brine. After drying over $Na_2SO_4$ and filtering, the filtrate was concentrated in vacuo to an oil and purified by flash silica gel chromatography.

General Procedure D. Boc Group Cleavage with 4N HCl/Dioxane:

The Boc-protected amine was dissolved in 4 N HCl/dioxane (20–100 eq) at room temperature and stirred until TLC showed consumption of starting material (ca. 1 hr). The reaction was concentrated in vacuo and then concentrated from ether (3×) and DCM (3×) to produce a white solid.

General Procedure E. TFA Cleavage of Boc Groups:

A solution of the Boc-protected amine in DCM (0.2 M) was cooled to −15° C. in a MeOH/ice bath and treated with TFA, bringing the total concentration of the reaction to 0.1M. The reaction was stirred in the cold, until TLC showed consumption of starting material (ca. 1–2 hr), and then added dropwise into a slurry of $NaHCO_3$ (1.1 g per ml of TFA) in $H_2O$ and DCM. The phases were separated and the aqueous phase was extracted with DCM (3×). The organic layers were combined, dried over $Na_2SO_4$, filtered, and concentrated in vacuo to give the neutral free amine.

General Procedure F. Acetonide Protection of MeLeu(3-OH):

2S,3R MeLeu(3-OH) 3.6 was refluxed overnight in freshly distilled acetone (0.003 M) until an almost clear solution of acetonide-protected MeLeu(3-OH) 4.6 was obtained. After concentrating the reaction volume to 1.5–5.0 ml, the amino acid was added directly to the coupling reaction described in general procedure G.

General Procedure G. Synthesis of CsA Heptapeptide by Acetonide-Protected MeLeu(3-OH):

To solution of the hexapeptide free amine (1.0 eq), N-methylmorpholine (1.1 eq), and HOBt (2.2 eq) in THF (0.05M) was added acetonide-protected MeLeu(3-OH) 4.6 (1.1 eq). The mixture was cooled to 0° C. and DCC (1.1 eq) was added in one portion. After stirring the reaction overnight, the dicyclohexylurea (DCU) that precipitated was removed by filtration through celite and washed with small portions of DCM (3×). The filtrate was concentrated In vacuo and dissolved in ethyl acetate which precipitated additional DCU that was filtered off as before. The filtrate was concentrated in vacuo and the residue was purified by flash chromatography using acetone/hexane gradients.

General Procedure H. Cleavage of N,O-Isopropylidene from Acetonide-Protected Heptapeptide:

To a solution of the N,O-isopropylidene-protected peptide in methanol (0.05 M) was added 1.0 N HCl (aq) (4.0 eq) and the reaction was stirred for 12 hours at room temperature. $NaHCO_3$ (12 eq) was added and the reaction was concentrated in vacuo. The resulting white slurry was taken up in 2–4% MeOH/DCM and purified by flash chromatography with 2–4% MeOH/DCM to yield a white foam.

General Procedure I. CsA Linear Undecapeptide Synthesis via "7+4" Coupling:

To a solution of the amine heptapeptide benzyl ester (1.0 eq) and N-protected tetrapeptide acid (1.3 eq) in DCM (0.05 M) was added BOP reagent (1.3 eq) and N-methylmorpholine (2.0 eq). The reaction was stirred for 3 days at room temperature and then concentrated in vacuo. The residue was dissolved in DCM and washed with $H_2O$, the phases were separated, and the aqueous layer was washed with DCM (2×). The organic layers were combined and dried over $Na_2SO_4$, filtered, concentrated in vacuo, and purified by flash chromatography using MeOH/DCM mixtures as the eluant.

General Procedure J. Cyclization of Undecapeptide to Form Cyclosporin A Analogs:

A solution of the undecapeptide in ethanol at 0° C. was treated with 0.2 N NaOH. The reaction was stirred at 0° C. for 1.5 hours, at which point an additional 1.0 eq of 0.2 N NaOH was added and the stirring was continued at 0° C. for 6–10 more hours. After acidification with 0.2 N HCl to pH 6, the solution was diluted with brine and extracted with DCM (4×), the organic layers were combined, dried over $Na_2SO_4$, filtered and concentrated in vacuo. The residue was dissolved in DCM and propylphosphonic anhydride (50% w/v in DCM) and DMAP were added. The mixture was stirred at room temperature for 3 days under argon, concentrated in vacuo, and purified by flash chromatography using acetone/hexanes as the eluant to yield a white foam.

General procedure K. Cleavage of the Cbz Group from the 7-Position of the CsA Analogs:

A round bottom flask containing the CsA analog and $Pd(OH)_2$ (10–50% by weight) were thoroughly flushed with argon and dissolved in methanol (1–2 ml). The flask was then evacuated and the vacuum was broken with hydrogen (repeated 3×). After stirring for 1–3 hours under 1 atm of $H_2$, the mixture was filtered through an acrodisk and the filtrate was concentrated in vacuo to give the free amine CsA analog which was used directly in the next reaction.

General Procedure L. Automated Synthesis of Aβ-Binding-Peptides Using PerSeptive 9050 Plus synthesizer:

The amino acids (4 equivalents of each) and HOBt (4 equivalents in each vial) were weighed out into the amino acid module cartridges. The resin (1.0 g) was weighed out, swelled with DMF, and packed into the column. The HMPB (hydroxymethylphenoxybutyric acid) resin was used to synthesize C-terminus acids, and the PAL (Peptide Amide Linker) resin was used to synthesize C-terminus amides. DMF was used as the washing and coupling solvent and Fmoc deblock was carried out with 2% DBU in DMF. Syringe 2 was charged with DIPCDI in DMF (5%) which was used as the coupling reagent and acetylimidazole (3.3% w/v) was used as the capping reagent. The peptides were cleaved from the resin by using either 94.5:5:0.5 DCM/$H_2O$/TFA (HMPB resin) or by using 90:10 TFA/$H_2O$ (PAL resin). The insolubility of the peptides precluded any purification so they were used crude after being cleaved from the resin. MALDI-TOV MS was used to confirm the identity of each peptide.

Example 1

Synthesis of 2S,3R McLeu(3-OH)
Route 1: Syn-(4S,2'S,3'R)-3-(4'-methyl-3'-hydroxy-2'-bromo-1'-pen tanoyl)-4-benzyl-2-oxazolidinone 3.8:

A solution of (4S)-3-bromoacetylphenyl-4-phenyl-2-oxazolidinone 3.7 (1.7 g. 5.7 mmol) in ether (28 ml) was cooled to −78° C., and treated with TEA (1.11 ml, 7.98 mmol), followed by di-n-butylboron trillate (1.73 ml, 6.04 mmol). The cooling bath was removed and the reaction was stirred at room temperature for 1.5 hours. After cooling the reaction back to −78° C. with vigorous stirring, isobutyrlaldehyde (0.545 ml, 5.91 mmol) was added and the resulting reaction mixture was stirred at −78° C. for 0.5 hours and at 0° C. for 2 hours. The reaction was diluted with ether (50 ml), washed with $KHSO_4$ (2x), and concentrated in vacuo. The residue was brought up in 1:1 MeOH/$H_2O$ (20 ml), cooled to 0° C., followed by addition of 30% $H_2O_2$ (7 ml). After stirring the reaction for 1 hour at 0° C., it was concentrated in vacuo to give a residue that was diluted with ether (50 ml) and washed with $H_2O$, 1 N $NaHCO_3$, brine, dried over $Na_2SO_4$, filtered and concentrated in vacuo. The residue was purified by flash chromatography (25–30–35% EthOAc/hexane) to give 919 mgs (44% yield) of the aldol product as a foam. $R_f$=0.32 (30% EthOAc/hexane). $[\alpha]_D^{23}$—+51.9 (c 0.30, $CDCl_3$), $^1$H NMR (300 MHz, $CDCl_3$) δ 7.42–7.18 (m, 5H), 5.91 (d, 1H, J=2.3 Hz), 4.8–4.65 (m, 1H), 4.31–4.19 (m, 2H), 3.51 (dd, 1H, J=3, 7.6 Hz), 3.32 (dd, 1H, J=13.5, 3.3 Hz), 2.81 (dd, 1H, J=9.5, 13.5 Hz), 1.96–1.83 (m, 1H), 1.07 (d, 3H, J=6.7 Hz), 0.97 (d, 1H, J=6.7 Hz). $^{13}$C NMR (75.5 MHz, $CDCl_3$) δ 169.55, 152.37, 134.61, 129.47, 129.08, 127.56, 75.59, 66.35, 55.24, 48.93, 36.99, 31.96, 18.78, 18.23. HR-El: calculated for $C_{16}H_{20}NO_4Br$ 369.0576, found 369.0585.

Syn-(4S,2'S,3'R)-3-(4'-methyl-3'-O-N-methylcarbamoyl-2'-bromo-1'pentanoyl)-4-benzyl-2-oxazolidinone 3.9:

A solution of the aldol product 3.8 (694 mg, 1.87 mmol) in toluene (6.5 ml) at room temperature was treated with N-methylisocyanate (0.551 ml, 9.35 mmol) and $BF_3$-$OEt_2$ (0.276 ml, 2.24 mmol). The reaction was stirred for 1 hour, quenched with 5% $NaHCO_3$ (6 ml) and stirred for an additional 30 minutes. After diluting with $H_2O$ (25 ml) and extracting with DCM (3x25 ml), the organic phases were combined, dried over $Na_2SO_4$, filtered, and concentrated in vacuo. The residue was purified by flash chromatography (25–30–35% EthOAc/hexane) to give 583 mgs (73% yield) of the carbamate as a white foam. $R_f$=0.20 (30% EthOAc/hexane). $[\alpha]_D^{23}$=+55.6 (c 0.67, $CDCl_3$), $^1$H NMR (300 MHz, $CDCl_3$) δ 7.34–7.19 (m, 5H), 6.05 (d, 1H, J=3.1 Hz), 4.91–4.78 (m, 1H), 4.64–4.54 (m, 1H), 4.35 (m, 1H), 4.20 (dd, 1H, J=8.9, 2.5 Hz), 3.31 (dd, 1H, J=13.4, 3.3 Hz), 2.90–2.73 (m, 4H), 2.15–2.04 (m, 1H), 1.02 (d, 3H, J=6.8 Hz), 0.95 (d, 3H, J=6.6 Hz). $^{13}$C NMR (75.5 MHz, $CDCl_3$) δ 166.69, 156.66, 153.49, 135.10, 129.47, 128.10, 127.39, 76.62, 66.81, 56.35, 50.7, 37.56, 31.41, 27.67, 18.29, 18.22. HR-EI: calculated for $C_{18}H_{23}N_2O_5Br$ 428.0771, found 428.0777.

(4R,5R)-3-N-Methylmethylester-5-isopropyl-2-oxazolidinone 3.11:

A solution of oxazolidinone carbamate 3.9 (481 mg, 1.12 mmol) in 3:1 THF:$H_2O$ (12 ml) was cooled to 0° C. and treated with LiOH (2.24 ml, 1 N LiOH). The reaction was stirred for 30 minutes and concentrated in vacuo to give a residue that was dissolved in $H_2O$ and washed with EthOAc (3x50 ml), acidified to pH 2 with 2 N HCl, and extracted with DCM (3x75 ml). The organic layers were combined, dried over $Na_2SO_4$, filtered, and concentrated in vacuo to give 288 mgs (82% yield) of the acid 3.10, which was used crude in the next reaction.

A solution of 3.10 (236 mg, 0.88 mmol) in DMF (6 ml) at room temperature was treated with tert-butoxide (494 mg, 4.4 mmol). After stirring the reaction for 30 minutes, toluene was added, and the reaction was concentrated in vacuo to give a residue that was dissolved in $H_2O$ (50 ml), washed with EthOAc, acidified to pH 2 with 2 N HCl, and extracted with EthOAc (6x50 ml). The organic layers were combined, dried over $Na_2SO_4$, filtered, and concentrated in vacuo. The residue was dissolved in 3:1 THF/MeOH (8.8 ml) and treated with TMS diazomethane (0.88 ml, 2 M in hexane). The reaction was stirred for 1 hour and concentrated in vacuo to a residue which was purified by flash chromatography (30–40% EthOAc/hexane) to give 128 mgs (72% over two steps) of 3.11 as a clear, fluid-like oil. $R_f$=0.25 (40% EthOAc/hexane). $[\alpha]_D^{23}$=2.7 (c 0.38, $CDCl_3$), $^1$H NMR (300 MHz, $CDCl_3$) δ 4.26 (d, 1H, J=7.6 Hz), 4.19 (dd, 1H, J=9.1, 7.6 Hz), 3.82 (s, 3H), 2.85 (s, 3H), 1.86–1.71 (m, 1H), 1.07 (d, 3H, J=6.5 Hz), 0.98 (d, 3H, J=6.6 Hz). $^{13}$C NMR (75.5 MHz, $CDCl_3$) δ 168.89, 81.04, 63.81, 52.49, 42.08, 30.25, 29.3, 18.99, 18.44. HR-El: calculated for $C_9H_{15}NO_4$ 201.1001, found 201.0992.

(2S,3R)-MeLeu(3-OH) 3.6:

The oxazolidinone methyl ester 3.11 (400 mg, 2.0 mmol) was dissolved in ethanol (2.27 ml) and treated with KOH (2.27 ml, 1.03 N KOH). The reaction was refluxed for 1 hour, cooled to room temperature, and concentrated in vacuo to give crude 3.12. The resulting white slurry was directly treated with KOH (aq) (4.4 ml, 1.59 M), stirred at 80° C. overnight, and concentrated in vacuo. After acidifying the mixture to pH 6 with 1 N HCl, it was purified by ion-exchange chromatography ("DOWEX" 50x, 4% $NH_4OH$) to give 242 mgs (75% yield) of 3.6 as a white solid. $^1$H NMR (300 MHz, $D_2O$) δ 4.8 (s, 3H), 3.69 (dd, 1H, J=7.15, 5.0 Hz), 3.56 (d, 1H, J=7.15 Hz), 2.73 (s, 3H), 1.82 (m, 1H), 0.97 (d, 3H, J=3.8 Hz), 0.95 (d, 1H, J=3.66 Hz). $^{13C}$ NMR (75.5 MHz, $CDCl_3$) δ 167.98, 80.28, 63.02, 51.72, 29.47, 28.52, 18.21, 17.63.

(2S,3R) MeLeu(3-OH) Synthesis: Route 2
(2E)-4-Methyl-2-penten-1-ol 3.14:

A solution of 3.13 (13 g, 112.5 mmol) in THF (300 ml) at −78° C. was treated dropwise with DIBAL (248 ml of a 1 M solution in THF). The reaction was stirred for 2 hours at −78° C., quenched carefully with MeOH, and diluted with ether (200 ml). The mixture was washed with 3 N HCl, phases were separated, and the aqueous phase was extracted with ether (3x100 ml). The combined organic layers were washed with brine, dried over $Na_2SO_4$, filtered, and concentrated in vacuo. The residue was distilled under reduced pressure to give 9.6 g (85% yield) of the alcohol 3.14. $R_f$=0.55 (30% EthOAc/hexanes). $^1$H NMR (300 MHz, $CDCl_3$) δ 5.73–5.5 (m, 1H), 4.12–4.03 (m, 1H), 2.39–2.2 (m, 1H), 1.55 (bs, 1H), 1.0 (d, 6H, J=6.6Hz).

(2S,3R)-4-Methyl-2,3-epoxy-1-ol 3.15:

A flame-dried flask was charged with 4-angstrom powdered molecular sieves (2.34 g) and DCM (275 ml) and then cooled to −20° C. in MeOH/ice bath. D-(−)diethyl tartarate (0.99 ml, 4.7 mmol) and Ti(Oi-Pr)$_4$ (1.16 ml, 3.9 mmol) were added sequentially, followed by cumene hydroperoxide (80% solution, stored over 4-angstrom molecular sieves, 28.9 ml, 156 mmol) at a moderate rate. The resulting reaction mixture was transferred to the refrigeration apparatus set at −20° C., stirred for 30 minutes, and then treated with allylic alcohol 3.14 (7.8 g, 78 mmol) dropwise over 10 minutes, and the resulting mixture was stirred overnight at −20° C.

A freshly prepared solution of ferrous sulfate heptahydrate (25.8 g) and tartaric acid (7.8 g) in deionized $H_2O$ (78 ml) was cooled to 0° C. The epoxidation reaction was allowed to warm to 0° C. and was then poured into a beaker containing the precooled ferrous sulfate solution. The two-phase mixture was stirred for 5–10 minutes and then transferred to a separatory funnel. After the phases were separated, the aqueous phase was extracted with ether (2×100 ml) and the combined organic layers were treated with a precooled solution of 30% NaOH (w/v) (7.8 ml) in saturated brine and stirred vigorously for 1 hour at 0° C. The reaction mixture was diluted with $H_2O$, the phases were separated, and the aqueous layer was extracted with ether (3×100 ml). The combined organic phases were dried over $Na_2SO_4$, filtered, and concentrated in vacuo to give a residue which was purified by flash chromatography (2:1 hexance/EthOAc) to give 6.5 g (72% yield) of the epoxide 3.15 as a colorless oil. $R_f$=0.35 (33% EthOAc/hexanes). $^1$H NMR (300 MHz, $CDCl_3$) δ 3.92 (d, 1H, J=11.7 Hz), 3.72–3.53 (m, 1H), 3.02–2.95 (m, 1H), 2.76 (dd, 1H, J=6.8, 2.4 Hz), 2.30 (m, 1H), 1.66–1.50 (m, 1H), 1.03 (d, 3H, J=6.7 Hz), 0.97 (d, 3H, J=6.9 Hz). $^{13}$C NMR (75.5 MHz, $CDCl_3$) δ 61.94, 61.22, 57.59, 30.03, 18.96, 18.31.

(2S,3R)-4-Methyl-2,3-epoxy-1-O-methylcarbamate 3.17:

A solution of the epoxy alcohol 3.15 (1.014 g, 8.75 mmol) in DCM (130 ml) was treated sequentially with TEA (3.05 ml, 21.88 mmol) and methylisocyanate (1.032 ml, 17.5 mmol). The mixture was stirred under argon for 20 hours, quenched with satd. $NH_4Cl$, and transferred to a separatory funnel. The phases were separated and the aqueous phase was extracted with DCM (3×100 ml). The combined organic phases were dried over $Na_2SO_4$, filtered, and concentrated in vacuo to give a residue which was purified by flash chromatography (30% EthOAc/hexane) to give 1.32 g (87% yield) of the carbamate 3.17 as a colorless oil. $R_f$=0.55 (30% EthOAc/hexanes). $^1$H NMR (300 MHz, $CDCl_3$) δ 4.75 (bs, 1H), 4.40 (dd, 1H, J=12.21, 2.85 Hz), 3.89 (dd, 1H, J=12.13, 6.4 Hz), 3.01 (m, 1H), 2.81 (d, 3H, J=4.94 Hz), 2.65 (dd, 1H, J=6.72, 2.67 Hz), 1.65–1.50 (m, 1H), 1.01 (d, 3H, J=6.72 Hz), 0.96 (d, 3H, J=6.87 Hz). $^{13}$C NMR (75.5 MHz, $CDCl_3$) δ 65.63, 61.92, 54.79, 30.07, 27.50, 18.87, 18.25. FABMS: found 174.1 [M+H$^+$].

(4R,5R)-3-N-Methyl-4-hydroxymethyl-5-isopropyl-2-oxazolidinone 3.16:

A solution of KH (224 mg, 5.6 mmol) in THF (50 ml) at 0° C. was treated dropwise with a solution of the carbamate 3.17 (647 mg, 3.74 mmol) in THF (5 ml). The reaction was stirred at 0° C. for 2 hours and then at room temperature for 1 hour. After quenching the reaction at 0° C. with 1 N $KHSO_4$ to pH 5, it was extracted with $CHCl_3$ (9×50 ml) and the combined organic layers were dried over $Na_2SO_4$, filtered, and concentrated in vacuo. The residue was purified by flash chromatography (30–40% acetone/hexane) to give 415 mgs (65% yield) of the desired oxazolidinone 3.16 as a white solid, and 104 mgs (16% yield) of the other isomer 3.18. Data for 3.16: $R_f$=0.38 (50% acetone/hexanes). $^1$H NMR (300 MHz, $CDCl_3$) δ 4.05 (dd, 1H, J=10.38, 7.04 Hz), 3.86 (m, 1H), 3.61 (m, 1H), 2.94 (s, 3H), 2.86 (m, 1H), 2.15 (m, 1H), 1.09 (d, 3H, J=6.45 Hz), 0.956 (d, 3H, J=6.6 Hz). $^{13}$C NMR (75.5 MHz, $CDCl_3$) δ 159.38, 82.6, 61.08, 52.28, 29.80, 27.49, 19.68, 18.94. HR-EI: calculated for $C_8H_{15}NO_3$ 173.1052, found 173.1057. Data for 3.18: $R_f$0.45 (50% acetone/hexanes). $^1$H NMR (300 MHz, $CDCl_3$) δ 4.32 (dd, 1H, J=8.5, 6.9 Hz), 4.18 (dd, 1H, J=8.5, 8.5 Hz), 3.75 (m, 1H), 3.47 (d, 1H, J=8.17 Hz), 3.01 (d, 1H, J=3.8 Hz), 2.78 (s, 3H), 1.55 (m, 1H), 0.98 (d, 3H, J=6.61 Hz), 0.83 (d, 3H, J=6.79 Hz). $^{13}$C NMR (75.5 MHz, $CDCl_3$) δ 159.38, 72.33, 61.92, 59.85, 30.47, 29.08, 19.40, 18.95. FABMS found 174.1 [M+H$^+$].

(4R,5R)-3-N-Methyl-4-methylester-5-isopropyl-2-oxazolidinone 3.11:

A solution of the oxazoludinone alcohol 3.16 (600 mg, 3.47 mmol) in acetone (16 ml) at 0° C. was treated with Jones reagent (1.55 ml, prepared by adding 5.34 g of $CrO_3$ dropwise to 4.6 ml conc. $H_2SO_4$ and diluting with water to 20 ml) and stirred for 1 hour at room temperature. An additional 0.400 ml of Jones reagent was added and the reaction was stirred for another hour. After decomposing the remaining Jones reagent with isopropanol, the reaction mixture was decanted into another flask and the remaining solids were dissolved in satd. NaCl and extracted with $CHCl_3$ (3×50 ml). The organic layers were combined, dried over $Na_2SO_4$, filtered and concentrated in vacuo to give 3.10 which was used directly in the next reaction.

Acid 3.10 was dissolved in 3:1 benzene/MeOH (36 ml) and treated with TMS-diazomethane (3.47 ml, 2 M in hexanes). The reaction mixture was stirred for 1 hour at room temperature and concentrated in vacuo. The residue was purified by flash chromatography (40% EthOAc/hexane) to give 490 mgs (70% over two steps) of the methyl ester 3.11 as a colorless oil. $R_f$=0.25 (40% EthOAc/hexane). $[α]_D^{23}$=−2.7 (c 0.38, $CDCl_3$), $^1$H NMR (300 MHz, $CDCl_3$) δ 4.26 (d, 1H, J=7.6 Hz), 4.19 (dd, 1H, J=9.1, 7.6 Hz), 3.82 (s, 3H), 2.85 (s, 3H), 1.86–1.71 (m, 1H), 1.07 (d, 3H, J=6.5 Hz), 0.98 (d, 3H, J=6.6 Hz). $^{13}$C NMR (75.5 MHz, $CDCl_3$) δ 168.89, 81.04, 63.81, 52.49, 42.08, 30.25, 29.3, 18.99, 18.44. HR-EI: calculated for $C_9H_{15}NO_4$ 201.1001, found 201.0992.

Example 2

Synthesis of CsA Analogs

Boc-MeLeu-Lys(2Cl-Cbz)-OBn 4.1:

Following generalprocedure A, the title compound was synthesized in 80% yield by coupling of the HCl salt of H-Lys(2Cl-Cbz)-OBn (8.56 g, 19.4 mmol) to Boc-MeLeu-OH (5.24 g, 21.3 mmol) in DCM (130 ml) with BOP-Cl (5.43 g, 21.3 mmol) and DIEA (10.5 ml, 60.1 mmol) to give 9.78 g of the dipeptide. $R_f$=0.29 (30% EthOAc/hexane), $[α]_D^{23}$=−53.01 (c 0.415, $CHCl_3$), FABMS $C_{33}H_{46}N_3O_7Cl$) found 632.1.

Boc-Val-MeLeu-Lys(2Cl-Cbz)-OBn 4.2:

Following general procedure D, the Boc group in Boc-MeLeu-Lys(2Cl-Cbz)-OBn 4.1 (9.78 g, 15.5 mmol) was cleaved to form the HCl salt of MeLeu-Lys(2Cl-Cbz)-OBn, which was coupled to Boc-Val-OH (3.7 g, 17.0 mmol) in DCM (105 ml) with BOP-Cl (4.33 g, 17.0 mmol) and DIEA (8.35 ml, 48.0 mmol) via general procedure B to give 6.68 g (59% yield) of the title compound. $R_f$=0.30 (40% EthOAc/hexane), $[α_D^{23}$=−59.30 (c 0.860, $CHCl_3$), FABMS ($C_{36}H_{55}N_4O_8Cl$) found 731.2.

Boc-MeLeu-Val-MeLeu-Lys(2Cl-Cbz)-OBn (SEQ. ID. NO: 2) 4.3:

Following general procedure D, the Boc group in Boc-Val-MeLeu-Lys(2Cl-Cbz)-OBn 4.2 (6.68 g, 9.13 mmol) was cleaved to form the HCl salt of Val-MeLeu-Lys(2Cl-Cbz)-OBn, which was coupled to Boc-MeLeu-OH (2.463 g, 10.04 mmol) in DCM (60 ml) with BOP-Cl (2.553 g, 10.04 mmol) and DIEA (4.93 ml, 28.3 mmol) via general procedure A to give 5.367 g (69% yield) of the title compound. $R_f$=0.37 (50% EthOAc/hexane), $[α]_D^{23}$ =−94.33 (c 0.670, $CHCl_3$), FABMS ($C_{45}H_{68}N_5O_9Cl$) found 858.3.

Boc-(D))MeSer(OBn)-MeLeu-Val-MeLeu-Lys(2 Cl-Cbz)-OBn (SEQ. ID. NO: 3) 4.4:

Following general procedure E, the Boc group in Boc-MeLeu-Val-MeLeu-Lys(2Cl-Cbz)-OBn 4.3 (773 mg, 0.886 mmol) was cleaved to form H-MeLeu-Val-MeLeu-Lys(2Cl-Cbz)-OBn, which was coupled to Boc-(D)MeSer(OBn)-OH-DCHA salt (464 mg, 0.946 mmol) in DCM (6 ml) with BOP-Cl (241 mg, 0.946 mmol) and DIEA (0.165 ml, 0.946 mmol) via general procedure A to give 638 mg (71% yield) of the title compound. $R_f$=0.33 (50% EthOAc/hexane), $[\alpha]_D^{13}$=−48.09 (c 0.47, CHCl$_3$), FABMS ($C_{56}N_{81}O_{11}Cl$) found 1049.3.

Boc-Abu-(D)MeSer(OBn)-MeLeu-Val-MeLeu-Lys(2Cl-Cbz)-OBn (SEQ. ID. NO: 4) 4.5:

Following general procedure E, the Boc group in Boc-(D)MeSer(OBn)-MeLeu-Val-MeLeu-Lys(2Cl-Cbz)-OBn 4.4 (618 mg, 0.589 mmol) was cleaved to form H-(D)MeSer(OBn)Val-MLeue-Lys(2Cl-Cbz)-OBn, which was coupled to Boc-Abu-OH (247 mg, 1.22 mmol) in DCM (5 ml) with BOP-Cl (311 mg, 1.82 mmol) and DIEA (0.313 ml, 1.82 mmol) via general procedure B to give 450 mg (68% yield) of the title compound. $R_f$=0.33 (50% EthOAc/hexane), $[\alpha]_D^{23}$=−66.10 (c 0.295, CHCl$_3$), FABMS ($C_{60}H_{88}N_7O_{12}Cl$) found 1134.4.

Acetonide-MeLeu(3-OH)-Abu-(d)MeSer(OBn)-MeLeu-Val-MeLeu-Lys(2Cl-Cbz)-OBn (SEQ. ID. NO: 5) 4.7:

Following general procedure F, MeLeu(3-OH) 3.6 (50 mg, 0.31 mmol) in refluxing acetone (100 ml) was protected as the N,O-acetonide 4.6 and used in the coupling reaction below.

Following general procedure E, the Boc group in Boc-Abu-(D)MeSer(OBn)-MeLeu-Val-MeLeu-Lys(2Cl-Cbz)-OBn 4.5 (330 mg, 0.29 mmol) was cleaved to form H-Abu-(D)MeSer(OBn)-MeLeu-Val-MeLeu-Lys(2Cl-Cbz)-OBn, which was coupled to the protected MeLeu(3-OH) in THF (4.5 ml) with DCC (64 mg, 0.31 mmol), HOBt (84 mg, 0.62 mmol) and NMM (0.034 ml, 0.31 mmol) via general procedure G to give 245 mg (70% yield) of the title compound. The compound was purified by flash chromatography with a 10–20–30% acetone/hexane gradient. $R_f$=0.38 (40% acetone/hexane), $[\alpha]_D^{23}$=−40.0 (c 0.295, CHCl$_3$), FABMS ($C_{65}H_{97}N_8O_{122}Cl$) found 1217.5.

H-MeLeu(3-OH)-Abu-(D))MeSer(OBn)-MeLeu-Val-MeLeu-Lys(2Cl-Cbz)-OBn (SEQ. ID. NO: 6) 4.8:

Following general procedure H, the acetonide was cleaved from the protected heptapeptide 4.7 (235 mg, 0.193 mmol) with 1 N HCl (aq) (0.772 ml) in MeOH (3.92 ml) to give 173 mgs (76% yield) of the title compound. $R_f$=0.11 (5% MeOH/DCM), $[\alpha]_D^{23}$=−88.6 (c 0.175, CHCl$_3$), FABMS ($C_{62}H_{93}N_8O_{12}Cl$) found 1177.5.

Fmoc-(D)Ala-MeLeu-MeLeu MeVal-MeLeu(3-OH)-Abu-(D)MeSer(OBn)-MeLeu-Val-MeLeu-Lys(2Cl-Cbz)-OBn (SEQ ID. NO: 7) 4.9:

Following general procedure I, H-MeLeu-Abu-(D)MeSer(OBn)-MeLeu-Val-MeLeu-Lys(2Cl-Cbz)-OBn 4.8 (170 mg, 0.144 mmol) was coupled to Fmoc-(D)Ala-MeLeu-MeLeu-MeVal-OH (SEQ. ID. NO: 28) (147 mg, 0.216 mmol) in DCM (3 ml) with BOP (96 mg, 0.216 mmol) and NMM (0.040 ml, 0.36 mmol) to give 139 mg (53% yield) of the title compound. The compound was purified by flash chromatography with a 10–20–30–40% acetone/hexane gradient. $R_f$=0.55 (50% acetone/hexane), $[\alpha]_D^{23}$=−95.5 (c 0.20, CHCl$_3$), FABMS ($C_{100}H_{145}N_{12}O_{18}Cl$) found 1837.9.

(MeLeu(3-OH)$^1$, (D)MeSer(OBn)$^3$, Lys(2Cl-Cbz)$^7$)-CsA (SEQ. ID. NO: 9) 4.10:

Following general procedure J, Fmoc-(D)Ala-MeLeu-MeLeu-MeVal-MeLeu(3-OH)-Abu-(D))MeSer(OBn)-MeLeu-Val-MeLeu-Lys(2Cl-Cbz)-OBn 4.9 (133 mg, 0.0724 mmol) was treated with 0.2 N NaOH (0.8 ml) in ethanol (3.5 ml) to give the deprotected undecapeptide, which was cyclized by using propylphosponic anhydride (0.054 ml, 50% (v/v) in DCM) and DMAP (49 mg, 0.398 mmol) in DCM (345 ml). The compound was purified by flash chromatography (10–20–30% acetone/hexane) to give 72 mg (66% yield) of the CsA analog 4.10. $R_f$=0.46 (50% acetone/hexane), FABMS ($C_{78}H_{127}N_{12}O_{15}Cl$) found 1507.7.

Boc-(D)MeSer(OTBS)-OH 4.13:

A solution of Boc-(D)MeSer-OH 4.12 (3.641 g, 16.47 mmol) in DMF (80 ml) was treated with TBS-Cl (12.413 g, 82.35 mmol) and imidazole (11.213 g, 164.7 mmol). The reaction was stirred overnight at room temperature, and then concentrated from toluene in vacuo on the high-vacuum. The residue was suspended in H$_2$O, acidified to pH 4 with 10% citric acid, and extracted with ether (3×). The combined organic layers were dried over Na$_2$SO$_4$, filtered, and concentrated in vacuo. The residue was purified by flash chromatography (100% DCM, then 7–10% MeOH/DCM9 to give 3.404 g (62% yield) of the title compound. $R_f$=0.68 (95:4:1 DCM/MeOH/HOAc), $[\alpha]_D^{23}$=+4.4 (c 0.635, CHCl$_3$), $^1$H NMR (300 MHz, CDCl$_3$) (mixture of cis-trans isomers) δ 4.68–4.28 (m, 1H), 4.06–3.85 (m, 2H), 2.95–2.81 (m, 3H), 1.46–1.36 (m, 9H), 0.90–0.78 (m, 9H), 0.10-(−) 0.03 (m, 6H).

Boc-(D)MeSer(OTBS)-MeLeu-Val-MeLeu-Lys(2Cl-Cbz)-OBn (SEQ. ID. NO: 10) 4.15:

Following general procedure E, the Boc group in Boc-MeLeu-Val-MeLeu-Lys(2Cl-Cbz)-OBn 4.3 (7.966 g, 9.279 mmol) was cleaved to form H-MeLeu-Val-MeLeu-Lys(2Cl-Cbz)-OBn, which was coupled to Boc-(D)MeSer(OTBS)-OH4.13 (3.405 g, 10.21 mmol) in DCM (62 ml) with BOP-Cl (2.596 g, 10.21 mmol) and DIEA (3.395 ml, 19.49 mmol) via general procedure A to give 5.38 g (58% yield) of the title compound. $R_f$=0.60 (60% EthOAc/hexane), $[\alpha]_D^{23}$=−48.24 (c 0.425, CHCl$_3$), FABMS ($C_{55}H_{88}N_6O_{11}ClSi$) found 1073.6.

Boc-(D)MeSer-MeLeu-Val-MeLeu-Lys(2Cl-Cbz)-OBn (SEQ. ID. NO: 11) 4.14:

A solution of Boc-(D)MeSer(OTBS)-MeLeu-Lys(2Cl-Cbz)-OBn 4.15 (5.23 g, 4.87 mmol) in THF (88 ml) was treated with HF/pyridine stock solution (74 ml of a stock solution prepared from 18.75 g HF/pyridine, 18.8 ml pyridine, and 75 ml THF) and the reaction was stirred at room temperature for 5 hours. The reaction mixture was combined with 75 ml of 1 N NaHCO$_3$, and extracted with DCM (3×250 ml). The organic layers were combined, dried over Na$_2$SO$_4$, filtered, and concentrated in vacuo. The residue was purified by flash chromatography (60% EthOAC/hexane) to give 4.15 g (89% yield) of the title compound. $R_f$=0.10 (60% EthOAc/hexane), $[\alpha]_D^{23}$=−45.0 (c 0.5, CHCl$_3$), FABMS ($C_{49}H_{75}N_6O_{11}Cl$) found 959.5.

Boc-Abu-(D)MeSer-MeLeue-Val-MeLeu-Lys(2Cl-Cbz)-OBn (SEQ. ID. NO: 12) 4.16:

Following general procedure E, the Boc group in Boc-(D)MeSer-MeLeu-Val-MeLeu-Lys(2Cl-Cbz)-OBn 4.14 (934 mg, 0.975 mmol) was cleaved to form H-(D)MeSer-Val-MeLeu-Lys(2Cl-Cbz)-Obn, which was coupled to Boc-Abu-OH (217 mg, 1.07 mmol) in DCM (6.5 ml) with BOP-Ci (272 mg, 1.07 mmol) and DIEA (0.357 ml, 2.05 mmol) via general procedure B to give 693 mg (68% yield) of the title compound. $R_f$=0.36 (80% EthOAc/hexane), $[\alpha]_D^{23}$=−48.4 (c 0.57 CHCl$_3$), FABMS ($C_{53}H_{82}N_7O_{12}Cl$) m/z 1044.5.

Acetonide-MeLeu(3OH)-Abu-(D)MeSer-MeLeu-Val-MeLeu-Lys(2Cl-Cbz)-OBn (SEQ. ID. NO; 13) 4.17:

Following general procedure F, MeLeu(3-OH) 3.16 (509 mg, 3.16 mmol) in refluxing acetone (1400 ml) was protected as the N,O-acetonide 4.6 and used in the coupling reaction below.

Following general procedure E, the Boc group in Boc-Abu-(D)McSer-MeLeu-Val-MeLeu-Lys(2Cl-Cbz)-OBn 4.16 (3 g, 2.87 mmol) was cleaved to form H-Abu-(D)MeSer(OBn)-MeLeu-Val-MeLeu-Lys(2Cl-Cbz)-OBn, which was coupled to the protected MeLeu(3-OH) 4.6 in THF (49 ml) with DCC (652 mg, 3.16 mmol), HOBt (852 mg, 3.16 mmol) and NMM (0.347 ml, 3.16 mmol) via general procedure G to give 2.58 mg (80% yield) of the title compound. The compound was purified by flash chromatography with a 20–30–40–50% acetone/hexane gradient. $R_f$=0.6 (50% acetone/hexane), $[\alpha]_D^{23}$=–44.1 (c 0.365, CHCl$_3$), FABMS ($C_{58}H_{91}N_8O_{12}Cl$) found 1127.5.

H-MeLeu(3-OH)-Abu-(D)MeSer-McLeu-Val-MeLeu-Lys(2Cl-Cbz)-OBn (SEQ. ID. NO: 14) 4.18:

Following general procedure H, the acetonide was cleaved from the protected heptapeptide 4.17 (2.55 g, 2.26 mmol) with 1 N HCl (aq) (9.04 ml) in MeOH (45 ml) to give 1.65 g (67% yield) of the title compound. $R_f$=0.25 (10% MeOH/DCM), $[\alpha]_D^{23}$–41.5 (c 0.585, CHCl$_3$, FABMS ($C_{55}H_{87}N_8O_{12}Cl$) m/z 1087.5.

Fmoc-(D))Ala-MeLeu-MeLeu-MeVal-MeLeu(3-OH)-Abu-(D)MeSer-MeLeu-Val-MeLeu-Lys(2Cl-Cbz)-OBn (SEQ. ID. NO: 15) 4.19:

Following general procedure I, H-MeLeu-Abu-(D)MeSer(OBn)-MeLeu-Val-MeLeu-Lys(2Cl-Cbz)-OBn 4M (1.63 g, 1.48 mmol) was coupled to Fmoc-(D)Ala-MeLeu-MeLeu-MeVal-OH (1.13 g, 1.92 mmol) in DCM (30 ml) with BOP (851 mg, 2.22 mmol) and NMM (0.325 ml, 2.96 mmol) to give 1.3 g (50% yield) of the title compound. The compound was purified by flash chromatography with a 20–30–40% acetone/hexane gradient. $R_f$=0.46 (50% acetone/hexane), $[\alpha]_D^{23}$=–107.8 (c 0.45, CHCl$_3$), FABMS ($C_{93}H_{139}N_{12}O_{20}Cl$) found 1749.0.

(MeLeu(3-OH)$^1$, (D)MeSer(OBn)$^3$, Lys(2Cl-Cbz)$^7$)-CsA (SEQ. ID. NO: 16) 4.20:

Following general procedure I, Fmoc-(D)Ala-MeLeu-MeLeu-MeVal-McLeu(3-OH)-Abu-(D)MeSer-MeLeu-Val-MeLeu-Lys(2Cl-Cbz)-OBn (1.25 g, 0.715 mmol) 4.19 was treated with 0.2 N NaOH (7.85 ml+3.9 ml) in ethanol (36 ml) to give the deprotected undecapeptide, which was cyclized by using propylphosponic anhydride (0.526 ml, 50% (v/v) in DCM) and DMAP (480 mg, 3.93 mmol) in DCM (345 ml). The compound was purified with flash chromatography (10–20–30% acetone/hexane) to give 531 mg (53% yield) of the tide compound. $R_f$=0.42 (50% acetone/hexane), FABMS ($C_{71}H_{121}N_{12}O_{15}Cl$) found 1417.8.

Boc-MeAla-Lys(2Cl-Cbz)-OBn 11.1:

Following general procedure A, the title compound was synthesized in 80% yield by coupling of the HCl salt of H-Lys(2Cl-Cbz)-OBn (8.81 g, 20.8 mmol) to BocMeAla-OH (4.65 g, 22.9 mmol) in DCM (140 ml) with BOP-Cl (5.83 g, 21.3 mmol) and DIEA (11.24 ml, 65.5 mmol) to give 9.82 g of the dipeptide. $R_f$=0.50 (50% EthOAc/hexane), $[\alpha]_D^{23}$=–38.6 (c 0.515, CHCl$_3$), FABMS ($C_{30}H_{40}N_3O_7Cl$) found 590.3.

Boc-Val-MeAla-Lys(2Cl-Cbz)-OBn 11.2:

Following general procedure D, the Boc group in BocMeLeu-Lys(2Cl-Cbz)-OBn 11.1 (9.753 g, 16.5 mmol) was cleaved to form the HCl salt of MeLeu-Lys(2Cl-Cbz)-OBn, which was coupled to Boc-Val-OH (3.957 g, 18.2 mmol) in DCM (110 ml) with BOP-Cl (4.63 g, 18.2 mmol) and DIEA (8.935 ml, 51.3 mmol) via general procedure B to give 7.23 g (63% yield) of the title compound. $R_f$=0.30 (60% EthOAc/hexane), $[\alpha]_D^{23}$=–92.6 (c 0.685, CHCl$_3$), FABMS ($C_{35}H_{49}N_4O_8Cl$) found 689.4.

Boc-MeAla-Val-MeAla-Lys(2Cl-Cbz)-OBn (SEQ. ID. NO: 8) 11.3:

Following general procedure D, the Boc group in BocVal-MeAla-Lys(2Cl-Cbz)-OBn 11.2 (7.27 g, 10.5 mmol) was cleaved to form the HCl salt of Val-MeLeu-Lys(2Cl-Cbz)-OBn, which was coupled to Boc-MeAla-OH (2.35 g, 11.6 mmol) in DCM (70 ml) with BOP-Cl (2.94 g, 11.6 mmol) and DIEA (5.7 ml, 32.6 mmol) via general procedure A to give 3.50 g (43% yield) of the title compound. $R_f$=0.30 (80% EthOAc/hexane), $[\alpha]_D^{23}$=–90.6 (c 0.545, CHCl$_3$), FABMS ($C_{39}H_{56}N_5O_9Cl$) found 774.4.

Boc-Abu-Sar-MeAla-Val-MeAla-Lys(2Cl-Cbz)-OBn (SEQ. ID. NO: 17) 11.4:

Following general procedure E, the Boc group in BocMeAla-Val-MeAla-Lys(2Cl-Cbz)-OBn 11.3 (665 mg, 0.86 mmol) was cleaved to form H-MeAla-Val-MeAla-Lys(2Cl-Cbz)-OBn, which was coupled to Boc-Abu-Sar-OH (260 mg, 0.946 mmol) in DCM (9 ml) with BOP-Cl (240 mg, 0.946 mmol) and DIEA (0.314 ml, 1.81 mmol) via general procedure A to give 576 mg (72% yield) of the title compound. The compound was purified by flash chromatography (50% acetone/hexane). $R_f$=0.20 (50% acetone/hexane), $[\alpha]_D^{23}$=–92.7 (c 0.655, CHCl$_3$), FABMS ($C_{46}H_{68}N_7O_{11}Cl$) found 952.5 (M+Na$^+$).

Acetonide-MeLeu(3-OH)-Abu-Sar-MeAla-Val-MeAla-Lys(2Cl-Cbz)-OBn (SEQ. ID NO: 18) 11.5:

Following general procedure F, MeLeu(3-OH) 3.6 (240 mg, 1.49 mmol) in refluxing acetone (240 ml) was protected as the N,O-acetonide 4.8 and used in the coupling reaction below.

Following general procedure E, the Boc group in BocAbu-Sar-MeAla-Val-MeAla-Lys(2Cl-Cbz)-OBn 11.4 (1.26 g, 1.36 mmol) was cleaved to form H-Abu-Sar-MeAla-Val-MeAla-Lys(2Cl-Cbz)-OBn, which was coupled to the protected MeLeu(3-OH) in THF (20.5 ml) with DCC (308 mg, 1.49 mmol), HOBt (403 mg, 2.98 mmol) and NMM (0.164 ml, 1.49 mmol) via general procedure G to give 920 mg (67% yield) of the title compound. The compound was purified by flash chromatography with a 30% acetone/hexane gradient. $R_f$=0.26 (50% acetone/hexane), $[\alpha]_D^{23}$=–94.8 (c 0.81, CHCl$_3$), FABMS ($C_{51}H_{77}N_8O_{11}Cl$) m/z 1013.7.

H-MeLeu(3-OH)-Abu-Sar-MeAla-Val-McAla-Lys(2Cl-Cbz)-Obn (SEQ. ID. NO: 19) 11.6:

Following general procedure H, the acetonide was cleaved from the protected heptapeptide 11.5 (862 mg, 0.85 mmol) with 1 N HCl (aq) (3.4 ml) in MeOH (17 ml) to give 700 mgs (84% yield) of the title compound. The compound was purified by flash chromatography with a 4–5% MeOH/DCM gradient. $R_f$=0.33 (10% MeOH/DCM), $[\alpha]_D^{23}$=–95.6 (c 0.455, CHCl$_3$), FABMS ($C_{48}H_{73}N_8O_{11}Cl$) found 973.5.

Fmoc-(D)Ala-MeLeu-MeLeu-MeVal-MeLeu(3OH)-Abu-(D)MeSer(OBn)-MeLeu-Val-MeLeu-Lys(2Cl-Cbz)-OBn (SEQ. ID. NO: 20) 11.7:

Following general procedure I, the H-MeLeu-Abu-Sar-MeAla-Val-MeAla-Lys(2Cl-Cbz)-OBn 11.6 (670 mg, 0.69 mmol) was coupled to Fmoc-(D)Ala-MeLeu-MeLeu-MeVal-OH (640 mg, 0.943 mmol) in DCM (14 ml) with BOP (457 mg, 1.03 mmol) and NMM (0.189 ml, 1.72 mmol) to give 658 mg (59% yield) of the title compound. The compound was purified by flash chromatography with a 20–30–40–50% acetone/hexane gradient. $R_f$=0.39 (50% acetone/hexane), $[\alpha]_D^{23}$=–133.0 (c 0.43, CHCl$_3$), FABMS ($C_{86}H_{125}N_{12}O_{17}Cl$) found 1634.4.

(MeLeu(3-OH)$^1$, MeAla$^{4,6}$, Lys(2Cl-Cbz)$^7$)-CsA (SEQ. ID. NO: 21) 11.8:

Following general procedure I, Fmoc-(D)Ala-MeLeu-MeLeu-MeVal-MeLeu(3-OH)-Abu-Sar-MeAla-Val-McAla-Lys(2Cl-Cbz)-OBn 11.7 (640 mg, 0.391 mmol) was treated with 0.2 N NaOH (4.3 ml+2.1 ml) in ethanol (20 ml) to give the deprotected undecapeptide, which was cyclized by using propylphosponic anhydride (0.288 ml, 50% (v/v) in DCM) and DMAP (263 mg, 2.15 mmol) in DCM (1.86 L). The compound was purified with flash chromatography (10–20–30–40–50% acetone/hexane) to give 380 mg (75% yield) of the title compound. $R_f$=0.32 (50% acetone/hexane), FABMS ($C_{64}H_{106}N_{12}O_{14}Cl$) found 1303.8.

Acetylcyclosporin A 4.21:

A solution of CsA (200 mg, 0.168 mmol) in acetic anhydride (3.5 ml) was treated with DMAP (41 mg, 0.337 mmol) and the reaction was stirred for 48 hours at room temperature. The reaction was poured into H$_2$O (25 ml) and ether (25 280 ml), phases were separated, and the aqueous phase was extracted with ether (2×25 ml). The organic phases were combined, dried over Na$_2$SO$_4$, filtered, and concentrated in vacuo. The residue was purified by flash chromatography (20–30–40% acetone/hexane) to give 136 mgs of the title compound (65% yield). FABMS calculated for C$_{64}$H$_{113}$N$_{11}$O$_{13}$ 1244.6, found 1244.8.

η-Acetoxyacetylcyclosporin A 4.23:

A solution of acetylcyclosporin A in CCl$_4$ was treated with azobisisobutyronitrile (AIBN) and N-bromosuccinimide (NBS). The reaction was refluxed for 2.5 hours and then concentrated in vacuo. The residue was brought up in ether and filtered through celite. The filtrate was washed with H$_2$O, dried over Na$_2$SO$_4$, filtered, and concentrated in vacuo to give crude 4.22. The residue was dissolved in methyl ethyl ketone, and tetraethylammonium acetate hydrate and NaI (cat.) were added to the solution. The reaction was stirred at 60–80° C. for 3 hours and then room temperature for 2 days, diluted with methyl tert-butyl ether and washed with H$_2$O, and brine. The organic layer was dried over Na$_2$SO$_4$, filtered, and concentrated in vacuo. The residue was purified by flash chromatography (20–30–40–50% acetone/hexane) to give 42 mgs (47% yield) of the title compound. FABMS calculated for C$_{66}$H$_{115}$N$_{11}$O$_{15}$ 1301.9, found 1302.

η-Hydroxycyclosporin A (OL-17) 2.11:

A solution of the diacetate 4.23 in MeOH was treated with NaOMe (4 eq.) and the reaction was stirred for 2.5 hours at room temperature. The mixture was concentrated in vacuo, the residue was dissolved in methyl tert-butyl ether, washed with H$_2$O, brine, and 1 N NaHCO$_3$, dried over Na$_2$SO$_4$ filtered, and concentrated in vacuo. The residue was purified by flash chromatography (40% acetone/hexane) to give 32 mgs (50% yield) of the title compound. FABMS calculated for C$_{62N111}$N$_{11}$O$_{13}$ 1217.9, found 1218.9.

OL-17 p-Nitrophenol carbonate:

A solution of η-hydroxycyclosporin A (28 mg, 0.0227 mmol) and p-nitrophenol chloroformate (0.025 mmol) in DCM (0.5 ml) was treated with DIEA (0.004 ml, 0.025 mmol) and the reaction was stirred overnight at room temperature. The reaction was concentrated in vacuo and the residue was purified by flash chromatography (2–3% MeOH/DCM) to give 23 mgs (74% yield) of the carbonate. FABMS found 1383.7.

Example 3

Synthesis of FKBP Inhibitors

3-Phenyl-1-(3-hydroxyphenyl)-propanol 11.10:

A solution of 3-hydroxybenzaldehyde (4.5 g, 37 mmol) in THF (50 ml) was treated with 2-phenethylmagnesium chloride (1.0 M in THF, 77.5 ml, 77.5 mmol) at −78° C. under argon. The reaction was stirred for 4 hours at −78° C., diluted with EthOAc (50 ml) and quenched with 1 N HCl (150 ml). The phases were separated and the organic phase was dried over Na$_2$SO$_4$, filtered, and concentrated in vacuo. The white solid was recrystallized from 20% EthOAc/hexane to give 6.02 g (72% yield) of the title compound 11.10. R$_f$=0.24 (30% EthOAc/hexane). $^1$H NMR (300 MHz, CDCl$_3$) δ 7.23–7.15 (m, 6H), 6.93–6.84 (m, 2H), 6.79–6.71 (m, 1H), 4.95 (br s, 1H), 4.65 (t, 1H, J=5.6 Hz), 2.81–260 (m, 2H), 2.19–1.95 (m, 2H), 1.89 (br s, 1H).

3-Phenyl-1-(3-hydroxyphenyl)-propan-1-one 11.11:

A solution of alcohol 11.10 (4 g, 17.5 mmol) in acetone (40 ml) was treated with Jones Reagent at room temperature until a yellow color persisted. The reaction was quenched with isopropanol, diluted with EthOAc, and washed with H$_2$O. The organic layer was dried over Na$_2$SO$_4$, filtered, and concentrated in vacuo. The residue was purified by flash chromatography (25% EthOAc/hexane) and then recrystallized from hexane/EthOAc to give 2.23 g (56% yield) of the title compound. R$_f$=0.6 (40% EthOAc/hexane). $^1$H NMR (300 MHz, CDCl$_3$) δ 7.54–7.46 (m, 2H), 7.36–7.17 (m, 6H), 7.09–7.03 (m, 1H), 3.33–3.21 (m, 2H), 3.11–3.02 (m, 2H).

3-Phenyl-1-(3-acetoxyphenyl)-propan-1-one 11.12:

A solution of the phenol 11.11 (845 mg, 3.72 mmol) in DCM (3.72 ml) and pyridine (0.316 ml, 3.91 mmol) was treated with acetic anhydride (6 ml) at room temperature. The reaction was stirred for 4 hours, diluted with EthOAc, and washed with H$_2$O. The organic layer was dried over Na$_2$SO$_4$, filtered, and concentrated in vacuo. The residue was purified by flash chromatography (20% EthOAc/hexane) to give 840 mg (84% yield) of the title compound 11.12. R$_f$=0.26 (20% EthOAc/hexane). $^1$H NMR (300 MHz, CDCl$_3$) δ 7.82 (ddd, 1H, J=7,2.1,2.1 Hz), 7.67 (dd, 1H, J=1.9, 1.9 Hz), 7.47 (dd, 1H, J=7.9, 7.9 Hz), 7.34–7.16 (m, 6H), 3.32–3.24 (m, 2H), 3.10–3.02 (m, 2H), 2.32 (s, 3H).

(1R)-3-Phenyl-1-(3-acetoxyphenyl)-propan-1-ol 11.13:

To a solution of (+)-b-chlorodiisopinocampheylborane (6.09 g, 19.0 mmol) in THF (6 ml) at 0° C. was added a solution of ketone 11.12 (800 mmol, 2.97 mmol) in THF (3 ml). The reaction was stirred overnight at −25° C., and concentrated to a residue which was dissolved in ether (50 ml) and treated with diethanolamine (1 ml). After stirring for 3 hours at room temperature, the resulting white precipitate was removed by filtration, and the filtrate was concentrated in vacuo and purified by flash chromatography (20% EthOAc/hexane) to give 697 mg (88% yield) of the title compound 11.13. R$_f$=0.17 (20% EhOAc/hexane). $^1$H NMR (300 MHz, CDCl$_3$) δ 7.30–7.07 (m, 71–1), 7.01 (m, 1H), 6.92 (ddd, 1H, J=7.0, 7.0, 7.5 Hz), 4.61 (dd, 1H, J=7.7, 5.3 Hz), 2.74–2.52 (m, 2H), 2.22 (s, 3H), 2.10–1.69 (m, 3H).

(1R)-3-Phenyl-1-(3-hydroxyphenyl)-propan-1-ol 11.14:

A solution of acetate 11.13 (680 mmol, 2.51 mmol) in MeOH (10 ml) at 0° C. was treated with a solution of Na$_2$CO$_3$ (318 mg, 3.01 mmol) in MeOH (1 ml) and the reaction was stirred for 4 hours. The reaction was diluted with DCM (50 ml) and acidified to pH 2 with 0.1 N HCl (aq). The layers were separated and the organic phase was dried over Na$_2$SO$_4$, filtered, and concentrated in vacuo. The residue was purified by flash chromatography (20% EthOAc/hexane) to give 409 mg (72% yield) of the title compound. R$_f$=0.24 (30% EthOAc/hexane), $^1$H NMR (300 MHz, CDCl$_3$) δ 7.23–7.15 (m, 6H), 6.93–6.84 (m, 2H), 6.79–6.71 (m, 1H), 4.95 (br s, 1H), 4.65 (t, 1H, J=5.6 Hz), 2.81–2.60 (m, 2H), 2.19–1.95 (m, 2H), 1.89 (br s, 1H).

(1R)-3-Phenyl-1-(3-(1-allylhexanoate)phenyl)-propan-1-ol 11.15:

A solution of alcohol 11.14 (50 mg, 0.22 mmol) and 1-bromo allylhexanoate (80 mg, 0.34 mmol) in dioxane (2.2 ml) was treated with Cs$_2$CO$_3$ (160 mg, 0.48 mmol) and the reaction was stirred at 40° C. overnight. The reaction was diluted with EthOAc, washed with H$_2$O, dried over Na$_2$SO$_4$, filtered, and concentrated in vacuo. The residue was purified by flash chromatography (20% EthOAc/hexane) to give 67 mg (80% yield) of the title compound 11.15. R$_f$=0.23 (20% EthOAc/hexane). $^1$H NMR (300 MHz, CDCl$_3$) δ 7.34–7.14 (m, 6H), 6.97–6.87 (m, 2H), 6.8 (m, 1H), 5.92 (m, 1H), 5.38–5.21 (m, 2H), 4.65 (t, 1H, J=6.5 Hz), 4.61–4.55 (m, 2H), 3.96 (t, 2H, J=6.4 Hz), 2.83–2.6 (m, 2H), 2.37 (t, 2H, J=7.5 Hz), 2.20–1.94 (m, 3H), 1.87–1.66 (m, 4H), 1.60–1.45 (m, 2H).

(1R)-3-Phenyl-1 (3-t-butylacetoxy)phenyl)-propan-1-ol 11.16:

A solution of alcohol 11.14 (70 mg, 0.31 mmol), tert-butyl chloroacetate (0.93 ml, 0.65 mmol), TBAI (cat.) in dioxane (1 ml), and Cs$_2$CO$_{03}$ (210 mg, 0.65 mmol) was stirred at 60° C. for 5 hours. The reaction was diluted with EthOAc, washed with H$_2$O, dried over Na$_2$SO$_4$, filtered, and concentrated in vacuo. The residue was purified by flash chromatography (20% EthOAc/hexane) to give 100 mg (95% yield)

of the title compound. $R_f$=0.22 (20% EthOAc/hexane). $^1$H NMR (300 MHz, CDCl$_3$) δ 7.31–7.14 (m, 6H), 7.0–6.9 (m, 2H), 6.79 (m, 1H), 4.64 (m, 1H), 4.51 (s, 2H), 2.80–2.59 (m, 2H), 2.17–1.87 (m, 3H), 1.48 (s, 9H).

Methyl-(2S)-1-(1,2dioxo-2-methoxyethyl)-2-piperidinecarboxylate 11.18:

A solution of Boc-Pip-OH (500 mg, 2.18 mmol) in DMF (4.5 ml) was treated with Cs$_2$CO$_3$ (1.5 g, 4.58 mmol) and MeI (0.300 ml, 4.58 mmol). The reaction was stirred at room temperature for 4 hours and then poured into EthOAc/H$_2$O. The phases were separated and the organic phase was washed with 1 N NaHCO$_3$ and brine, dried over Na$_2$SO$_4$, filtered, and concentrated in vacuo to give the methyl ester 11.17 which was used directly in the next reaction. Ester 11.17 was dissolved in 4 N HCl/dioxane (15 ml) and stirred for 1 hour at room temperature. After concentrating the solution from DCM and ether several times until a white solid remained, the HCl salt was dried in high-vacuum over KOH for 3 hours and then suspended in DCM (11 ml) at 0° C. Methyl oxalyl chloride (0.222 ml, 2.4 mmol) was added to the solution, followed by DIEA (ca. 1.2 ml, 6.76 mmol) dropwise until the solution was pH 10. The reaction was stirred at room temperature for 1 hour at 0° C., diluted with EthOAc, washed with 1 N NaHCO$_3$, 1 N KHSO$_3$, brine, dried over Na$_2$SO$_4$, filtered, and concentrated in vacuo. The residue was purified by flash chromatography (30% EthOAc/hexane) to give 430 mg (86% yield) of the title compound 11.18. $R_f$=0.23 (20% EthOAc/hexane). $^1$H NMR (300 MHz, CDCl$_3$, 3:1 mixture of trans:cis isomers, data for trans) δ 5.23 (d, 1H, J=5.5 Hz), 3.87 (s, 3H), 3.75 (s, 3H), 3.57 (br d, 1H, J=12 Hz), 3.33 (td, 1H, J=13, 3 Hz), 2.29 (m, 1H), 1.82–1.34 (m, 5H).

Methyl (2S)-1-(1,2dioxo-3,3-dimethylpentyl)-2-piperidinecarboxylate 11.19:

A solution of ester 11.18 in THF at −78° C. was treated with 1,1-dimethylpropylmagnesium chloride and the resulting solution was stirred for 4 hours at −78° C. After pouring the reaction into EthOAc/sat. NH$_4$Cl, the phases were separated and aqueous phase was extracted with EthOAc. The organic layers were combined, dried over Na$_2$SO$_4$, filtered, and concentrated in vacuo. The residue was purified by flash chromatography (10% EthOAc/hexane) to give 267 mgs (56% yield) of the title compound 11.19. $R_f$=0.26 (20% EthOAc/hexane). $^1$H NMR (300 MHz, CDCl$_3$, 4:1 mixture of trans:cis isomers, data for trans isomer) δ 5.27 (d, 1H, J=5.5 Hz), 3.77 (s, 3H), 3.4 (br d, 1H, J=13.2 Hz), 3.24 (td, 1H, J=13,3 Hz), 2.32 (br d, 1H, J=14 Hz), 1.85–1.33 (m, 7H), 1.25 (s, 3H), 1.21 (s, 3H), 0.90 (t, 3H, J=7.5 Hz).

(1R)-3-Phenyl-1-[3-(tert-butylacetoxy)phenyl]-1-propanyl (2S)-1-(3,3-dimethyl-1,2-dioxopentyl)-2-piperidine carboxylate 11.21:

A solution of ester 11.19 (260 mgs, 0.973 mmol) in methanol at 0° C. was treated with LiOH (aq) (1.46 ml, 1 N LiOH) and the reaction was stirred overnight at room temperature. The mixture was concentrated in vauco, dissolved in H$_2$O, acidified to pH 3 with 1 N HCl, and extracted with DCM. The combined organics were dried over Na$_2$SO$_4$, filtered, and concentrated in vacuo to give 229 mg (93% yield) of the acid 11.20, which was used crude in the next reaction. A solution of the pipecolic acid derivative 11.20 (61 mg, 0.239 mmol) and the alcohol (90 mg, 0.263 mmol) in DCM (3 ml) was treated with DCC (57 mg, 0.276 mmol) and DMAP (18 mg, 0.143 mmol). The reaction was stirred overnight at room temperature, diluted with a small amount of EthOAc, and filtered through celite. The filtrate was concentrated in vacuo and purified by flash chromatography (10% EthOAc/hexane) to give 95 mg (68% yield) of the FKBP inhibitor 1121. $R_f$=0.42 (20% EthOAc/hexane). $^1$H NMR (300 MHz, CDCl$_3$, 6:1 mixture of trans:cis isomers, data for trans isomers) δ 7.35–7.10 (m, 6H), 7.02–6.80 (m, 3H), 5.79 (dd, 1H, J=7.5, 5.9 Hz), 5.32 (d, 1H, J=5.6 Hz), 4.53 (s, 2H), 3.35 (d, 1H, J=12 Hz), 3.14 (td, 1H, J=12, 3 Hz), 2.73–2.54 (m, 2H), 2.45–2.02 (m, 3H), 1.84–1.56 (m, 7H), 1.4 (s, 9H), 1.23 (s, 3H), 1.20 (s, 3H), 0.89 (t, 3H, 7.4 Hz).

(1R)-3-Phenyl-1-[3-((6-allyl hexanoate)oxy)phenyl]-1-propanyl-(2S)-1-(3,3-dimethyl-1,2-dioxopentyl)-2-piperidine carboxylate 11.22:

A solution of the pipecolic acid derivative 11.20 (80 mg, 0.310 mmol) and the alcohol (130 mg, 0.341 mmol) in DCM (1.6 ml) was treated with DCC (77 mg, 0.372 mmol) and DMAP (23 mg, 0.186 mmol). The reaction was stirred overnight at room temperature, diluted with a small amount of EthOAc, and filtered through celite. The filtrate was concentrated in vacuo and purified by flash chromatography (10% EthOAc/hexane) to give 140 mg (73% yield) of the FKBP inhibitor 11.22. $R_f$=0.28 (20% EthOAc/hexane), $^1$H NMR (300 MHz, CDCl$_3$ 6:1 mixture of trans: cis isomers, data for trans) δ 7.32–7.10 (m, 6H), 6.95–6.77 (m, 3H), 5.91 (m, 1H), 5.77 (dd, 1H, J 7.5, 5.9 Hz), 5.37–5.19 (m, 3H), 4.58 (d, 2H, J=5.7 Hz), 3.96 (t, 3H, J 6.2 Hz), 3.37 (br d, 1H, J=13 Hz), 3.16 (td, 1H, J=13.3 Hz), 2.62 (m, 3H), 2.37 (t, 2H, J 7.4 Hz), 2.31–2.03 (m, 2H), 1.85–1.30 (m, 14H), 1.23 (s, 3H), 1.20 (s, 3H), 0.89 (t, 3H, J=7.5 Hz). MALDI-TOV MS: found 579.6 [M], 602.8 [M+Na$^+$], 618.7 M+K$^+$].

(1R)-3-Phenyl-1-[3-(acetoxy acid)phenyl]-1- propanyl-(2S)-1-(3,3-dimethyl-1,2-dioxopentyl)-2-piperidine carboxylate 10.6:

A solution of FKBP inhibitor ester 11.21 (260 mgs, 0.973 mmol) in DCM (5 ml) was treated with TFA (1 ml) and the reaction was stirred until TLC showed consumption of starting material (ca. 1 hour). The solution was concentrated numerous times from ether, DCM, and toluene until a foam appeared. The reaction produced 80 mgs (100%) of 10.6 which was used directly in Aβ-binding -peptide reactions after drying overnight in high vacuum and without further purification.

(1R)-3-Phenyl-1-[3-((6-heanoic acid)oxy)phenyl]-1-proanyl-(2S)-1-(3,3 dimethyl-1,2-dioxopentyl)-2-piperidine carboxylate 10.7:

A solution of FKBP inhibitor ester 11.22 (30 mg, 0.052 mmol), morpholine (0.045 md, 0.52 mmol), and PPh$_3$ (7 mg, 0.0256 mmol) were treated with Pd(OAc)$_2$ (1.25 mg, 0.005 mmol) and the reaction was stirred at room temperature overnight. After concentrating in vacuo, the reaction was dissolved in EthOAc, washed with brine and KHSO$_4$ (3×), dried over Na$_2$SO$_4$, filtered, and concentrated in vacuo. The resulting yellow residue was brought up in ether, filtered through celite, and then triturated with ether/hexane to give 25 mgs (89%) of 10.7 which was used directly in the coupling reactions with the A,β-binding-peptides without any further purification.

Example 4

Synthesis of CsA analog/Aβ-Binding Peptide Conjugates

Fmoc-K(2Cl-Cbz)LVIFF/[MeLeu (3-OH)$^1$, DMcAla$^{4,6}$, Lys$^7$]CsA conjugate 11.30:

A solution of Fmoc-K(2Cl-Cbz)LVFF-OH 11.26 (12.5 mg, 0.0125 mmol) and CsA analog 10.1 (15 mg, 0.0132 mmol, produced from Cbz-protected 11.8 via general procedure K) in DMP (0.5 ml) were treated with PyAOP (7 mg, 0.0132 mmol), DIEA (0.0025 ml, 0.0132 mmol), and then stirred overnight at room temperature. (Extra DIEA was added as needed to the pH of the reaction basic.) The reaction was concentrated from toluene several times by evaporation and then purified by silica gel chromatography (2–3–4% DCM/MeOH) to give 17 mg (65% yield) of conjugate 11.30.

Ac-K(2Cl-Cbz)LVFF-/[MeLeu (3-OH$^1$, (D)MeAla$^{4,6}$, Lys$^7$] CsA conjugate 11.31:

A solution of Ac-K(2Cl-Cbz)LVFF-OH 11.27 (20 mg, 0.0241 mmol) and CsA analog 10.1 (30 mg, 0.0265 mmol, produced from Cbz-protected 11.8 via general procedure K) in DMF (1.0 ml) were treated with PyAOP (14 mg, 0.0265 mmol), DIEA (0.009 ml, 0.051 mmol), and then stirred overnight at room temperature. (Extra DIEA was added as needed to maintain the pH of the reaction.) The reaction was concentrated from toluene several times evaporation and then purified by silica gel chromatography (2–3–4–5% DCM/MeOH) to give 34 mg (75% yield) of conjugate 11.31. $R_f$=0.42 (9:1 DCM/MeOH). FABMS $C_{110}H_{159}N_{18}O_{20}Cl$) found 1981.7 [M+H$^+$].

Fmoc-EK(2Cl-Cbz)LVFF-NH$_2$/[MeLeu(3OH)$^1$, (D)MeAla$^{4,6}$, , Lys$^7$]CsA conjugate 11.32:

A solution of Fmoc-EK(2Cl-Cbz)LVFF-NH$_2$ 11.28 (14 mg, 0.012 mmol) and CsA analog 10.1 (15 mg, 0.0132 mmol, produced from Cbz-protected 11.8 via general procedure K) in DMF (0.5 ml) were treated with PyAOP (7 mg, 0.0132 mmol), DIEA (0.005 ml, 0.025 mmol), and then stirred overnight at room temperature. (Extra DIEA was added as needed to maintain the basic pH of the reaction.) The reaction was concentrated from toluene several times by evaporation and then purified by silica gel chromatography (2–3–4–5% DCM/MeOH) to give 10 mg (37% yield) of conjugate 11.32.

Ac-EK(2Cl-Cbz)LVFF-NH$_2$/[MeLeu(3-OH)$^1$, (D)MeAla$^{4,6}$, Lys$^7$]CsA conjugate 11.33:

A solution of Ac-EK(2Cl-Cbz)LVFF-NH$_2$ 11.29 (12 mg, 0.012 mmol) and CsA analog 10.1 (15 mg, 0.013 mmol, produced from Cbz-protected 11.8 via general procedure K) in DMF/LiCl (spatula head) (0.5 ml) were treated with PyAOP (7 mg, 0.013 mmol), DIEA (0.005 ml, 0.025 mmol), and then stirred overnight at room temperature. (Extra DIEA was added as needed to maintain basic pH!). After concentrating the reaction from toluene several times by evaporation, the white slurry was taken up in 7:3 DCM/MeOH and filtered through celite. The filtrate was the concentrated and purified by silica gel chromatography (2–3–4–5% DCM/MeOH), and then purified on a second column (5% MeOH/DCM) to give 10 mg (40% yield) of conjugate 11.33. FABMS $C_{106}H_{167}N_{20}O_{22}Cl$) found 2109 [M+H$^+$].

Ac-KLVFF-/[MeLeu(3-OH)$^1$, (D)MeAla$^{4,6}$, Lys$^7$]CsA conjugate 10.2:

A solution of conjugate 11.31 (17 mg, 0.008 mmol) in 4:1 MeOH/HOAc (1.0 ml) was hydrogenated under 1 atm H$_2$ according to general procedure K using Pd(OH)$_2$ (5 mg) to give a quantitative yield of the deprotected conjugate acetate salt 10.2. FABMS ($C_{93}H_{154}N_{18}O_{18}$) found 1813 [M+H$^+$]. MALDI-TOV MS: Found 1812.9 [M+H$^+$], 1834.9 [M+Na$^+$].

Ac-EKLVFF-NH$_2$/[MeLeu(3-OH)$^1$, DMeAla$^{4,6}$, Lys$^7$]CsA conjugate 10.3:

A solution of conjugate 11.33 (17 mg, 0.008 mmol) in 4:1 MeOH/HOAc (1.0 ml) was hydrogenated (initially as a slurry) under 1 atm H$_2$ according to general procedure K using Pd(OH)$_2$ (5 mg). The salt was purified by sephadex chromatography (LH-20, MeOH) to give a quantitative yield of the deprotected conjugate acetate salt 10.3. FABMS ($C_{98}H_{162}N_{20}O_{20}$) found 1941 [M+H$^+$].

Example 5

Synthesis of BP Inhibitor/Aβ-Binding Peptide Conjugates

Pyridyl acetyl-KLVFF-NE$_2$/FKBP inhibitor conjugate 10.8:

A solution of pyridyl acetyl-K(alloc)-LVFF-NH$_2$ 11.39 (22 mg, 0.0288 mmol) and FKBP inhibitor 10.6 (15 mg, 0.0288 mmol) in DMF (0.5 ml) were treated sequentially with HOBt (5 mg, 0.0317 mmol), DIEA (0.011 ml, 0.0605 mmol), and EDCI (6 mg, 0.0288 mmol) and the resulting mixture was stirred for 6 hours at room temperature. The solution was dissolved in DCM, washed with 1 N NaHCO$_3$ (2×), and concentrated in vacuo to a residue which was purified by flash chromatography (2–4–6% MeOH/DCM) to give 13 mgs (37% yield) of conjugate 10.8. The conjugate was immediately concentrated from TFA to produce the methanol soluble salt. $R_f$ (neutral conjugate)=0.31 (9:1 DCM/MeOH). FABMS $C_{72}H_{93}N_9O_{18}$) found 1277 [M+H$^+$].

Pyridyl acetyl-K(alloc)LVFFK-NH$_2$/FKBP inhibitor conjugate 10.9:

A solution of pyridyl acetyl-K(alloc)-LVFFK-NH$_2$ 11.40 (75 mg, 0.062 mmol) and FKBP inhibitor 10.6 (30 mg, 0.052 mmol) in DMF (0.7 ml) were treated sequentially with HOBt (11 mg, 0.078 mmol), DIEA (0.032 ml, 0.18 mmol), and EDCI (12 mg, 0.062 mmol) and the resulting mixture was stirred for 6 hours at room temperature. The solution was concentrated from toluene to remove the DMF and then brought up in 30% MeOH/DCM, filtered through celite and concentrated in vacuo. The residue was purified by flash chromatography (3–4–5–6% MeOH/DCM) to give 15 mgs (20% yield) of conjugate 10.9. The conjugate was immediately concentrated from TFA to produce the methanol soluble salt. FABMS ($C_{82}H_{109}N_{11}O_{15}$) found 1489 [M+H$^+$].

Pyridyl acetyl-KLVFF-NH$_2$/FKBP inhibitor conjugate 10.10.

A solution of pyridyl acetyl-K(alloc)-LVFF-NH$_2$ 11.39 (30 mg, 0.039 mmol) and FKBP inhibitor 10.7 (15 mg, 0.026 mmol) in DMF (0.5 ml) were treated sequentially with HOBt (6 mg, 0.039 mmol), DIEA (0.011 ml, 0.065 mmol), and EDCI (7.5 mg, 0.039 mmol) and the resulting mixture was stirred overnight at room temperature. The solution was concentrated from toluene to remove the DMF and then brought up in 30% MeOH/DCM, filtered through celite and concentrated in vacuo. The residue was purified by flash chromatography (2–4–6% MeOH/DCM) to give 15 mgs (43% yield) of conjugate 10.10. The conjugate was immediately concentrated from DCM/TFA to produce the methanol soluble salt. $R_f$=0.28 (90:10 DCM/MeOH). FABMS ($C_{76}H_{101}N_9O_{12}$) found 1333 [M+H$^+$].

Dowex is a registered trade mark of the Dow Chemical Company. Sephadex is a registered trade mark of Pharmacia Laboratories.

What is claimed is:

1. Compounds of formula A-Z, wherein A is selected from the group consisting of

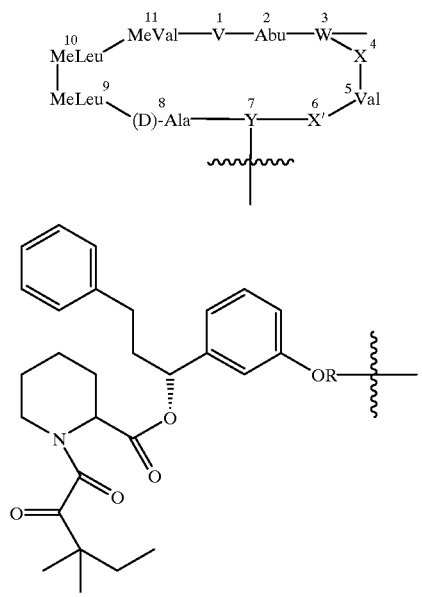

wherein R is a $C_2$ to $C_6$ alkylcarboxy group (—$(CH_2)_{1-5}$C(=O)O—);

V is a MeLeu(3-OH), MeLeu, MeSer, MeSer-PG, MeThr, or MeThr-PG residue;

W is a (D)-N-methyl-amino acid or an N-methylglycidyl residue;

X and X' are independently an N-methyl-leucinyl or an N-methylalanyl residue;

Y is a lysyl, homo-lysyl, ornithinyl, lysyl-PG, homo-lysyl-PG, or ornithinyl-PG residue;

wherein each PG is, independently, a side-chain protecting group; and

Z is a polypeptide comprising 5 or more contiguous residues of Aβ peptide; and salts thereof.

2. Compounds according to claim 1, wherein A is

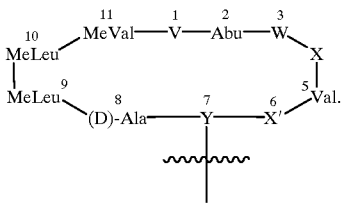

3. Compounds according to claim 2, wherein Y is a lysyl residue.

4. Compounds according to claim 2, wherein V is a MeLeu(3-OH) residue, W is a (D)-N-methyl-amino acid or an N-methylglycyl residue; X and X' are N-methylalanyl residues; and Y is a lysyl residue.

5. Compounds according to claim 2, wherein Z is selected from the group consisting of KLVFF- (SEQ. ID. NO: 25), QKLVFF- (SEQ. ID. NO: 24), KLVFFK-(SEQ. ID. NO: 31), -EKLVFF (SEQ. ID. NO: 27), and salts thereof.

6. Compounds according to claim 1, wherein A is

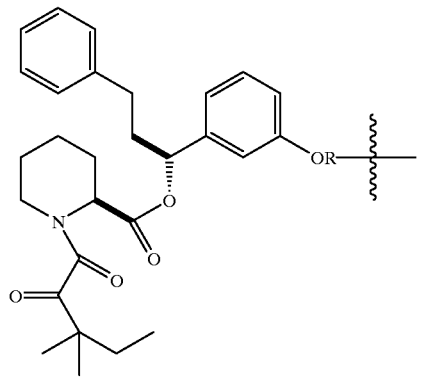

7. Compounds according to claim 6, wherein Z is selected from the group consisting of KLVFF- (SEQ. ID. NO: 25), QKLVFF- (SEQ. ID. NO: 24), KLVFFK- (SEQ. ID. NO: 31), -EKLVFF (SEQ. ID. NO: 27), and salts thereof.

8. A composition for the treatment of neurological disorders in humans involving the formation of amyloid plaques, the composition comprising an amount of one or more compounds according to any one of the preceding claims or a pharmaceutically-acceptable salt thereof in combination with a pharmaceutically-acceptable carrier, wherein the amount is effective to inhibit formation of amyloid plaques.

9. A method of treating neurological disorders in mammals involving the formation of amyloid plaques, the method comprising administering an effective amyloid plaque-inhibiting amount of a compound according to claim 1 to a mammal in need thereof.

10. The method of claim 9, wherein the amount is administered to a human in need thereof.

11. The method of claim 10, wherein the neurological disorder being treated is Alzheimer's disease.

12. The method of claim 10, wherein the neurological disorder being treated is multiple sclerosis.

13. The method of claim 10, wherein the neurological disorder being treated is amyotrophic lateral sclerosis.

* * * * *